United States Patent
Rathbone et al.

(10) Patent No.: US 12,065,635 B2
(45) Date of Patent: Aug. 20, 2024

(54) ORGAN-ON-CHIP PLATFORMS WITH REDUCED FLUID VOLUME

(71) Applicant: Massachusetts Institute of Technology, Cambridge, MA (US)

(72) Inventors: Daniel Rodion Rathbone, Somerville, MA (US); David L. Trumper, Plaistow, NH (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 1139 days.

(21) Appl. No.: 16/358,137

(22) Filed: Mar. 19, 2019

(65) Prior Publication Data

US 2019/0330584 A1 Oct. 31, 2019

Related U.S. Application Data

(60) Provisional application No. 62/645,080, filed on Mar. 19, 2018.

(51) Int. Cl.
*C12M 1/00* (2006.01)
*B01L 3/00* (2006.01)
(Continued)

(52) U.S. Cl.
CPC ......... *C12M 29/24* (2013.01); *B01L 3/50273* (2013.01); *C12M 21/08* (2013.01);
(Continued)

(58) Field of Classification Search
None
See application file for complete search history.

(56) References Cited

U.S. PATENT DOCUMENTS

| 5,468,605 A | 11/1995 | Harris |
| 6,103,199 A | 8/2000 | Bjornson |

(Continued)

FOREIGN PATENT DOCUMENTS

| CN | 103672016 | 3/2014 |
| CN | 107659208 | 2/2018 |

(Continued)

OTHER PUBLICATIONS

Busek et al., Microfluidic system for in-vitro hypoxia assays, Feb. 28, 2017, Proc. SPIE 10061 (Year: 2017).*

(Continued)

*Primary Examiner* — Holly Kipouros
(74) *Attorney, Agent, or Firm* — PABST PATENT GROUP LLP

(57) ABSTRACT

Organ-on-chip platforms with reduced fluid volumes include circulating fluid volumes of below 1000 μL, preferably about 500 μL or less. The platforms are adjustable for culturing cells with varied oxygen demand at various seeding densities. The platforms include at least one lane, wherein each lane includes at least one cell culture well, at least one oxygenator for fluid oxygenation, and a pump system containing at least one pump per lane. The oxygenator may include a separate fluid path for oxygenating the fluid, which allows controlling and measuring the oxygen concentration in the fluid, shortening the diffusion length, and passively diffusing oxygen. Provided are also different configurations for the oxygenator, fluid circulation in the platforms, attachment means for securing scaffolds to culture wells, and pneumatic plates.

25 Claims, 26 Drawing Sheets

(51) Int. Cl.

| | |
|---|---|
| C12M 1/02 | (2006.01) |
| C12M 1/12 | (2006.01) |
| C12M 1/32 | (2006.01) |
| C12M 1/34 | (2006.01) |
| C12M 3/00 | (2006.01) |
| C12M 3/06 | (2006.01) |
| C12N 5/071 | (2010.01) |
| G01N 33/50 | (2006.01) |

(52) U.S. Cl.
CPC ............ *C12M 23/12* (2013.01); *C12M 23/16* (2013.01); *C12M 23/44* (2013.01); *C12M 23/46* (2013.01); *C12M 25/06* (2013.01); *C12M 25/14* (2013.01); *C12M 27/00* (2013.01); *C12M 27/18* (2013.01); *C12M 41/34* (2013.01); *C12N 5/0671* (2013.01); *C12N 5/0697* (2013.01); *G01N 33/5008* (2013.01); *G01N 33/5088* (2013.01); *B01L 2300/0829* (2013.01); *B01L 2300/0858* (2013.01); *B01L 2300/10* (2013.01)

(56) References Cited

U.S. PATENT DOCUMENTS

| | | | |
|---|---|---|---|
| 8,318,479 | B2 | 11/2012 | Domansky |
| 9,249,387 | B2 | 2/2016 | Cuiffi |
| 9,528,082 | B2 | 12/2016 | Cuiffi |
| 9,588,105 | B1 | 3/2017 | Hussain |
| 9,632,076 | B2 | 4/2017 | Achyuta |
| 10,323,221 | B2 | 6/2019 | Nguyen |
| 2001/0036672 | A1 | 11/2001 | Anderson |
| 2004/0228770 | A1 | 11/2004 | Gandhi |
| 2005/0238506 | A1 | 10/2005 | Mescher |
| 2005/0244932 | A1 | 11/2005 | Harding |
| 2005/0260745 | A1 | 11/2005 | Domansky |
| 2005/0287660 | A1* | 12/2005 | Aubry ............... C12M 29/06 435/297.1 |
| 2008/0032380 | A1* | 2/2008 | Kleis ............... C12M 23/04 435/243 |
| 2008/0166786 | A1 | 7/2008 | Nishiyama |
| 2008/0170936 | A1 | 7/2008 | Den Toonder |
| 2010/0230613 | A1 | 9/2010 | Pieprzyk |
| 2013/0020386 | A1 | 1/2013 | Yoshida |
| 2013/0068310 | A1 | 3/2013 | Sip |
| 2014/0196560 | A1 | 7/2014 | Lai |
| 2014/0354381 | A1 | 12/2014 | Kohlhafer |
| 2015/0140581 | A1 | 5/2015 | Achyuta |
| 2015/0167863 | A1 | 6/2015 | Mescher |
| 2015/0301027 | A1 | 10/2015 | Charest |
| 2016/0003229 | A1 | 1/2016 | Mescher |
| 2016/0040112 | A1 | 2/2016 | Coppeta |
| 2016/0047832 | A1 | 2/2016 | Gumbrecht |
| 2016/0129440 | A1 | 5/2016 | Borenstein |
| 2016/0145553 | A1 | 5/2016 | Cuiffi |
| 2016/0151778 | A1 | 6/2016 | McClelland |
| 2016/0220961 | A1 | 8/2016 | DiBiasio |
| 2016/0220997 | A1 | 8/2016 | Mescher |
| 2016/0244727 | A1 | 8/2016 | Borenstein |
| 2016/0326477 | A1 | 11/2016 | Fernandez-Alcon |
| 2016/0377599 | A1 | 12/2016 | Hughes |
| 2017/0227525 | A1 | 8/2017 | Griffith |
| 2020/0208088 | A1* | 7/2020 | Frey ............... G01N 33/5014 |

FOREIGN PATENT DOCUMENTS

| | | |
|---|---|---|
| GB | 2147100 | 5/1985 |
| WO | 2005123950 | 12/2005 |
| WO | 2011071772 | 6/2011 |
| WO | WO-2015003997 A1 * | 1/2015 ............ C12M 23/16 |
| WO | 2017176357 | 10/2017 |

OTHER PUBLICATIONS

Mauleon et al., Enhanced loading of Fura-2/AM calcium indicator dye in adult rodent brain slices via a microfluidic oxygenator, 2013, Journal of Neuroscience Methods, pp. 110-117 (Year: 2013).*
Anna, "Droplets and Bubbles in Microfluidic Devices", Annu. Rev. Fluid Mech., 48:285-309 (2016).
Berthier, et al., "Metastable capillary filaments in rectangular cross-section open microchannels", AIMS Biophysics, 1(1):31-48 (2014).
Brakke, et al., "The surface evolver", Exp. Math, 1(2):141-65 (1992).
Brown, et al., "Physiological parameter values for physiologically based pharmacokinetic models", Toxicol. Ind. Health, 13(4):407-84 (1997).
Chitcholtan, et al., "Differences in growth properties of endometrial cancer in three dimensional (3D) culture and 2D cell monolayer", Exp. Cell Research, 319(1):75-87 (2013).
Clark, et al., "A liver microphysiological system of tumor cell dormancy and inflammatory responsiveness", Lab Chip, 17(1):156-68 (2016).
Cook, et al., "Lessons learned from the fate of AstraZeneca's drug pipeline: a five-dimensional framework", Nat. Rev. Drug Discov., 13(6):419-31 (2014).
Coppeta, et al., "A portable and reconfigurable multi-organ platform for drug development with onboard microfluidic flow control", Lab Chip, 17:134-44 (2017).
Cosgrove, et al., "Synergistic drug-cytokine induction of hepatocellular death as an in vitro approach for the study of inflammation-associated idiosyncratic drug hepatotoxicity", Toxicol. Appl. Pharmacol., 237(3):317-330 (2009).
Danese, et al., "The CD40/CD40L costimulatory pathway in inflammatory bowel disease", Gut, 53(7):1035-43 (2004).
Denayer, et al., "Animal models in translational medicine: Validation and prediction", New Horizons Transl. Med., 2(1):5-11 (2014).
Deng, et al., "Inflammatory stress and idiosyncratic hepatotoxicity: hints from animal models", Pharma Rev., 61(3):262-82 (2009).
Ding, et al., "Bile acid nuclear receptor FXR and digestive system diseases", Acta. Pharm. Sin. B. 5(2):135-44 (2015).
Esch, et al., "Body-on-a-chip simulation with gastrointestinal tract and liver tissues suggests that ingested nanoparticles have the potential to cause liver injury", Lab Chip 14(16):3081-92 (2014).
Fink, "Animal models of sepsis", Virulence, 5(1):143-53 (2014).
Frey, et al., "The ErbB4 growth factor receptor is required for colon epithelial cell survival in the presence of TNF", Gastroenterology, 136(1):217-26 (2009).
Giese, et al., "Human immunity in vitro—solving immunogenicity and more", Adv. Drug Deliver. Rev., 69:103-22 (2014).
Guo, et al., "Lipopolysaccharide causes an increase in intestinal tight junction permeability in vitro and in vivo by inducing enterocyte membrane expression and localization of TLR-4 and CD14", Am. J. Pathol., 182(2):375-87 (2013).
Halldorsson, et al., "Advantages and challenges of microfluidic cell culture in polydimethylsiloxane devices", Biosens. Bioelectron., 63:218-31 (2015).
Huang, et al., "Therapeutic protein-drug interactions and implications for drug development", Clin. Pharmacol. Ther., 87(4):497-503 (2010).
Huebsch, et al., "Miniaturized iPS-Cell-Derived Cardiac Muscles for Physiologically Relevant Drug Response Analyses", Sci. Rep., 6:24726 (2016).
Huh, et al., "Microengineered physiological biomimicry: organs-on-chips", Lab Chip, 12(12):2156-64 (2012).
Jang, et al., "On-chip three-dimensional cell culture in phaseguides improves hepatocyte functions in vitro", Biomicrofluidics, 9 034113 1-12 (2015).
Khovidhunkit, et al., "Effects of infection and inflammation on lipid and lipoprotein metabolism: mechanisms and consequences to the host", J. Lipid. Res., 45(7):1169-96 (2004).
Kim, et al., "Role of Kupffer cells in pathogenesis of sepsis-induced drug metabolizing dysfunction", Febs. J., 278(13):2307-17 (2011).
Kubinyi, "Drug research: myths, hype and reality", Nat. Rev. Drug Discov. 2(8):665-8 (2003).

(56) References Cited

OTHER PUBLICATIONS

Leblond, et al., "Regulation of the proprotein convertase subtilisin/kexin type 9 in intestinal epithelial cells", Am. J. Physiol. Gastrointest. Liver Physiol., 296(4):G805-15 (2009).
Liaskou, et al., "Innate immune cells in liver inflammation", Mediators. Inflamm., 2012:949157 (2012).
Livingston, et al., "Facilitating the commercialization and use of organ platforms generated by the microphysiological systems (Tissue Chip) program through public-private partnerships", Comput. Struct. Biotechnol. J., 14:207-10 (2016).
Long, et al., "Modeling Therapeutic Antibody-Small Molecule Drug-Drug Interactions Using a Three-Dimensional Perfusable Human Liver Coculture Platform", Drug Metab. Dispos., 44(12):1940-8 (2016).
Loskill, et al., "uOrgano: A Lego®-Like Plug & Play System for Modular Multi-Organ-Chips", Plos One, 10(10):e0139587 (2015).
Marx, "Organs from the lab", Nature, 522:373-7 (2015).
Maschmeyer, et al., "A four-organ-chip for interconnected long-term co-culture of human intestine, liver, skin and kidney equivalents", Lab Chip, 15(12):2688-99 (2015).
Materne, et al., "A multi-organ chip co-culture of neurospheres and liver equivalents for long-term substance testing", J. Biotechnol., 205:36-46 (2015a).
Materne, et al., "The Multi-organ Chip—A Microfluidic Platform for Long-term Multi-tissue Coculture", J. Vis. Exp., 98:52526 (2015b).
Mestas, et al., "Of mice and not men: differences between mouse and human immunology", J. Immunol., 172(5):2731-8 (2004).
Morgan, "Regulation of cytochrome p450 by inflammatory mediators: why and how", Drug Metab. Dispos., 29(3):207-12 (2001).
Oleaga, et al. "Multi-Organ toxicity demonstration in a functional human in vitro system composed of four organs", Sci. Rep., 6:20030 (2016).
Pierrakos, et al., "Sepsis biomarkers: a review", Crit. Care, 14(1):R15 (2010).
Pillai, et al., "A sensitive and specific CYP cocktail assay for the simultaneous assessment of human cytochrome P450 activities in primary cultures of human hepatocytes using LC-MS/MS", J. Pharm. Biomed. Anal., 74:126-32 (2013).
Powers, et al., "A microfabricated array bioreactor for perfused 3D liver culture", Biotechnol. Bioeng., 78:257-69 (2002).
Roth, et al., "The application of 3D cell models to support drug safety assessment: opportunities & challenges", Adv. Drug Deliver. Rev., 69-70:179-189 (2014).
Rowlands, et al., "The gastrointestinal tract as a barrier in sepsis", Br. Med. Bull., 55(1):196-211 (1999).
Sarkar, et al., "Metabolite profiling and pharmacokinetic evaluation of hydrocortisone in a perfused three-dimensional human liver bioreactor", Drug Metab. Dispos., 43(7):1091-9 (2015).
Seok, et al., "Genomic responses in mouse models poorly mimic human inflammatory diseases", PNAS, 110(9):3507-12 (2013).
Sung, et al., "A micro cell culture analog (microCCA) with 3-D hydrogel culture of multiple cell lines to assess metabolism-dependent cytotoxicity of anti-cancer drugs", Lab Chip, 9:1385-96 (2009).
Sung, et al., "A microfluidic device for a pharmacokinetic-pharmacodynamic (PK-PD) model on a chip", Lab Chip, 10:446-55 (2010).
Sung, et al., "Microfabricated mammalian organ systems and their integration into models of whole animals and humans", Lab Chip, 13(7):1201-1212 (2013).
Sweeney, et al., "A cell culture analogue of rodent physiology: Application to naphthalene toxicology", Toxicol. Vitr. 9:307-16 (1995).
Trietsch, et al., "Microfluidic titer plate for stratified 3D cell culture", Lab Chip 13:3548-54 (2013).
Tsamandouras, et al., "Quantitative assessment of population variability in hepatic drug metabolism using a perfused 3D human liver microphysiological", J. Pharma. Exp. Thera., DOI: 10.1124/jpet.116.237495 (2016).

Van Midwoud, et al., "A microfluidic approach for in vitro assessment of interorgan interactions in drug metabolism using intestinal and liver slices", Lab Chip, 10(20):2778-86 (2010).
Vulto, et al., "Selective sample recovery of DEP-separated cells nd particles by phaseguide-controlled laminar flow", J. Micromech. Microeng., 16:1847-53 (2006).
Walker, et al., "Design, modeling and fabrication of a constant flow pneumatic micropump", J. Micromechanics and Microengineering 17(5):891 (2007).
Wijs, et al., "Wetting Forces and Meniscus Pinning at Geometrical Edges", Separations: Materials, Devices, and Processes, 62(12):4453-65 (2016).
Wikswo, et al., "The relevance and potential roles of microphysiological systems in biology and medicine", Exp. Biol. Med., (Maywood) 239(9):1061-72 (2014).
Yamaoka, et al., "Transactivation of EGF receptor and ErbB2 protects intestinal epithelial cells from TNF-induced apoptosis", PNAS, 105(33):11772-7 (2008).
Yates, et al., "Novel three-dimensional organotypic liver bioreactor to directly visualize early events in metastatic progression", Adv. Cancer Res. 97:225-246 (2007).
Yu, et al., "Three dimensional human small intestine models for ADME-Tox studies", Drug Discovery Today, 19(10):1587-94 (2014).
Zhang, et al., "ErbB2 and ErbB3 regulate recovery from dextran sulfate sodium-induced colitis by promoting mouse colon epithelial cell survival", Lab Invest., 92(3):437-50 (2012).
Zhu, et al., "A vertical-flow bioreactor array compacts hepatocytes for enhanced polarity and functions", Lab Chip, 16(20):3898-3908 (2016).
Anonymous: "MIT Thesis FAQ: Access and Availability Questions Search Account", Retrieved from the Internet: URL:https://libguides.mit.edu/c.php?g=176367&p=1159524#13349206 retrieved on May 27, 2019 (2019).
Barbosa, et al., "Artificial oxygen carriers as a possible alternative to red cells in clinical practice", Sao Paulo Medical Journal, vol. 128:97-100 (2009).
Berthier, et al., "A general condition for spontaneous capillary flow in uniform cross-section microchannels", Microfluid Nanofluid, 16:77-785 (2014).
Blackie, et al., "Membrane Oxygenation of Mammalian Cell Culture Fermenters Using Dupont Teflon AF-2400", Tubing, 299-301 (2002).
Busek, et al., "Hypoxia-on-a-chip", Current Directions in Biomedical Engineering, 2(1):71-75 (2016a).
Busek, et al., "Design, characterization, and modeling of microcirculation systems with integrated oxygenators", J Sensors and Sensor Systems, 5:221-8 (2016b).
Concus, et al., "On the behavior of a capillary surface in a wedge", PNAS, 63:292-9 (1969).
Dehne, et al., "The ascendance of microphysiological systems to solve the drug testing dilemma", Future Science OA, 3(2): FSO185 (2017).
Domansky, et al., "Perfused multiwell plate for 3D liver tissue engineering", Lab Chip, 10:51-8 (2010).
Ebrahimkhani, et al., "Bioreactor technologies to support liver function in vitro", Adv Drug Deliv Rev, Apr(69-70): 132-57 (2014).
Gimbel, et al., "Development of a biomimetic microfluidic oxygen transfer device", Lab Chip, 16:3227-34 (2016).
Heckele, et al., "Review on micro molding of thermoplastic polymers", J. Micromech. Microeng. 14:R1-R14 (2004).
Hoganson, et al., "Lung assist device technology with physiologic blood flow developed on a tissue engineered scaffold platform", Lab Chip, 11:700-7 (2011).
Inman, "Development of a High Throughput 3D Perfused Liver Tissue Bioreactor," Masters Thesis, Massachusetts Institute of Technology (2006).
Inman, et al., "Design, modeling and fabrication of a constant flow pneumatic micropump", J Micromech Microeng., 17(5):891-9 (2007).
International Search Report for corresponding application PCT/US2019/022887 mailed Aug. 8, 2019.
Lam, et al., "A microfluidic oxygenator for biological cell culture", Transfucers and Eurosensors, 2489-2492 (2007).

(56) References Cited

OTHER PUBLICATIONS

Liston, et al., "Plasma surface modification of polymers for improved adhesion: a critical review", J Adhesion Sci Tech, 7:1091-1127 (1993).
Low, et al., "Microphysiological Systems ("Organs-on-Chips") for Drug Efficacy and Toxicity Testing", Clin Transl Sci, 10:237-9 (2017).
Minuth, et al., "Supportive ceelopment of functional tissues for biomedical research using the Minusheet perfusion system", Clinical and Translational Medicine, 1(1): (2012).
Ng, et al., "A Comparative Study of Transmembrane Diffusion and Permeation of Ibuprofen across Synthetic Membranes Using Franz Diffusion Cells", Pharmaceutics, 2:209-223 (2010).
Oliver, et al., "Resistance to spreading of liquids by sharp edges", J Colloid Interface Sci, 59:568-81 (1977).
Oomen, et al., "Implementing oxygen control in chip-based cell and tissue culture systems", Lab Chip, 16:3394-414 (2016).
Place, et al., "Limitations of oxygen delivery to cells in culture: An underappreciated problem in basic and translational research", Free Radic Biol Med. 113:311-22 (2017).
Rathbone, "A low volume oxygenator for open well Lier-on-a-chip tissue cultere", Massachusetts Institute of Technology, Department of Mechanical Engineering, 1-150 (2018).
Sander, "Compilation of Henry's law constants (Version 4.0) for water as solvent", Atmospheric Chemistry and Physics, 15(8): 4399-981 (2015).
Sonntag, et al., "Universal lab-on-a-chip platform for complex, perfused 3D cell cultures", Progress in Biomedical Optics and Imaging, SPie-Interntional Society for Optical Engineering, 9705 (2016).
Tao, et al., "Microparticle, nanoparticle, and stem cell-based oxygen carriers as advanced blood substitutes", Trends Biotechnol, 32:466-73 (2014).
Toepke, et al., "PDMS absorption of small molecules and consequences in microfluidic applications", Lab Chip, 6:1484-6 (2006).
Tygstrup, et al., "Determination of the hepatic arterial blood flow and oxygen supply in man by clamping the hepatic artery during surgery", J Clin Invest, 41:447-54 (1962).
Volmer, et al., "Development of an integrated microfluidic platform for dynamic oxygen sensing and delivery in a flowing medium", Lab Chip, 5(10):1059-66 (2005).
Wang, et al., "A novel in vitro flow system for changing flow direction on endothelial cells", J Biomech, 45:1212-8 (2012).
Wenger et al., "Frequently asked questions in hypoxia research", Hypoxia, 3:3-435 (2015).
Wu, et al., "Lung assist device: development of microfluidic oxygenators for preterm infants with respiratory failure", Lab Chip, 13:2641-50 (2013).
Xia, et al., "Soft Lithography", Ann. Rev. Mater. Sci., 28:153-84 (1998).
Young, et al., "Contoured elastic-membrane microvalves for microfluidic network integration", J. Biomech. Eng., 121:2-6 (1999).
International Search Report for PCT application PCT/US2017/016721 mailed Dec. 4, 2017.
International Search Report for PCT application PCT/US2018/02341 mailed Oct. 25, 2018.
Domansky, et al., "Multiwell cell culture plate format with integrated microfluidic perfusion system", Proceedings vol. 6112, Microfluidics, BioMEMS, and Medical Microsystems IV; 61120F (2006).
Domansky, et al., "Perfused Microreactors for Liver Tissue Engineering", Proceedings of the 2005 IEEE, Engineering in Medicine and Biology 27th Annual Conference (2005).
Van Nguyen, "Design, Modeling, and Validation of an Apical Flow Transwell Insert for Small Intestinal Models", Thesis submitted to the Department of Mechanical Engineering at the Massachusetts Institute of Technology, 1-81, Aug. 2, 2016.

\* cited by examiner

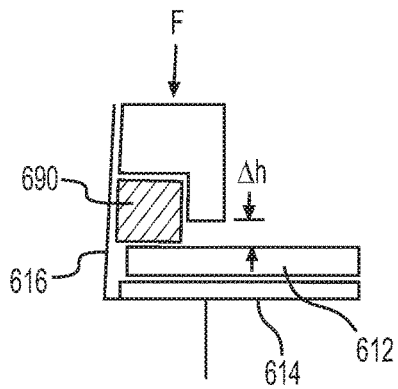 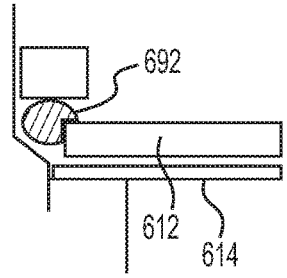 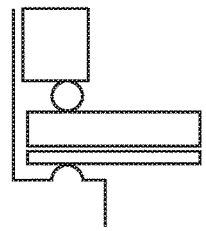
FIG. 16A  FIG. 16B  FIG. 16C
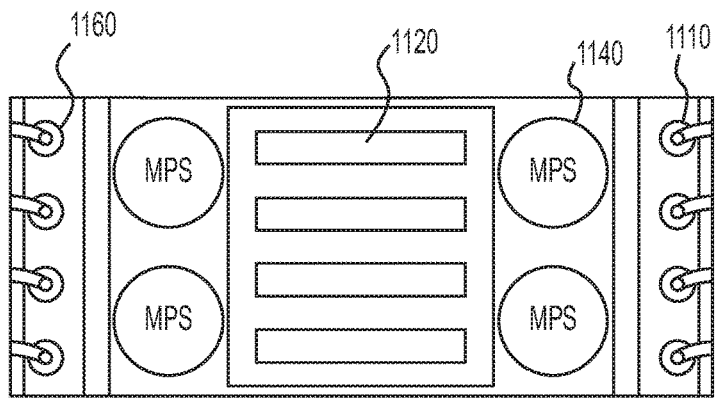 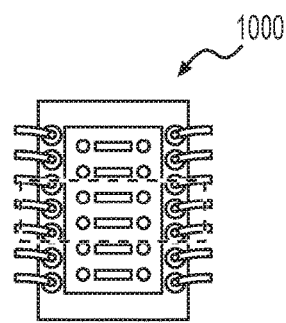
FIG. 17A  FIG. 17B
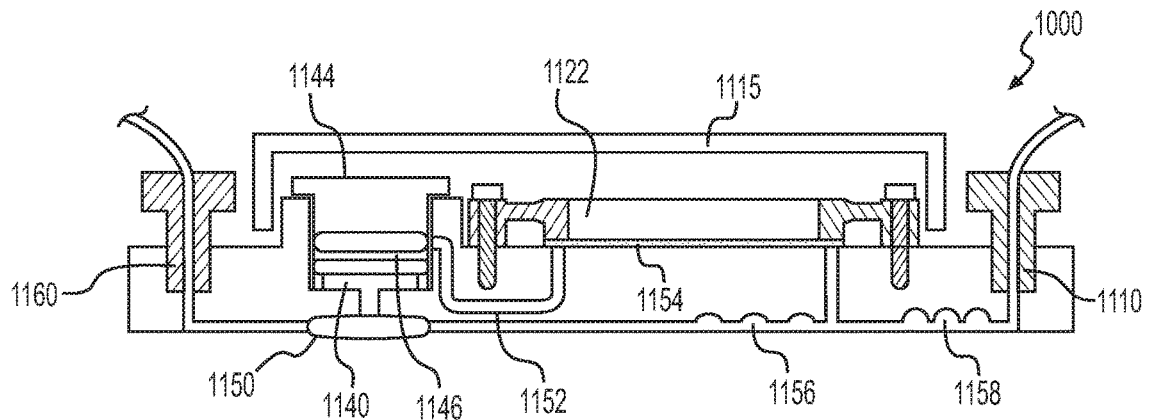
FIG. 17C

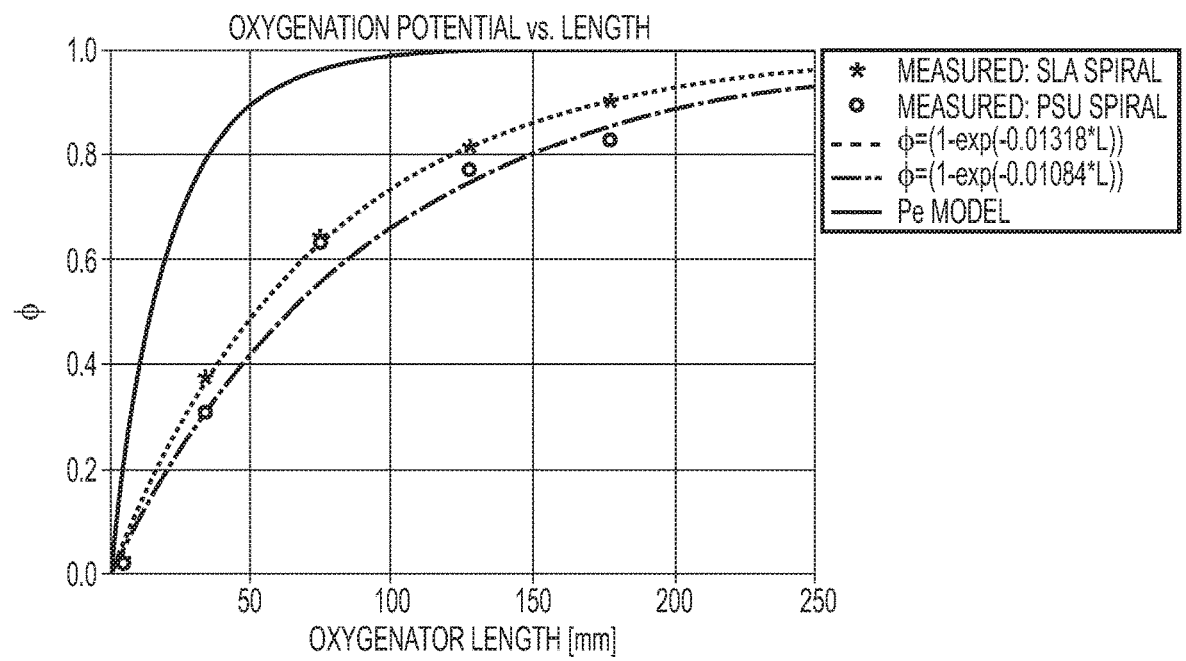
FIG. 31
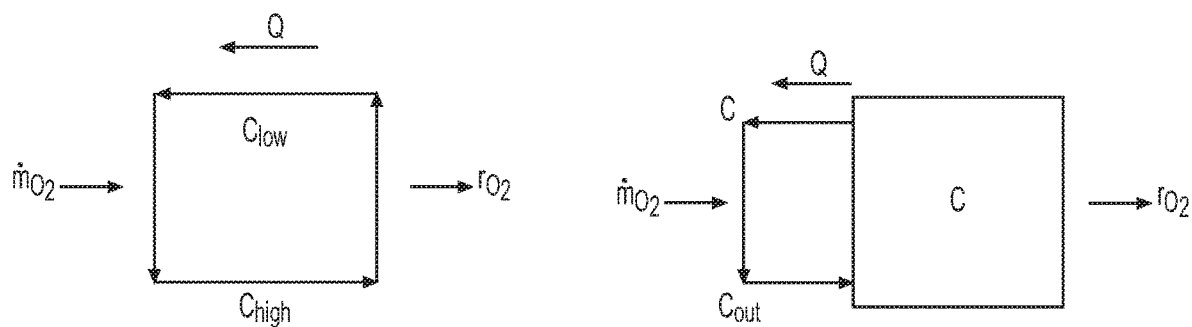
FIG. 32A  FIG. 32B

ORGAN-ON-CHIP PLATFORMS WITH REDUCED FLUID VOLUME

CROSS-REFERENCE TO RELATED APPLICATIONS

This application claims the benefit of and priority to U.S. Provisional Application No. 62/645,080 filed Mar. 19, 2018, which is incorporated herein by reference in its entirety.

STATEMENT REGARDING FEDERALLY SPONSORED RESEARCH

This invention was made with Government support under Grant No. UH3-TR000496 awarded by the National Institutes of Health. The Government has certain rights in the invention.

FIELD OF THE INVENTION

The invention is generally directed to microfluidic devices for cell and tissue culture and to the subcomponents of the microfluidic devices.

BACKGROUND OF THE INVENTION

In the long and costly process of developing a new drug, an important challenge is screening drugs for toxicity and efficacy before clinical trials. Animal models are limited in their translation to human physiology, which has caused failures in clinical trials and may cause viable drugs to be rejected (Dehne, et al., *Future Science OA*, vol. 3 (2017)). MicroPhysiological Systems (MPS), or small-scale in vitro systems that recapitulate some aspect of human physiology with human cells, show significant promise in speeding drug development and advancing basic research (Dehne, et al., *Future Science OA*, vol. 3 (2017); Low, et al. *Clinical and Translational Science*, vol. 10, pp. 237-239 (July 2017)). They may serve better than animal models for obtaining accurate human response data and thereby reducing failed clinical trials.

In available MPS, such as the LIVERCHIP® platforms (CN Bio Innovations Limited, Hertfordshire, U.K.) or those described in U.S. Application Publication Nos. US 2016/0377599 and US 2017/0227525 A1, liquid media is oxygenated in a long, wide channel to provide enough free-surface area for adequate oxygen mass transfer. This channel, referred to as the "oxygenator" or "tail", is in a closed, single-loop circuit with the cells and a circulating pump.

In these organ-on-chip systems, the concentration of various markers and metabolites produced by the cells depends on the circulating volume of fluid. A lower circulating volume requires fewer cells to produce measurable concentrations, reducing cost and avoiding some challenges associated with growing large masses of tissue. Further, various signaling compounds are likely to be closer to physiologically relevant concentrations with lower circulating volume.

The LIVERCHIP® platform perfuses the cells with a circulating volume of about 1.2 mL of growth medium, which contains nutrients and growth factors, and which transports oxygen from the free air-liquid interface in the oxygenator to the cells. A smaller circulating volume is desirable to avoid the dilution effect of larger liquid volumes for three reasons: (1) biomarkers produced in low quantities will be easier to detect; (2) intercellular communication will be promoted if autocrine compounds are less dilute; (3) less drug mass will be required to achieve the same initial concentration, and the drug exposure over time will be closer to that for humans in vivo.

While low circulating volume is desirable, there are challenges with oxygenating an open-well system at low volumes. A wide channel is susceptible to height fluctuations which allows fluid to be stored in the oxygenator while the cells run dry, ending the experiment. Lack of bidirectional flow prevents efficient oxygenation in the oxygenation tail.

Achieving adequate oxygenation at lower volumes is challenging due to surface tension effects.

The main challenge with reducing volume in an open well format is the dominance of surface tension at small length-scales. Simply putting less medium in the LIVERCHIP® platforms causes the fluid to wet the corners of the oxygenator channels, no longer providing the surface area required to adequately oxygenate the cells. Also, fluid may accumulate around the scaffold with cells preventing efficient fluid flow through the scaffold. These challenges preclude efficient operation of organ-on-chip platforms with reduced fluid volumes.

There remains a need for improved organ-on-chip platforms that operate with low circulating volumes of fluid.

Therefore, it is the object of the present invention to provide organ-on-chip platforms with low circulating volumes of fluid.

It is also the object of the present invention to provide organ-on-chip platforms with oxygenators for efficient oxygenation of low circulating volumes of fluid.

It is another object of the present invention to provide fluid circulation configurations for circulating low volumes of fluid.

It is yet another object of the present invention to provide means for effectively attaching scaffolds to wells in the organ-on-chip platforms.

SUMMARY OF THE INVENTION

Organ-on-chip platforms that operate with low circulating volumes of fluid have been developed. The platforms include oxygenators for efficient oxygenation of low circulating volumes of fluid to meet the metabolic demand of the cells and tissues in culture. The organ-on-chip platforms include one or more fluid circulation configurations for circulating low volumes of fluid.

Platforms with volume-limited free-surface oxygenators that maintain a defined fluid path even at very low volumes and fluid flow configurations that allow the oxygenators to interface with a cell culture scaffold. The sealing means prevents fluid from bypassing the scaffold in a more robust manner than in the existing MPS, such as the LIVERCHIP® platforms (CN Bio Innovations Limited, Hertfordshire, U.K.) or those described in U.S. Application Publication No. US 2017/0227525 A1.

The platforms may be open-well or closed fluidic systems. The total circulating fluid volume through the open-well systems may range between about 400 µL and 1000 µL. The total circulating fluid volume through the closed fluidic system may be between about 50 µL and 500 µL.

The open-well flow-through platforms include a low-volume oxygenator. The oxygenator typically has a body and a surface geometry suitable for oxygenating between about 300 µL and 1000 µL circulating fluids. The closed fluidic systems include membrane oxygenators configured for oxygenating between about 50 µL and 500 µL circulating fluids.

In some embodiments, the oxygenator body is an upright cone with an external spiral surface geometry. In other embodiments, the oxygenator body may be an elongated, such as an oblong, body with an external spiral surface geometry. The exterior spiral forms an interior corner of a hydrophilic surface to constrain the circulating fluid and to create a thin fluid region. This decreases the diffusion depth relative to exposed surface area, thereby improving oxygenation. The oxygenator may include a downward slope that prevents fluid from accumulating in the oxygenator, which could otherwise deplete the cell culture well.

In one embodiment, the organ-on-chip platforms are capable of adequately oxygenating and supporting cells at a seeding density of between 50 000 cells/well and 10 000 000 cells/well in a flow-through, open-well environment with a total circulating volume between about 300 μL and 1000 μL.

In another embodiment, the organ-on-chip platforms are capable of adequately oxygenating and culturing cells at a seeding density of between 50,000 cells/well and 5,000,000 cells/well in a flow-through, closed-well environment with a total circulating volume of about 500 μL or less, such as between about 50 μL and 500 μL.

The cell and tissue types suitable for culturing in the platforms include animal and human cells and tissues. Suitable types of cells and tissues include cells and tissues of animal and human organs, such as brain, heart, lung, liver, spleen, kidney, skin, muscles, bone, epithelial cells, endothelial cells, immune cells such as cells of the adaptive or innate immune systems, microorganisms, such as cells of the microbiome, as well altered or diseased cells. Examples of altered or diseased cells include cancer cells, scar-forming cells, autoreactive cells, genetically modified cells, and pathogenic microorganisms.

Also provided are means for effectively sealing or attaching scaffolds to wells in the organ-on-chip platforms. Examples of attachment means include an elastomeric retaining ring, bi-stable spring, angled ring and lip, external screw mount with tube or spring, snap fit with flexure, deflecting beam, tilting ring, wave spring, or retaining ring with elastomer. The attachment means typically secure the scaffold such that the secured scaffold does not leak more than 0.1 μL/s at a pressure differential of 40 kPa. The attachment means is typically easy to install, and may be inserted with an insertion force of less than 50N. The attachment means and its insertion method typically do not damage the scaffold, or other components of the platform.

BRIEF DESCRIPTION OF THE DRAWINGS

FIG. 2B also shows the media exchange pump 310, oxygenator pump 320, and recirculation pump 330. The components of the replicate lane 102 include a spillway 146, an effluent reservoir 160, an MPS well 140, an elongated spiral oxygenator 120, and a media reservoir 110.

FIGS. 16A-16C are diagrams showing different embodiments of a retaining ring with an elastomer as attachment means.

FIGS. 17A and 17B are diagrams showing top view of closed fluidic system 1000. FIG. 17A is an expanded view of the bracketed segment from FIG. 17B. FIG. 17A shows the platform includes membrane oxygenators 1120, MPS wells 1140, media reservoirs 1110, and effluent reservoirs 1160. FIG. 17C is a diagram of a cross-section view of a closed fluidic system 1000. The system includes a media reservoir 1110, a universal lid 1115, a clamping plate 1122, MPS cap 1144, an effluent reservoir 1160, a scaffold assembly 1146 in an MPS well 1140, fluidic capacitor 1150, oxygenator feed channel 1152, oxygenator membrane 1154, circulation/oxygenator pump 1156, and media exchange pump 1158. Each lane of the proposed closed-volume platform has a media reservoir 1110 pulling from an external reservoir, an oxygenator membrane 1154 that is clamped in place to provide a confined fluid path, an MPS cap 1144 to limit volume, and on-board pumping (pneumatic plate not shown). The MPS cap 1144 and membrane 1154 are placed under a lid for sterility, but this may be unnecessary, depending on the sterile workflow. The oxygenator feed channel 1152 is typically on the bottom plane with the other flow channels. It is shown higher in this illustration for visibility.

FIG. 18A shows the fluid path width of the fluid 1300 is defined by a clamping plate 1122 with an elastomeric gasket 1124 to distribute pressure on the membrane oxygenator 1126. The fluid path height is defined by deflection of the membrane under pressure. If the membrane is stiff relative to the path width, a spacer 1128 can be used (FIG. 18B). To halve the diffusion length and make a more compact oxygenator, a double-membrane method could be used with membranes 1126 and 1126' (FIG. 18C). This double-membrane method may create a potential leak path that may be challenging to seal by clamping alone.

FIG. 19B shows that a clamping block 1430, consisting of several bars that confine fluid flow to the empty regions, could also be secured by means of a fixed anchor 1440 at one end and an easy-to-use pivoting fastener 1450 (or multiple of these) at the other end. FIG. 19C shows the bottom membrane 1228 of a two-membrane oxygenator could potentially be bonded to a tapered plug 1442 with a through hole 1444, which would seal to the platform below. The top membrane could then be bonded or clamped to this bottom membrane 1228. In a disposable platform, the membrane might be bonded directly to the lower platform. This depends on having a thermoplastic membrane material, such as polypropylene.

FIG. 22 shows the SLA exterior spiral breadboard 202 with probes 204 and 206 in position to measure oxygenation potential. Accumulation at the base of the spiral has been reduced by including a wetted slope 208 into the cell culture well to provide reliable exit flow. A similar PSU exterior spiral breadboard was also generated.

FIG. 25A shows that as oxygen diffuses through the air-liquid interface at x=0, the concentration will decrease exponentially with x. FIG. 25B shows approximation $$\left.\frac{dC}{dx}\right|_{x=0}$$

by linearizing the concentration gradient between x=0 and x=h.

Figure 26:
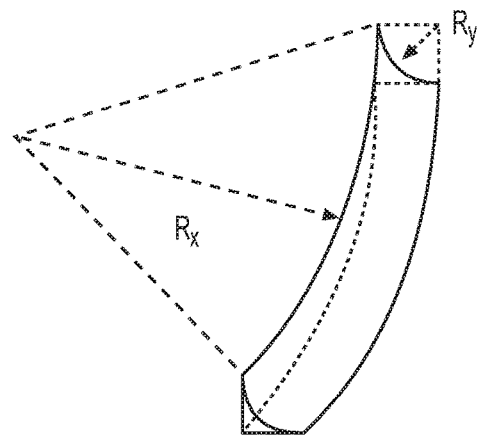

FIG. 26 is a diagram showing the radii of curvature of the fluid surface. In this case, Ry is positive and Rx is negative.

Figure 27A:
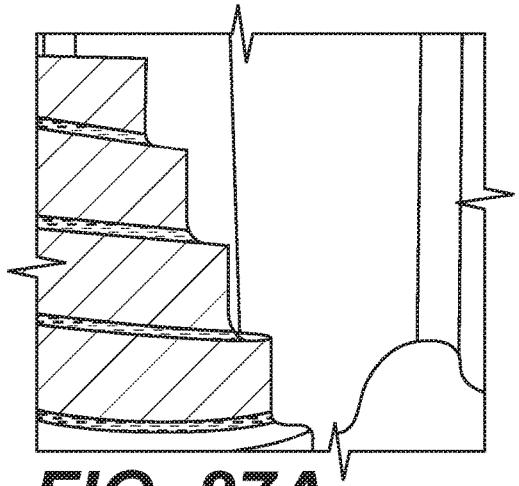
Figure 27B:
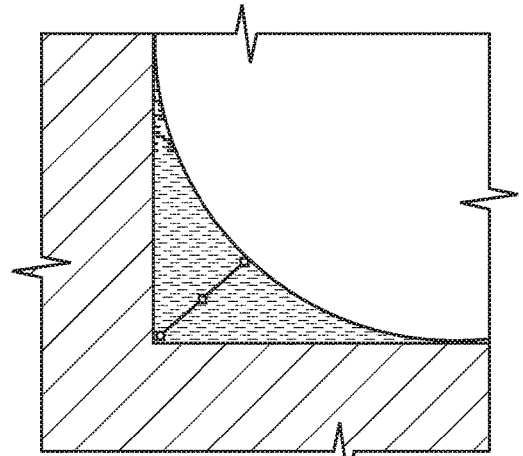
Figure 27C:
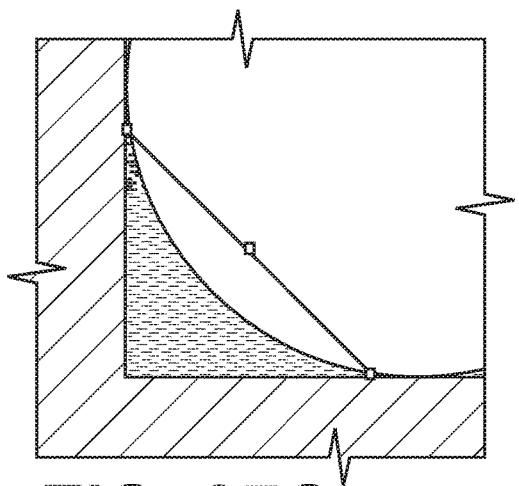
Figure 27D:
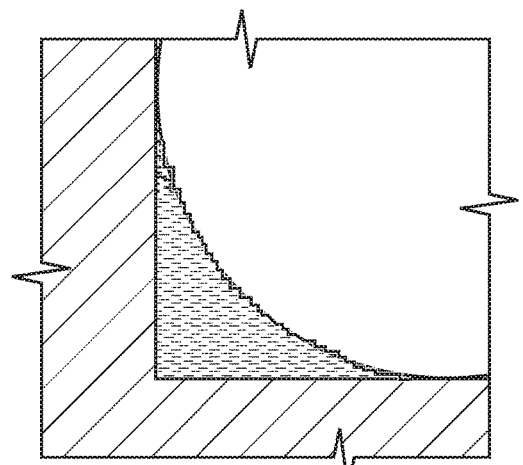

FIGS. 27A-27E are diagrams showing how the fluid profile in the exterior spiral oxygenator corner may be measured. The fluid profile in the oxygenator corner is imaged at the locations labeled A through D in FIG. 27E and measured using ImageJ software. In an image used to measure the profile at location B at 1 µL/s, a 1/16 in. drill bit in the plane of the profile is used for scale (FIG. 27A). The measurement h' is taken from the fluid surface to the corner obtained by extending the PSU edges, and then 0.2 mm is subtracted to account for the corner radius and obtain h (FIG. 27B). The value for w is measured two ways, first by a straight line (FIG. 27C). The value of w is also found by tracing the fluid interface with a freehand tool and measuring the path length (FIG. 27D). There is less than a 10% difference between the two methods, and it seems to have little effect on φ.

Figure 27E:
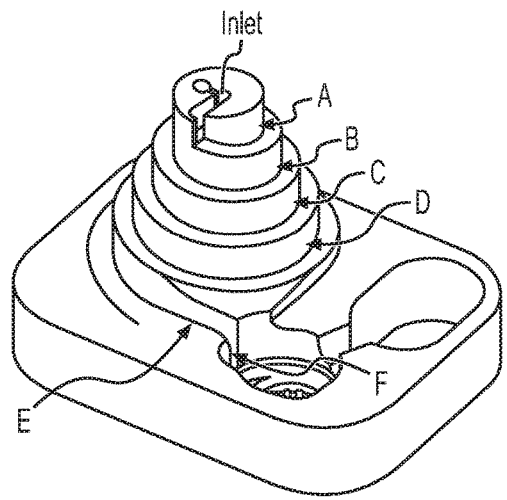
Figure 28:
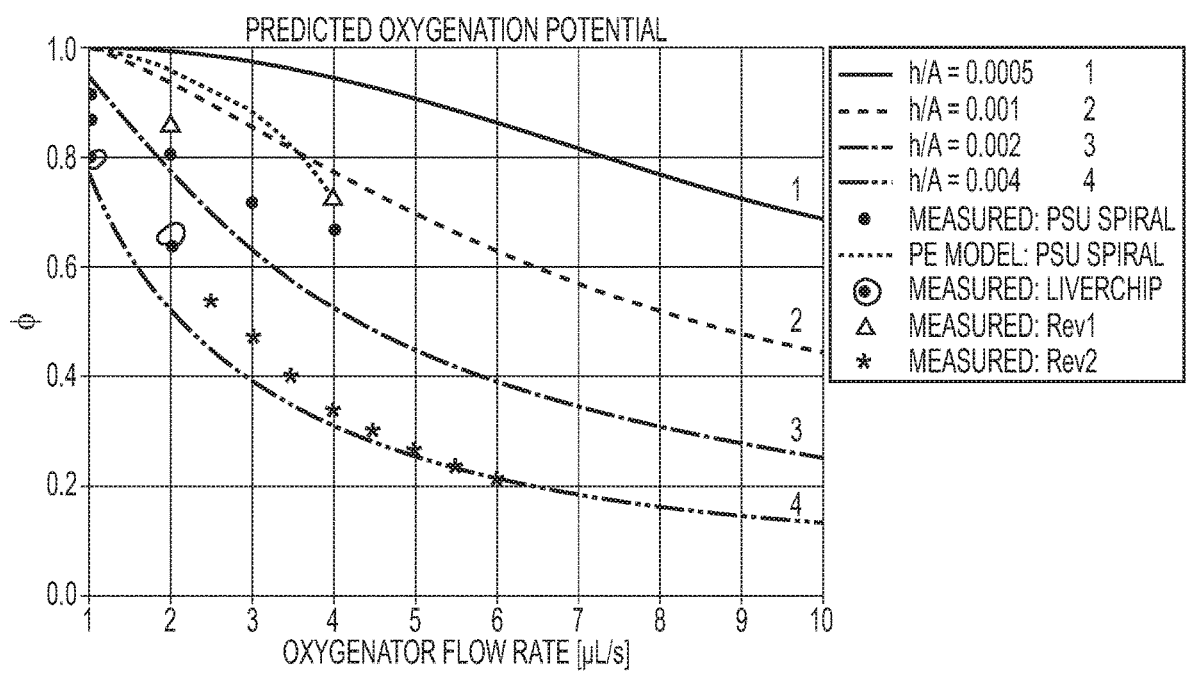

FIG. 28 is a graph showing the change in the predicted oxygenation potential (φ) with change in the oxygenator flow rate (µL/s) for different spiral oxygenators and different geometries of h/A (lines 1, 2, 3, and 4). The PSU spiral values were measured at position C shown in FIG. 27E.

Figure 29:
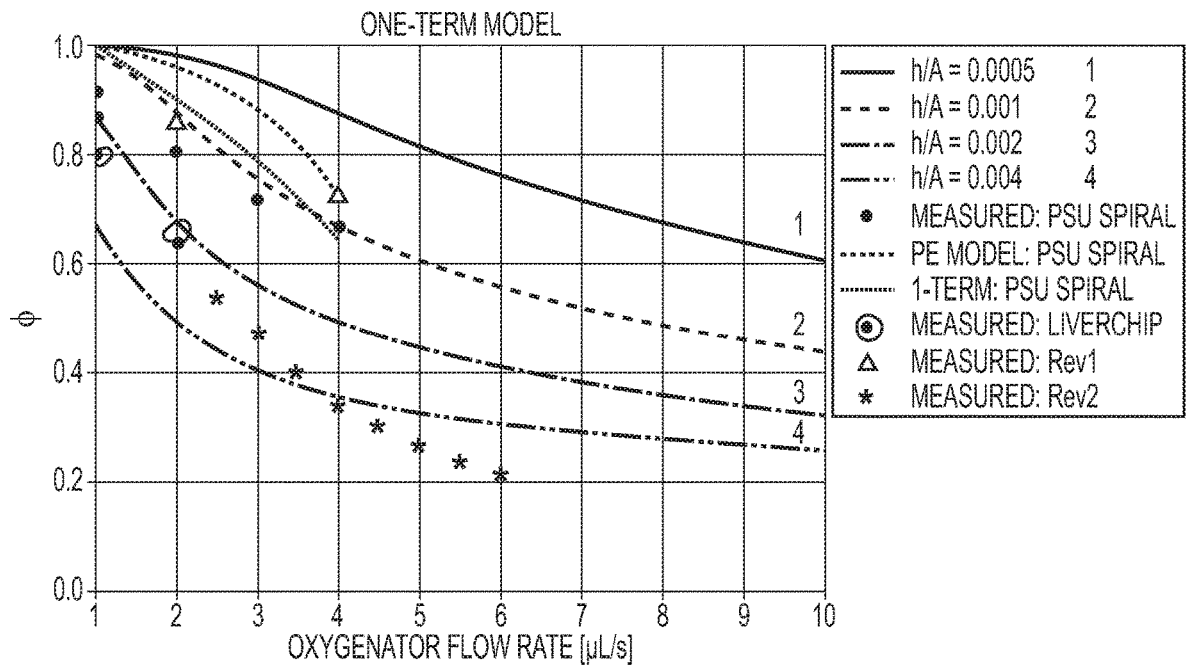

FIG. 29 is a graph showing the change oxygenation potential (φ) with change in the oxygenator flow rate (μL/s) for different spiral oxygenators as a one-term approximation model. The solid lines are calculated from equation 2.24 for various h/A values (lines 1, 2, 3, and 4), and the 1-term result is calculated from the same model using measured dimensions from the PSU spiral at location C, as shown in FIG. 27E. All other data are the same as in FIG. 28.

Figure 30:
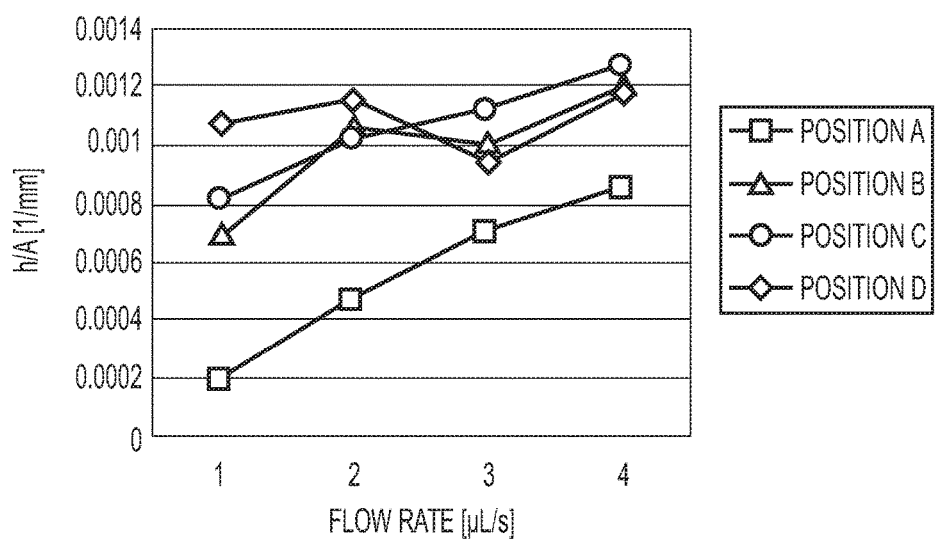

FIG. 30 is a line graph showing the change in geometric ratio h/A (1/mm) at different flow rates (μt/s) when measured at positions A, B, C, or D indicated in FIG. 27E. The geometric ratio h/A generally increased with increasing flowrate. The effect was significant at a greater height (position A), while negligible closer to the base of the spiral (position D). The h/A is generally smaller at the higher position, confirming that spiral height plays an indirect role in oxygenation potential φ.

FIG. 31 is a graph showing the change in oxygenation potential (φ) with change in oxygenator length (mm) for the SLA spiral and PSU spiral.

FIGS. 32A and 32B are diagrams showing the inline (FIG. 32A) and the mixed reactor (FIG. 32B) models. In inline model, the media leaving the oxygenator at $C_{high}$ feeds directly into the cells and re-enters the oxygenator at $C_{low}=C_{high}-r/Q$. In the mixed reactor model, the media exits the oxygenator at a high oxygen concentration $C_{out}$, mixes with bulk fluid volume to reach a mixed concentration C and media at concentration C then re-enters the oxygenator.

Figure 33:
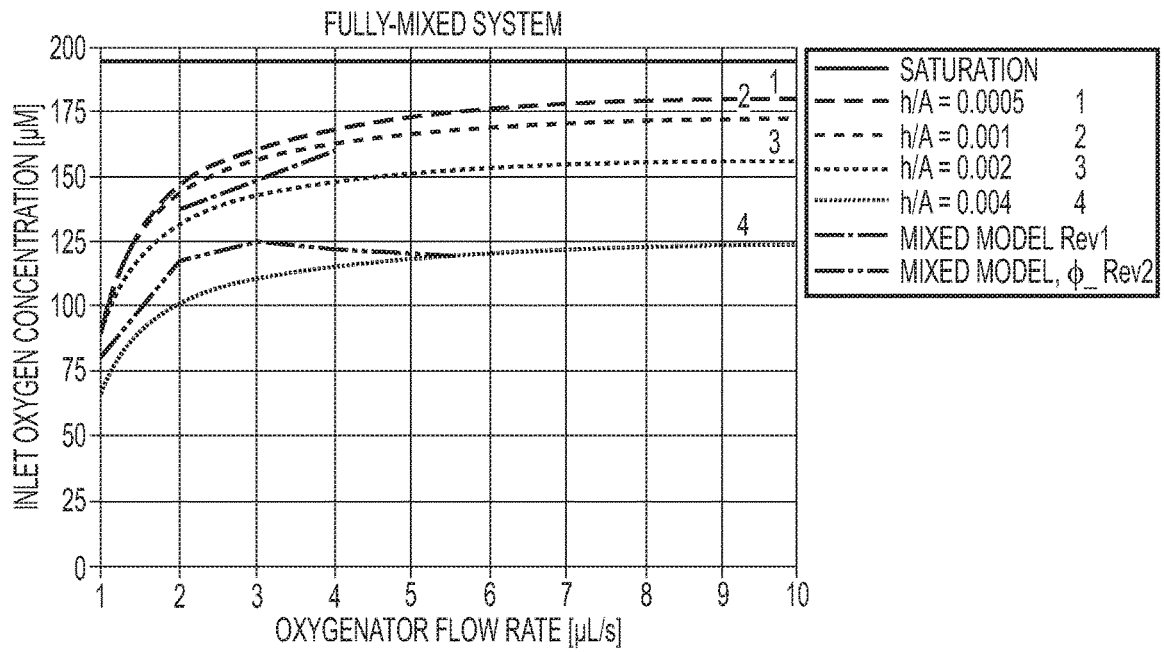

FIG. 33 is a line graph showing the inlet oxygen concentration (μM) at different oxygenator flow rates (μL/s) for mixed revision 1 and revision 2 models. Predicted steady-state bulk concentration for the mixed model, where cell consumption rate r=100 [pmol/s]. The saturated concentration is 195 μM (see Example 3). Predicted values for the revision 1 and 2 prototypes represent the measured values for the oxygenation potentials φ substituted into equation 3.5 (dashed lines). Note that because the consumption rate r is assumed to be fixed, this model can include non-physical negative concentrations.

Figure 34:
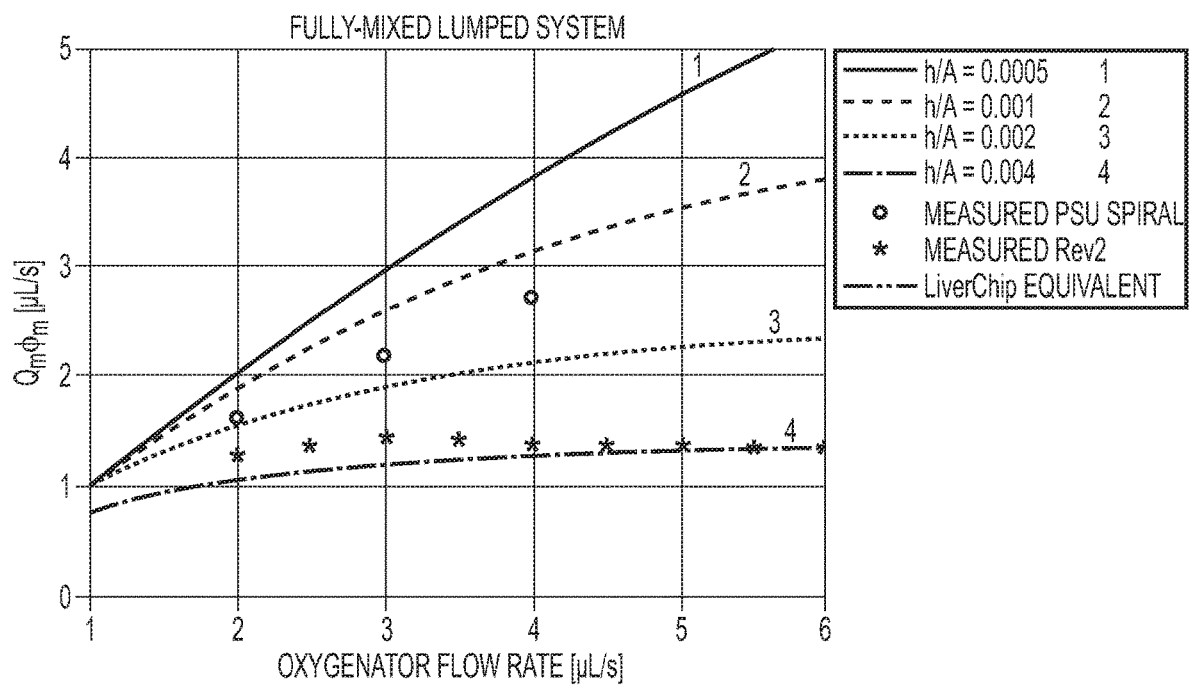

FIG. 34 is a line graph showing the flow rate of the system ($Q_m\varphi_m$ (μL/s)) with the change in the oxygenator flow rate at different oxygenator geometries. Based on the mixed reactor model approximation, the Rev2 oxygenator will not achieve the same steady state concentration going to the cells as the LIVERCHIP®. To do so, the mixed reactor model predicts a flow rate of 4 μL/s and h/A<0.0005 would come close to equivalency.

Figure 35A:
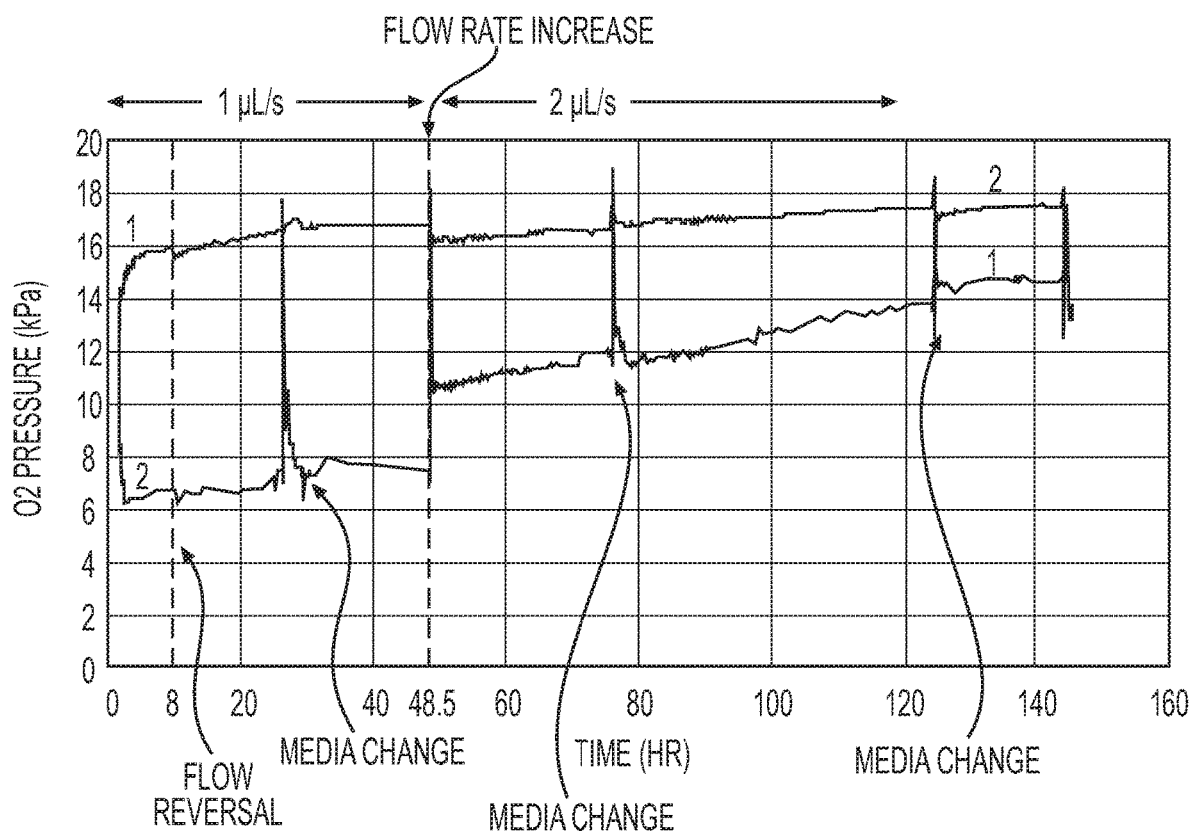
Figure 35B:
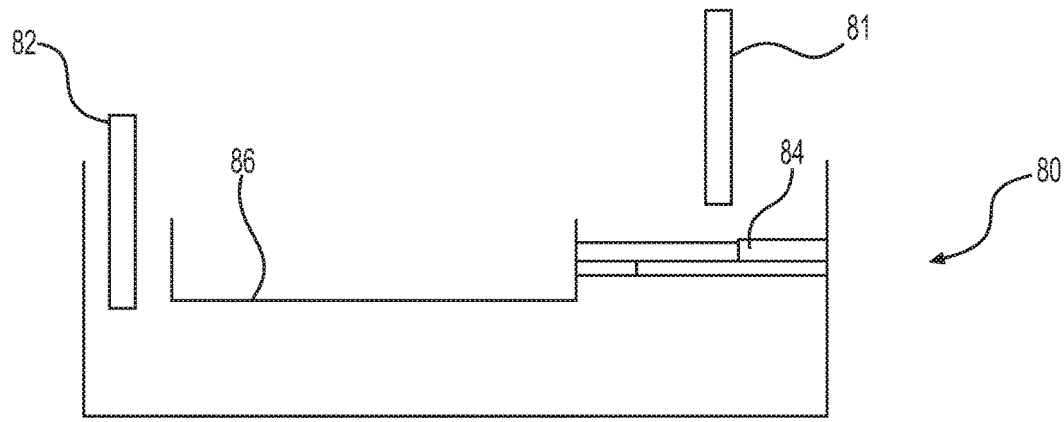

FIG. 35A is a line graph showing change in oxygen pressure (kPa) over time (hours) in one well of LIVERCHIP® platform at different flow rates. FIG. 35B is a diagram of an exemplary LIVERCHIP® platform 80, containing the scaffold 84 with cells, and oxygenation tail 86. An oxygen probe 81 is positioned in the well with scaffold 84, i.e., after the oxygenation tail, and provides readings for line 1 in FIG. 35A. Oxygen probe 82 is positioned before the oxygenation tail 86 and provides readings for line 2 in FIG. 35A. Oxygenation measurements were performed from one well of the LIVERCHIP® containing 250 000 rat hepatocytes. Flow was downward through the scaffold for the first 8 hours, then reversed to flow upward for the remainder of the experiment. After 48.5 hrs, the flow rate was increased to 2 μL/s.

Figure 36:
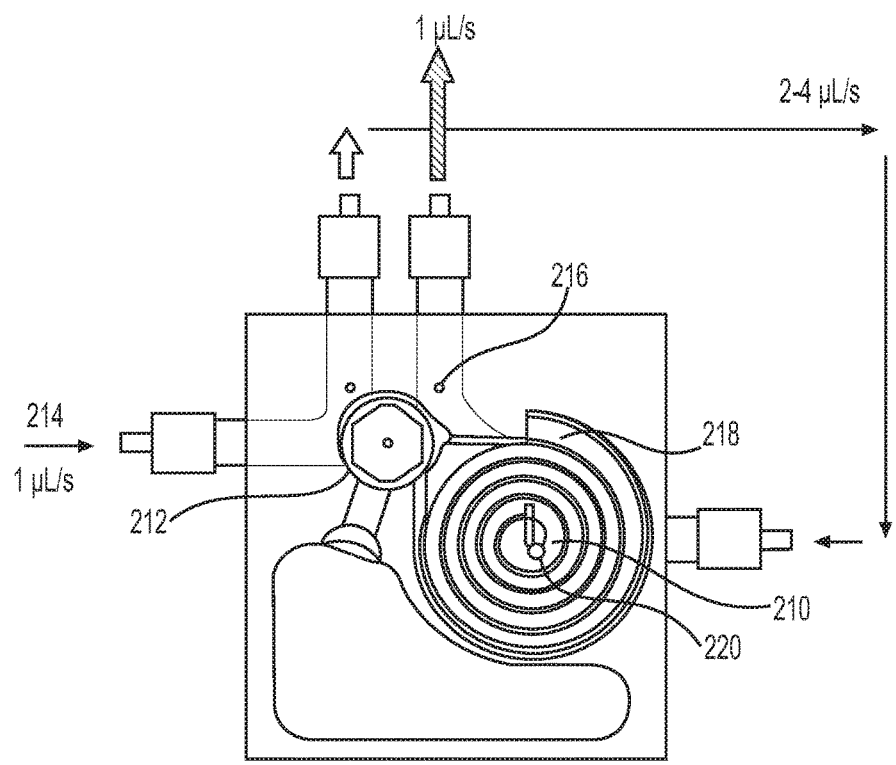

FIG. 36 is a diagram showing the top view of revision 1 oxygenator 210 and MPS well 212 with the fluidic connections. To simulate oxygen consumption, fluid is pumped out of the MPS (MPS out 216) and replenished with deoxygenated media (MPS In 214). In parallel, fluid is pumped from the MPS into the spiral oxygenator (Oxy In 220), where it flows into the MPS after the oxygen concentration is measured (Oxy out 218).

Figure 23:
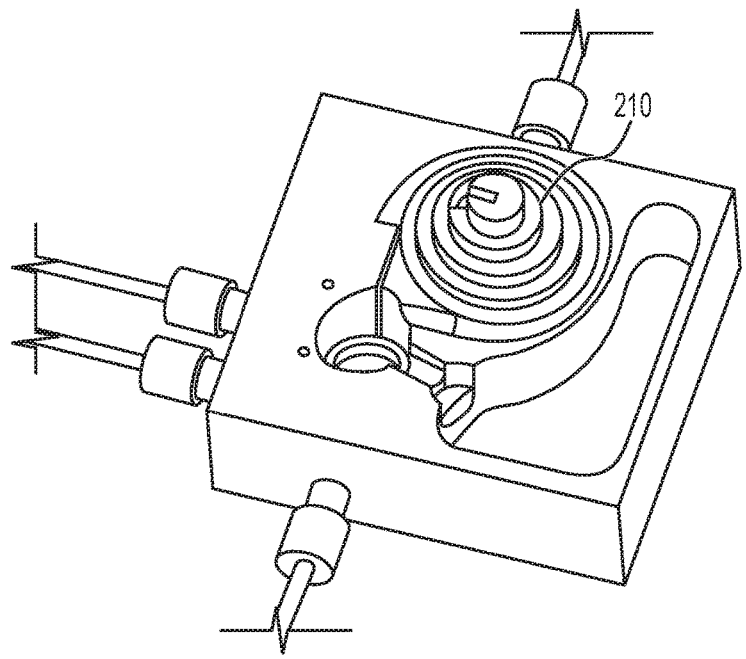
FIG. 23 is a diagram showing a perspective view of the Revision 1 spiral oxygenator 210, which is shorter than the original PSU spiral.
Figure 37:
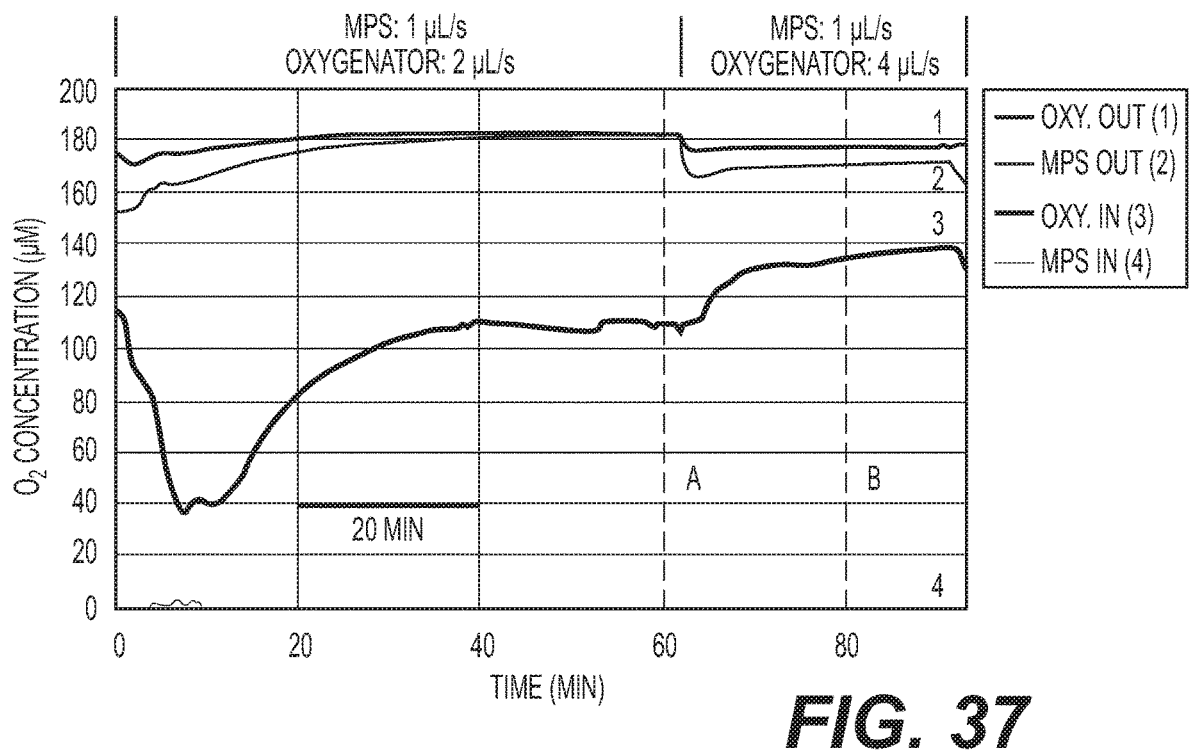

FIG. 37 is a line graph showing the change in oxygen concentration (μM) over time (min) for Revision 1 platform. Oxygen probe data were obtained from the Revision 1 platform shown in FIGS. 23 and 36. Shortly after time point A, the oxygenator flow rate was changed from 2 to 4 μL/s. In the incubator environment, oxygen saturation was at 195 μM (see Example 3).

Figure 38:
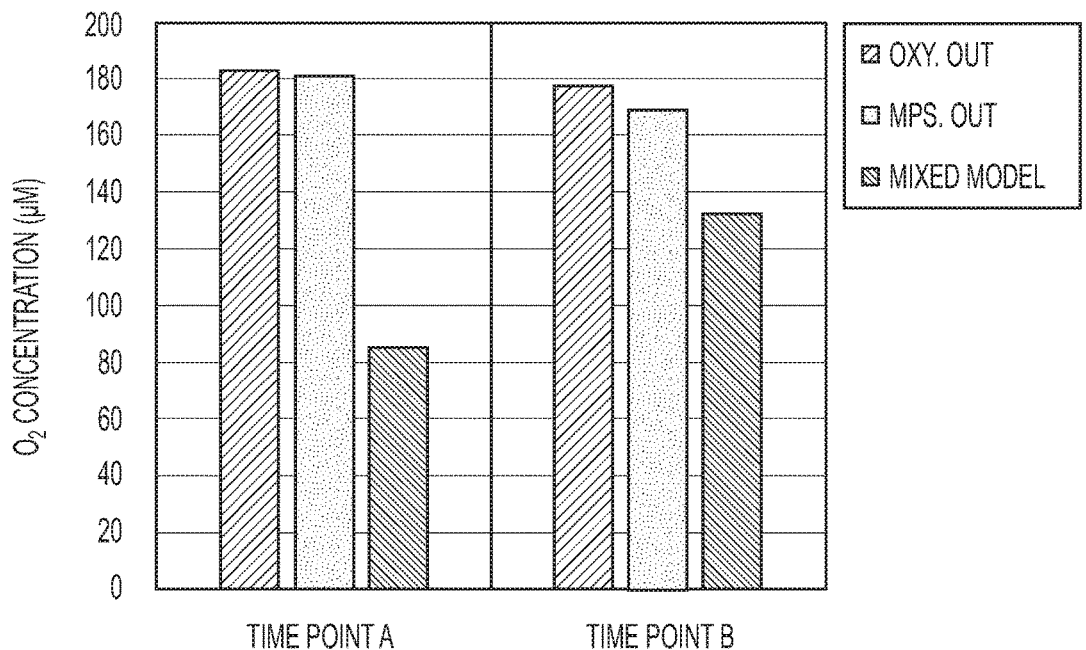

FIG. 38 is a bar graph showing oxygen concentration (μM) at time points A and B indicated in FIG. 37. Oxy.Out is the oxygenator output, which would go to the cells in an inline configuration. MPS Out is what goes to the cells in the selective sourcing configuration described. Concentration going to the cells in the mixed model is predicted from equation 3.5, where φ is calculated from the probe readings at the specified time point, and the simulated consumption rate r' is calculated from measured concentrations as $r'=Q_{MPS}(C_{MPS\ out}-C_{MPS\ in})$ in [pmol/s], where $Q_{MPS}$ is 1 [μL/s] and the concentrations are in [μM]. The mixed model underestimates the oxygen concentration relative to the experimental results.

Figure 39:
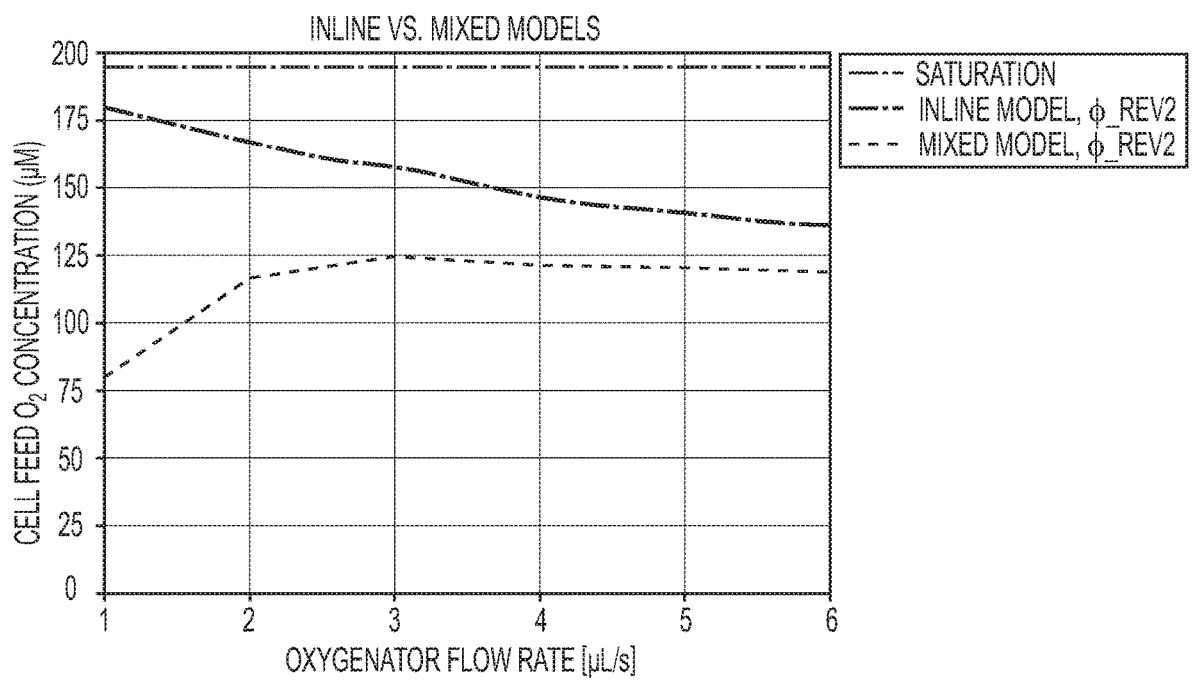

FIG. 39 is a line graph showing change in the cell feed oxygen concentration (μM) at different oxygen flow rates (μL/s) in inline versus mixed models. The oxygen concentration of media going to the cells for a fixed cell oxygen consumption rate r=100 pmol/s, predicted from measured revision 2 oxygenation potential data using the inline and mixed models (eqns. 3.6 and 3.7, respectively).

Figure 40C:
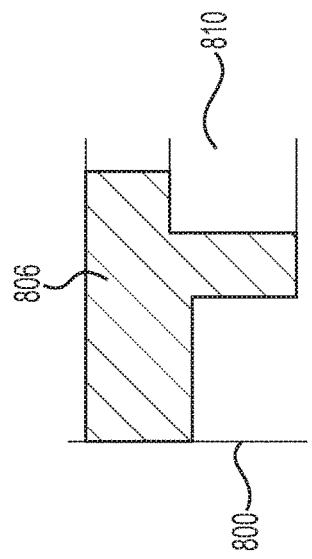
Figure 40B:
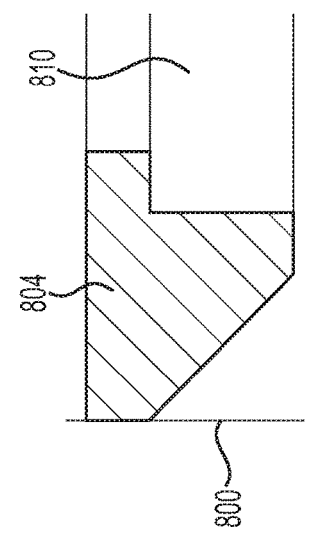
Figure 40A:
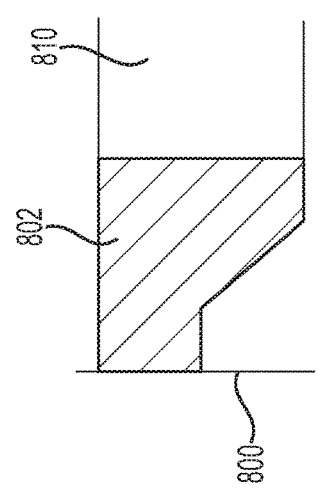
Figure 40D:
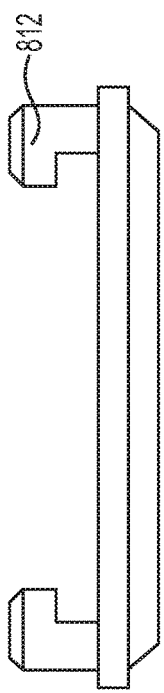
Figure 40G:
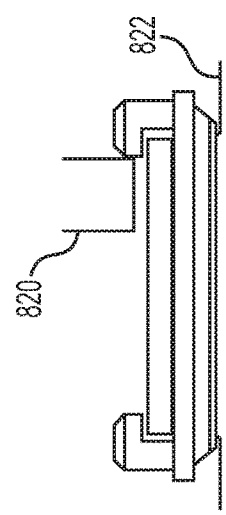
Figure 40F:
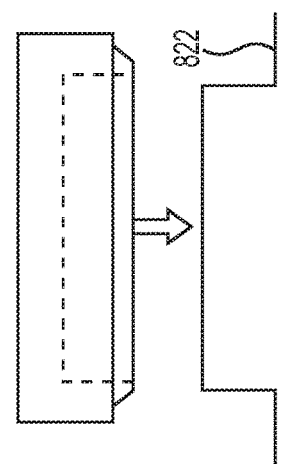
Figure 40E:
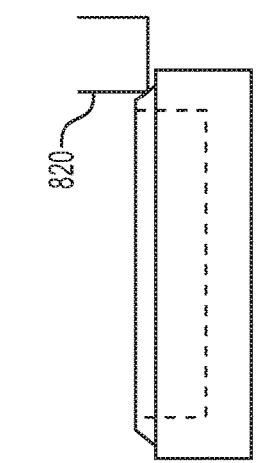

FIGS. 40A-40G are diagrams showing cross-sections of three main tilting-ring prototypes and their manufacture and installation. The tilting rings slanted profile 802 (FIG. 40A), triangular profile 804 (FIG. 40B), and T-shaped profile 806 (FIG. 40C) were tested for sealing. In FIGS. 40A-40C, the MPS wall 800 is to the left of the profile, and the ring center 810 is to the right. The slanted profile 802 sealed up to 25 kPa. The triangular profile 804 sealed up to only 5 kPa. The T-shaped profile 806 sealed up to 25 kPa. Removal clips 812 (FIG. 40D) were included on slanted profile 802, but not on triangular profile 804 or T-shaped profile 806. All prototypes were nominally 10.06 mm outer diameter and 1 mm tall. The fabrication process used for retaining ring prototypes with removal clips is presented in FIGS. 40E-40G. First, the bottom features were machined into a cylindrical blank using endmill 820, FIG. 40E. A locating post 822 was machined into sacrificial material, and the cylindrical blank was press-fit onto the post (FIG. 40F). With the center of the post known, the removal clips and other top features of the ring were machined (FIG. 40G).

Figure 41A:
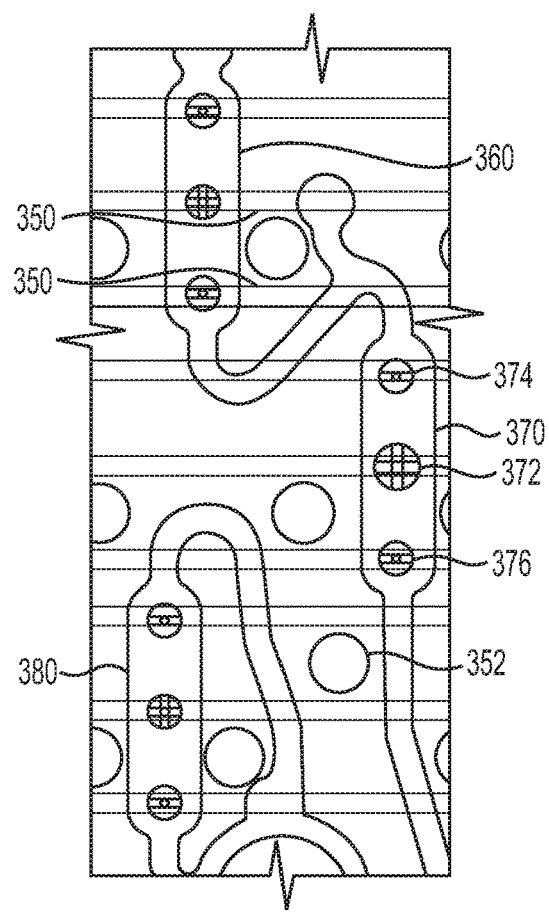
Figure 41B:
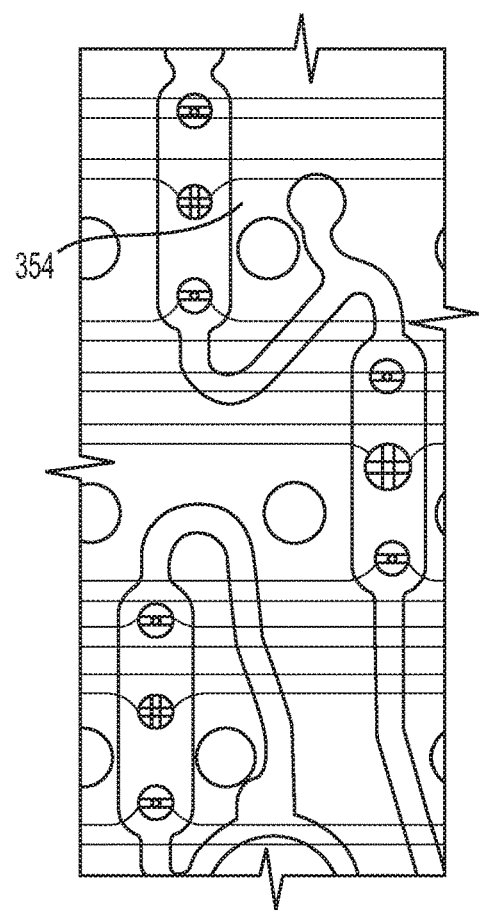
Figure 41C:
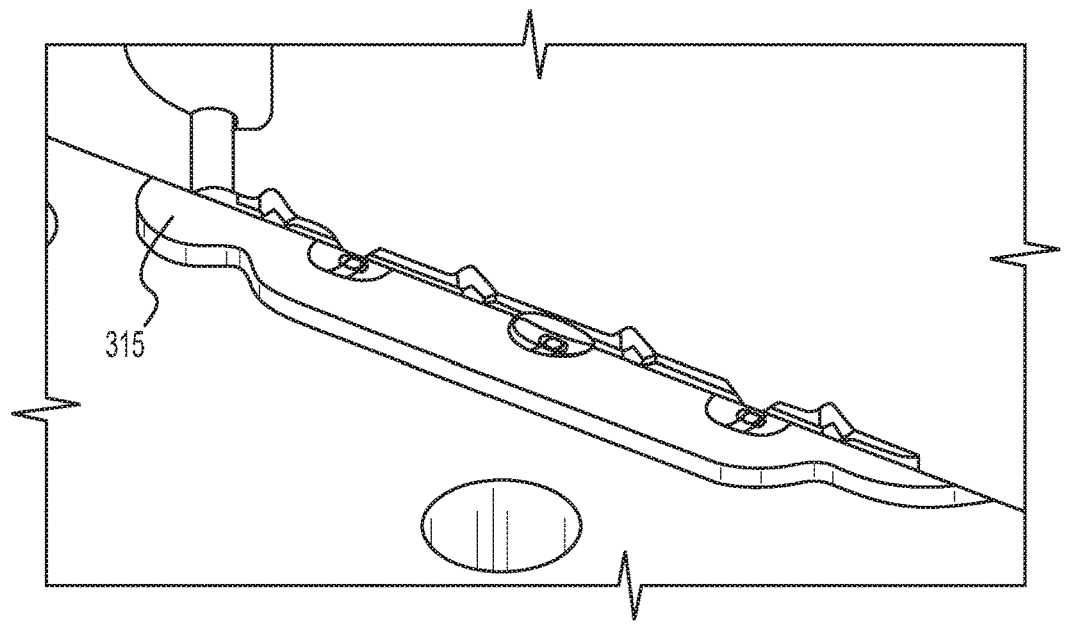

FIGS. 41A, 41B, and 41C are diagrams showing improvements on the pneumatic manifold with raised sealing land. The revision 2 pneumatic manifold with the thin wall 350 (470 μm thick, 1 mm tall) separating the channels and screw holes (FIG. 41A) was made more resilient by removing one set of screws 352 to allow a thicker wall 354 (2 mm wide, 1 mm tall). FIGS. 41A and 41B also show the arrangement of three diaphragm pumps 360, 370, and 380 per replicate lane. Taking the diaphragm pump 370 as an example, each pump includes a central pump chamber 372, and two valves 374 and 376, which allow bi-directional volume-determined flow. FIG. 41C shows a section of the diaphragm pump geometry. A central pump chamber and two valves allow for bi-directional volume-determined flow. A sealing land 315 seals around channels cut in the top plate to form the diaphragm pumps and fluid channels.

Figure 42:
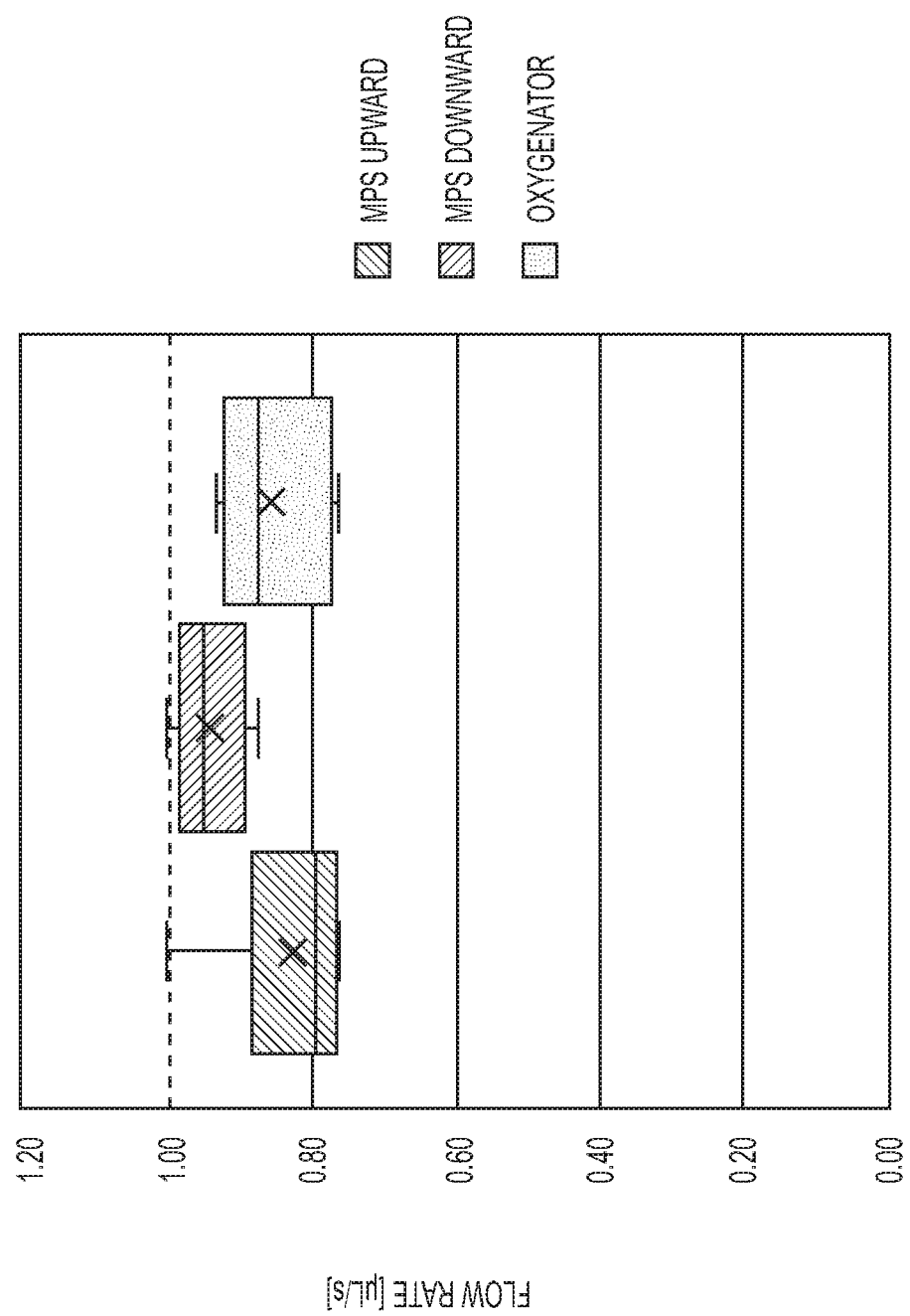

FIG. 42 is a graph showing the measured flow rate (μL/s) in MPS well and in the oxygenator. Measured flow rates, n=6: the MPS flow rate was measured in both directions, and the oxygenator was measured only in its forward operating direction. The intended flow rate was 1 μL/s.

DETAILED DESCRIPTION OF THE INVENTION

I. Definitions

As used herein, the term "platform" or "system" refer to interchangeably to organ-on-chip cell and tissue culture platforms.

As used herein, the term "reduced fluid volume", when used in relation to a platform, refers to a total circulating volume of 1000 μL and less. The total circulating volume is the volume of fluid circulating in the individual lane in the platform. It excludes volumes of fluid stored in the media reservoir and effluent reservoir. Platforms with reduced fluid volumes include platforms that operate with total circulating volumes of between about 50 μL and about 1000 μL, such as platforms that operate with total circulating volumes of 50 μL, 75 μL, 100 μL, 125 μL, 150 μL, 175 μL, 200 μL, 225 μL, 250 μL, 275 μL, 300 μL, 325 μL, 350 μL, 375 μL, 400 μL, 425 μL, 450 μL, 475 μL, 500 μL, 525 μL, 550 μL, 575 μL, 600 μL, 625 μL, 650 μL, 675 μL, 700 μL, 725 μL, 750 μL, 775 μL, 800 μL, 825 μL, 850 μL, 875 μL, 900 μL, 925 μL, 950 μL, 975 μL, and 1000 μL.

The term "pneumatic" refers to a system that uses air or vacuum pressure for operation.

The term "spillway" refers to a system of fluidic connections between a source well and a destination well for maintaining fluid levels in the source well.

The term "wetting" refers to the wetting of a solid surface by a liquid in a gas environment, which is determined by the minimum in Gibbs energy of the system. Wetting of a solid surface by a liquid in a gas environment results in an equilibrium contact angle φ across the liquid phase between the solid/liquid (SL) and liquid/gas (LG) interfaces as they emanate from the contact line. Generally the terms "wetting" and "nonwetting" surface refer to φ<90° and φ>90°, respectively. The relationship between the contact angle and the interfacial energies involved is expressed by Young's equation $\gamma_{SV} = \gamma_{SL} - \gamma \cos \phi$, where $\gamma_{SV}$, $\gamma_{SL}$, and $\gamma$ are the Gibbs interfacial energies between solid and gas, solid and liquid, and liquid and vapor, respectively, and where the last quantity is addressed as surface tension. To satisfy the thermodynamic equilibrium requirement, the gas phase is saturated with vapor.

The term "capillary length" refers to a characteristic length scale for an interface between two fluids which is subject both to gravitational acceleration and to a surface force due to surface tension at the interface. The capillary length may be measured at room temperature and pressure, and for pure water it has a value of $2.7 \times 10^{-3}$ m at 20° C.

As used herein, the terms "batch media exchange", or "batch exchange" refer to full removal and replacement of media in a replicate lane at one time.

The term "scaffold" in the relevant sections is an insert or component of the wells which provides support for tissue constructs.

As used herein, the term "cell seeding density" or "seeding density" represents a number of individual cells, as estimated according to standard cell counting protocols, at the time of seeding cells in a well, and for a short period of time thereafter, such as 1 hour, 2 hours, 3 hours, 4 hours, 5 hours, 6 hours, 7 hours, or 8 hours after seeding.

As used herein, the term "body" in the context of an oxygenator refers to an object of a three-dimensional shape. The body may be in a shape of a plane, a pyramid, a cone, a cylinder, a cube, a sphere, a rectangle, an oblong, a filament, a spiral, or an ovoid. The body may include additional features which add surface geometry, such as an interior corner, an exterior corner, a groove, a channel, a filament, gaps, surface modifications, surface roughness variations, and successive barriers, optionally wherein these alter surface tension. For example, an oxygenator with a body in a shape of a cone having interior corners cut into its outer walls may add surface geometry to the cone. The surface geometry may be in a form of an exterior spiral. The exterior spiral may form one or more steps on the conical body of the oxygenator.

As used herein, the term "absorption" refers to incorporation of compounds into the bulk of material, while "adsorption" refers to binding only at the surface.

As used herein, the term "hydrophobic surface" refers to a surface that repels water, such that water at 20° C. may have a contact angle of 90° or higher.

As used herein, the term "hydrophilic surface" refers to a surface that attracts water, such that water at 20° C. may have a contact angle of below 90°.

Recitation of ranges of values include the separate values falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%.

II. Organ-On-Chip Platforms with Reduced Fluid Volume

The platforms provide efficient oxygenation of cells and organs in culture with reduced fluid volumes. The platforms are typically cell- and drug-compatible, operate and fully oxygenate cells with total circulating volumes of between about 50 μL and 1000 μL, provide controlled fluid exchange, maintain fluid and system sterility during operation, integrate with existing standard tissue culture lids, and integrate with existing pneumatic infrastructure. In some embodiments, the platforms operate with existing pneumatic infrastructures, or pneumatic infrastructures disclosed herein.

The platforms may be open-well or closed fluidic systems. The open-well platforms are actively perfused cell culture systems capable of providing adequate oxygenation of cells in a circulating fluid volume between about 300 μL and 1000 μL. These systems are as open-well microphysiological systems (MPS).

The closed fluidic systems containing closed-well MPS without free surfaces. In the closed fluidic systems the volume is constrained and free of surface forces, and all constraints are fully wetted. The closed systems allow for adequate oxygenation of the same amount of cells as open-well systems, but with further reduced circulating volumes of fluid. Circulating volumes of less than 500 μL may be used in the closed fluidic systems.

The open-well systems culture cells in a manner that allows ready access to the cells, and has an unconstrained fluid-air interface. The closed-volume systems, by contrast, offer contained volumes that allow easier fluid handling, but access to the cells is often more difficult.

The systems typically include a fluidic plate and a pneumatic plate functionally coupled to each other and a membrane separating the fluidic plate from the pneumatic plate. In some embodiments, the pneumatic plate may be replaced with external pneumatic actuators, electro-mechanical actuators, syringe pumps, magnetic pumps, electromagnetic pumps, or any combination thereof. In other embodiments, the pneumatic plate may include electro-mechanical actuators, magnetic pumps, diaphragm pumps, electromagnetic pumps, or any combination thereof.

A. Fluidic Plate

A fluidic plate may include one or more replicate lanes. Typically, each replicate lane is configured to culture cells or tissue. Each replicate lane includes at least one oxygenator, an MPS well, a supply reservoir, and an effluent reservoir. Each lane may be coupled to one, two, three, four, five, or six pumps. Typically, the supply reservoir and the effluent reservoir are fluidically coupled with pumps for programmable media exchange. In some embodiments, three pumps per lane control media exchange, oxygenator flow rate, and the MPS low rate (perfusion rate through the scaffold), respectively. In some embodiments, a standard tissue culture lid may be used to cover the one or more lanes.

Typically, the oxygenator is fluidically coupled to at least one MPS well. The MPS well may include seeded cells. The MPS well may be a mixer well without seeded cells where the fluid from two or more organ wells combine for mixing, such as the mixer of modular organ MPS platforms. Exemplary MPS wells, mixer wells, and modular organ MPS platforms are described in U.S. Pat. No. 9,528,082 and U.S. Application Publication Nos. U.S. 2016/0377599 A1 and U.S. 2017/0227525 A1.

The number of replicate lanes per fluidic plate may be between one and six, between one and 12, or between one and 24. For example, the fluidic plate may include one, two, three, four, five, six, seven, eight, nine, then, 11, 12, 13, 14, 15, 16, 17, 18, 19, 20, 21, 22, 23, or 24 replicate lanes. Typically, when more than one replicate lane is present in a fluidic plate, the lanes are arranged horizontally in parallel, in tandem, or in any geometric position relative to one another on a horizontal plane.

At lower volumes, the depletion of nutrients by the cells and accumulation of waste products may become more significant, and batch media exchange (full removal and replacement of media at one time), may cause unwanted spikes in metabolic activity. Continuous or programmable media exchange may be desired to replace the media more frequently. In some embodiments, once-daily batch exchange of 500 µL would allow for replenishment of the media reservoir daily. Typical batch exchange volumes for the fluidic plates include about 50 µL, about 75 µL, about 100 µL, about 125 µL, about 150 µL, about 175 µL, about 200 µL, about 300 µL, about 400 µL, about 500 µL, about 600 µL, about 700 µL, about 800 µL, about 900 µL, or about 1000 µL.

Cell seeding and media exchange may be done in a sterile Biological Safety Cabinet (BSC) with standard precautions. The platform may need to be transported between incubator and BSC without contamination.

If no oxygen measurement is required, the platform may be formed to be compatible with standard pre-sterilized lids, such as the COSTAL® universal lid (Corning Product #3099). The platform may also be compatible with ⅛th inch OD pneumatic tubing and driven by the existing pneumatic controllers.

1. Open-Well MicroPhysiologial Systems

Figure 1:
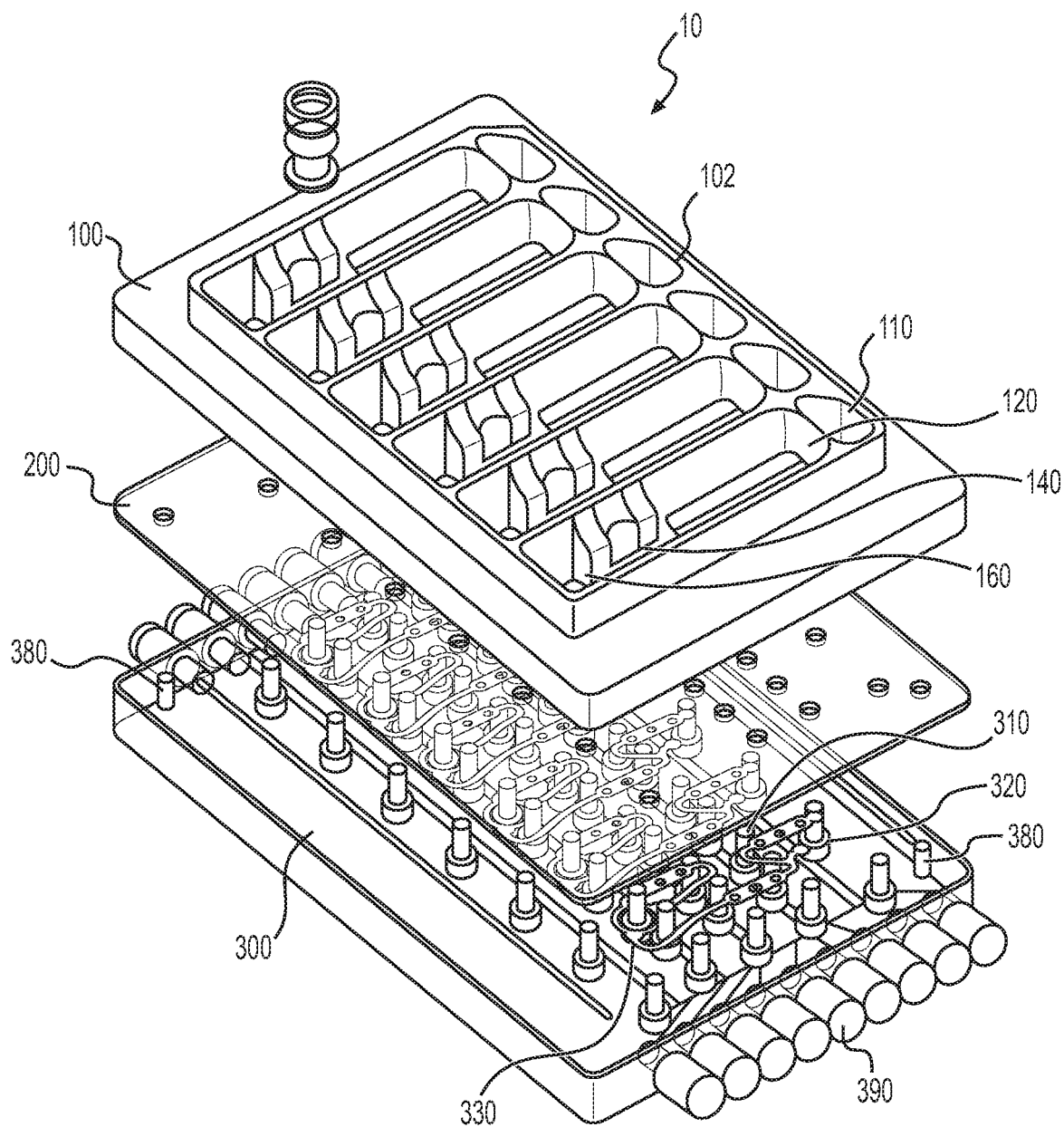
FIG. 1 is a diagram showing a perspective view of an organ-on-chip platform 10 with revision 2 oxygenator. The platform includes a fluidic top plate 100 (polysulfone) and a pneumatic bottom plate 300 (acrylic) separated by an elastomeric polyurethane membrane 200. Each of six replicate lanes 102 includes an elongated spiral oxygenator 120, an MPS well 140, and a media reservoir 110 and an effluent reservoir 160 for the programmable media exchange. Three diaphragm pumps 310, 320, and 330 per lane control media exchange, oxygenator flow rate, and the MPS flow rate (perfusion rate through the scaffold), respectively. The pneumatic channels are coupled across lanes, so the flow rates in each lane are nominally the same for a given one of the three functions. The pneumatic plate 300 include alignment pins 380 and pneumatic fittings 390. A standard tissue culture lid (not shown) covers the wells to reduce contamination risk.

FIG. 1 shows an exemplary organ-on-chip platform containing a fluidic top plate (polysulfone) and a pneumatic bottom plate (acrylic) separated by an elastomeric polyurethane membrane. Each of six replicate lanes includes an oxygenator spiral, an MPS well, and a supply and effluent reservoir for the programmable media exchange. In this embodiment, three diaphragm pumps per lane control media exchange, oxygenator flow rate, and the MPS flow rate (perfusion rate through the scaffold), respectively. The pneumatic channels are coupled across lanes, so the flow rates in each lane are nominally the same for a given one of the three functions. A standard tissue culture lid (not shown) covers the wells to reduce contamination risk.

Figure 2A:
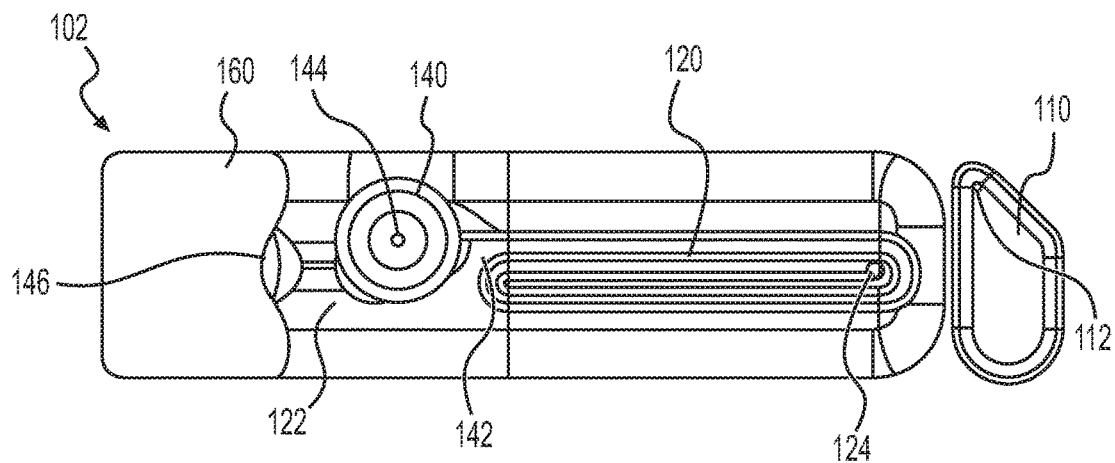
FIGS. 2A and 2B are diagrams showing a top view of a single replicate lane 102 and the corresponding connections with the pumps. The inlet and outlet holes in FIG. 2A correspond with the indicated sealing points on the pneumatic sealing land in FIG. 2B: media exchange inlet 112, start of the spiral 124, MPS inlet 142, MPS outlet 144, oxygenator inlet 122.
Figure 2B:
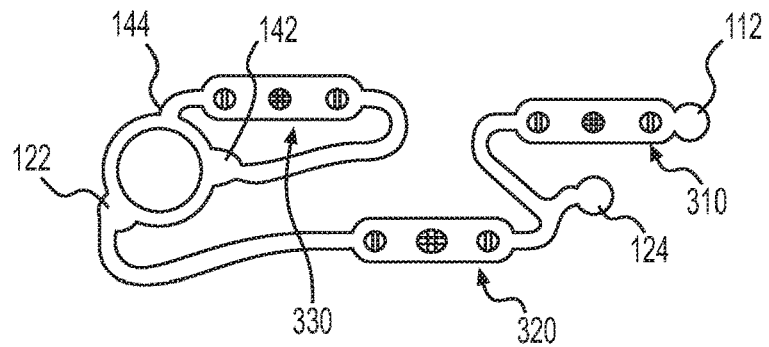

FIGS. 2A and 2B presents a top view of a single lane and its elements relative to sealing points on the pneumatic sealing land. The inlet and outlet holes (FIG. 2A) correspond to the indicated sealing points on the pneumatic sealing land (FIG. 2B).

2. Oxygenator

Typically, each replicate lane includes at least one oxygenator for oxygenating the circulating media.

Cell culture media may be oxygenated by methods broadly divided into two categories: 1) solid-liquid interface, such as membrane oxygenation, and 2) gas-liquid interface, such as culturing in a static dish or bubbling a gas through the liquid (sparging). Microcarriers that simulate the oxygen-storing capacity of hemoglobin in the blood may be included in the media (Tao, et al., *Trends in Biotechnology*, vol. 32, pp. 466-473 (2014); (Barbosa, et al., *Sao Paulo Medical Journal*, vol. 128, pp. 97-100 (2009)). While microcarriers allow greater oxygen storage density, the oxygen must still be replenished for long-term culture.

The standard approach for oxygenation of open-well static culture is by passive diffusion through an exposed surface. A culture lid increases sterility but allows oxygenation by overhanging the edge of the dish or well-plate; oxygen diffuses up the vertical air column, but bacteria, which sink in still air, are passively excluded. The primary factor affecting oxygenation is then the surface area of the air-medium interface relative to the depth of diffusion.

This passive interface oxygenation method has been used for open well systems with active circulation and mixing, as well as active perfusion through cell scaffolds (Domansky, et al., *Lab Chip*, no. 10, pp. 51-58 (2010)). The LIVERCHIP® platform uses a "tail," a shallow elongated channel that increases the exposed surface area, to provide oxygenation.

Several methods have been described to increase oxygen uptake in a free-surface cell culture environment, such as roller bottles, shakers, other agitation methods (Place, et al., *Free Radical Biology and Medicine*, vol. 113, pp. 311-322 (2017)), but these are not feasible options for very low fluid volumes. Sparging (bubbling gas through a reservoir of the fluid to be oxygenated) can increase gas-liquid surface area by introducing small bubbles, but this also requires a reservoir of medium and a method of containing the foaming that can be produced.

Figure 3:
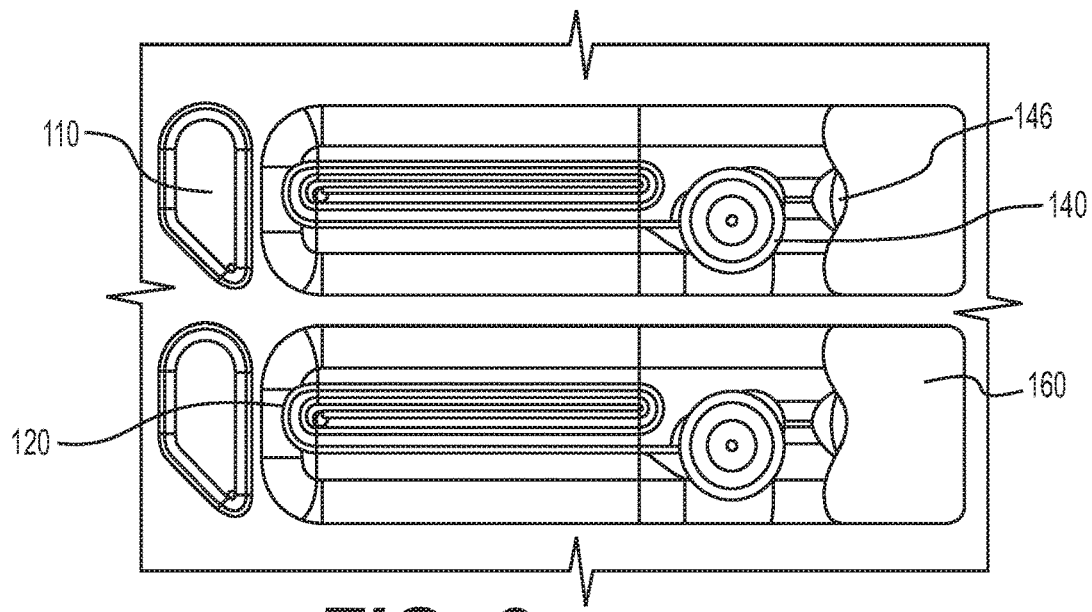
FIG. 3 is a diagram showing a top view of two replicate lanes with each lane having a revision 2 oxygenator 120 and fluid flow through the oxygenator. Fluid enters the oxygenator through the start of spiral 124 at left and flows counter-clockwise down a descending spiral through a channel formed by surface tension forces pulling fluid into a corner. The fluid spills via the spillway 146 over into the MPS well 140, and the continuous fluidic connection ensures a pressure drop ρgh that prevents fluid from accumulating in the oxygenator, and also serves to thin out the fluid profile, thereby decreasing diffusion depth and improving oxygenation.

Oxygenators oxygenate the media through a free airliquid interface while constraining the fluid path and limiting the volume that can collect in the oxygenator. In one embodiment, the oxygenator is a spiral oxygenator that captures the fluid in the corner of a spiral cut into hydrophilic polysulfone, as shown in FIG. 3. The corner serves to limit the maximum thickness of fluid that oxygen must diffuse into, and the spiral provides enough length in a small footprint for the fluid to exit the spiral adequately oxygenated.

a. Oxygenator Features

To oxygenate low volume fluids, the oxygenators typically have features permitting near saturation oxygenation of circulating fluids between about 300 µL and 1000 µL in volume. To achieve efficient oxygenation, the oxygenators typically have an oxygenation potential of about or over 0.8 after about one hour, two hours, three hours, four hours, five hours, six hours, seven hours, or eight hours of operation. The oxygenators remove air bubbles from the circulating fluid and provide bubble-free medium to the cultured cells in the MPS wells. Typically, the fluid continuously flows through oxygenators. The oxygenators do not store fluid so as not to deplete the cultured cells in the MPS wells.

Oxygenation Potential

Typically, the oxygenation potential of the oxygenators for low fluid volumes is between about 0.8 and 1, such as 0.8, 0.85, 0.9, 0.95, or 1, at flow rate of 1 µL/s. This oxygenation potential of the oxygenator is typically as good as, or better than, that of the LIVERCHIP® oxygenation channel.

The oxygenation potential φ, is defined as the change in oxygen concentration ($C_{high}-C_{low}$) across the oxygenator, normalized by the maximum possible change ($C_{sat}-C_{low}$):

$$\phi \equiv \frac{C_{high} - C_{low}}{C_{sat} - C_{low}} \quad \text{Equation 1}$$

Here, $C_{low}$ is the oxygen concentration at the oxygenator inlet, $C_{high}$ is the concentration at the outlet, and $C_{sat}$ is the fully saturated concentration. The parameter φ is a non-dimensional measure of oxygenator efficiency that varies from 0 to 1. φ is flow-rate dependent, but is independent of inlet concentration.

As described in the Examples, an experiment with 250,000 rat hepatocytes, the oxygenation potential of the LIVERCHIP® was determined to be 0.8 at 1 µL/s. During the initial eight hour cell seeding period, the oxygenators described herein typically have a Qφ≥4 µL/s, and have the φ≥0.8 after seeding.

Bubble Clearing

Gas bubbles trapped under the scaffold may cause cell death by displacing media and therefore starving the cells, and may also cause increased fluid shear stresses, as the same volume flow rate of liquid passes through a smaller area. To lower this risk, the media exiting the oxygenator is made bubble-free. The oxygenators typically clear bubbles during operation. The oxygenators are resistant to sloshing, and bubbles stay trapped at the top of the oxygenator without being passed on to the cell culture well. This is achieved with the design of the oxygenator and its elements, providing bubble-free oxygenated media to the cells.

Fluid Flow is Resumed without Depleting the MPS

Typically, the oxygenator operates continuously, but may be stopped for a brief period for experiments. During an experiment, the oxygenator may be stopped for between 1 and 10 minutes, between 1 and 8 minutes, between 1 and 6 minutes, between 1 and 5 minutes, between 1 and 4 minutes, between 1 and 3 minutes, between 1 and 2 minutes, or for less than one minute. In some embodiments, the oxygenator may not be stopped for more than approximately one minute. To maintain the cells in the oxygenated state, transportation of the platform between a site of storage, such as an incubator, and the bio-safety cabinet, where the experiment will be performed, should be brief. Both locations should have pumping capability. The cells' need for oxygen therefore limits the duration that the oxygenator may remain stagnant.

Volume-Limited

Typically, the oxygenator is configured to allow fluid flow through the oxygenator without storing or accumulating excess fluid volume. Therefore, the oxygenators avoid storing fluid volume so as not to deplete the MPS and risk cell death.

b. Oxygenator Geometries

The oxygenators typically contain a body with a three-dimensional shape. The body may include additional features which add surface geometry. The body of the oxygenator and its surface geometry are suitable for oxygenating low volume fluids.

The oxygenator may be integrated into the fluidic plate during plate manufacture, or mechanically attached to the plate.

The oxygenators may be membrane oxygenators, or oxygenators with a distinct three-dimensional shape. The distinct three-dimensional shapes may be any one of a pyramidal, conical, cuboid, spherical, rectangular, oblong, filamentous, or ovoid shape. The oxygenators with a distinct three-dimensional shape may include additional features carved into or attached to the shapes to improve oxygenation of low volume fluids. The additional features include interior corner, exterior corner, channel, filament, gaps in the oxygenator, surface modifications, successive barriers, and combinations thereof.

The additional features may be packaged onto the oxygenator body to provide a flow path for oxygenating low volume fluids.

Membrane Oxygenator

In one embodiment, the oxygenator is a membrane oxygenator. The membrane oxygenator may be used in closed systems, which use permeation of oxygen through a membrane interface that contains the fluid and separates it from an external environment.

The membrane may be flat, with shallow channels guiding fluid against it, or tubular, with fluid either inside or outside the tube. Cross-membrane and free-surface oxygenation approaches are limited by the effective diffusion distance and by the surface area of the interface. Membrane oxygenation is additionally limited by the rate of oxygen permeation through the membrane material, which must be biologically inert, non-sorptive of a wide range of drugs and biomarkers, non-permeable to liquid, and highly permeable to oxygen.

The thickness of membrane oxygenators may be between 10 µm and 500 µm, such as 10 µm, 20 µm, 30 µm, 40 µm, 50 µm, 60 µm, 70 µm, 80 µm, 90 µm, 100 µm, 125 µm, 150 µm, 175 µm, 200 µm, 250 µm, 300 µm, 350 µm, 400 µm, 450 µm, or 500 µm. Each replicate lane may include more than one membrane oxygenator, such as two, three, four, five, or six membrane oxygenators.

The membrane oxygenators may be formed of any material permeable to gases, such as oxygen. Suitable materials may be synthetic or biological polymers. Suitable materials include polyurethane (PU), polyethylene oxide (PEO), polybutylene terephthalate (PBT), polyether sulfone (PES), polyimide (PI) polymers, and block copolymers and asymmetric blends thereof. Exemplary materials for membrane oxygenator also include fluoroplastics, such as DuPont TEFLON® AF-2400 (Blackie, et al., *Membrane Oxygenation of Mammalian Cell Culture Fermenters Using Dupont*

Teflon AF-2400 Tubing, Dordrecht: Springer Netherlands, pp. 299-301 (2002)), or polyurethane, but the thickness required for pumping and sealing leads to very slow permeation. Pressurized air or pure oxygen may be used to accelerate oxygen permeation across a membrane.

Interior Corner

The interior corner geometric feature of the oxygenator (FIGS. 4A-4E) makes use of the tendency of a wetting fluid to pin to interior corners. Oxygenation with the interior corner takes advantage of this phenomenon to constrain the fluid in a predictable geometry, so that the oxygenator length can be designed deterministically to meet the system needs. One additional feature for predictable geometry is the downward slope of the flow path: the negative pressure pulls the fluid tightly into the corner, rather than expanding arbitrarily outward.

The interior corner may be packaged into a grooved switchback path carved into a downward sloping ramp. The interior corner may be packaged on a spiral ramp (FIGS. 5A-5C), allowing a long, continuous corner to fit in a more contained footprint.

The aim in making an efficient oxygenator is to decrease the diffusion path relative to the interface area. The diffusion length scale can be further reduced in this configuration by introducing a corner radius that is smaller than the fluid interface radius.

Spontaneous capillary flow (SCF), if not achieved by the contact angle and corner geometry alone, may be achieved through a narrow triangular groove such that the groove half-angle and the fluid contact angle sum to less than 90 degrees (Concus, et al., *Proceedings of the National Academy of Sciences of the United States of America*, vol. 63, no. 2, pp. 292-299 (1969)). As an alternative, the conditions for an SCF channel are described by Berthieret (Berthier, et al., *Microfluid Nanofluid*, no. 16, pp. 77-785 (2014)).

Figure 4A:
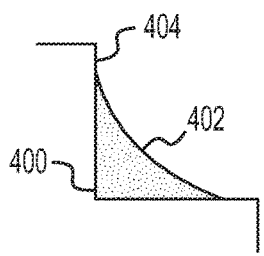
FIGS. 4A, 4B, 4C, 4D, and 4E are diagrams showing examples of interior corner geometries for oxygenators.
Figure 4B:
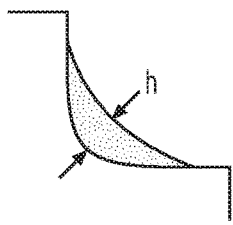
Figure 4C:
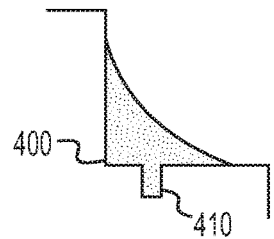
Figure 4D:
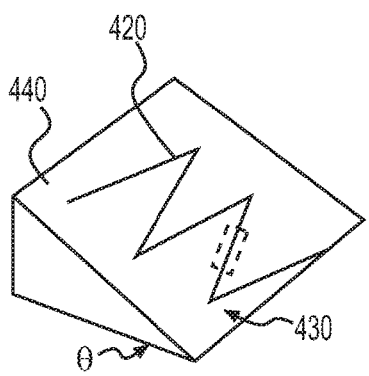
Figure 4E:
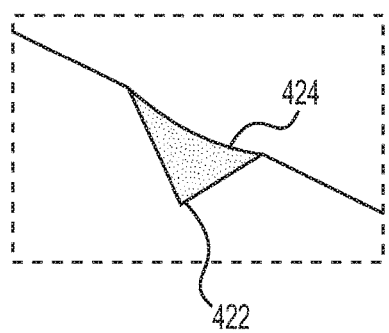

FIGS. 4A-4E show different geometries for an interior corner. As fluid 402 wets an interior corner 400 of a hydrophillic surface 404, surface tension thins the fluid into a curved profile, both limiting diffusion distance h and constraining the fluid path. FIGS. 4A and 4B show that a radius on the interior corner can reduce the effective diffusion length h even further. FIG. 4C shows a groove 410, which may be used with the interior corner 400 when the material is not sufficiently hydrophillic to fill spontaneously. The groove 410 causes spontaneous capillary flow (SCF), which aids rapid wetting of the full surface. FIG. 4D shows a path 420 with interior corner 422 cut into a downward sloping surface 440, ensuring that the oxygenator is self-emptying. For compact packaging, the path 420 may need to double back on itself with a switchback 430. FIG. 4E is an enlarged view of the interior corner 422 filled with fluid 424. The angle of the slope θ may be between 0° and 180°.

Figure 5A:
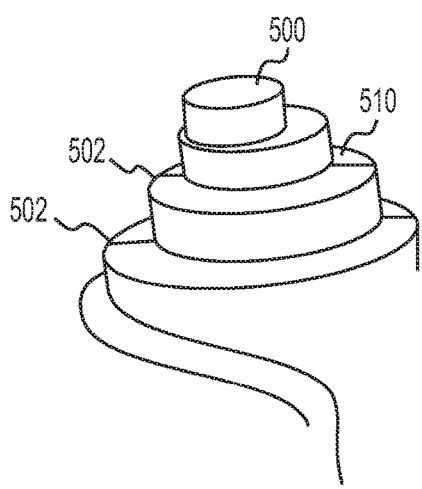
FIGS. 5A, 5B, and 5C are diagrams showing examples of packaging an interior corner in an oxygenator.
Figure 5B:
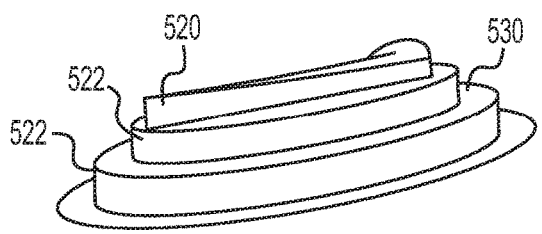
Figure 5C:
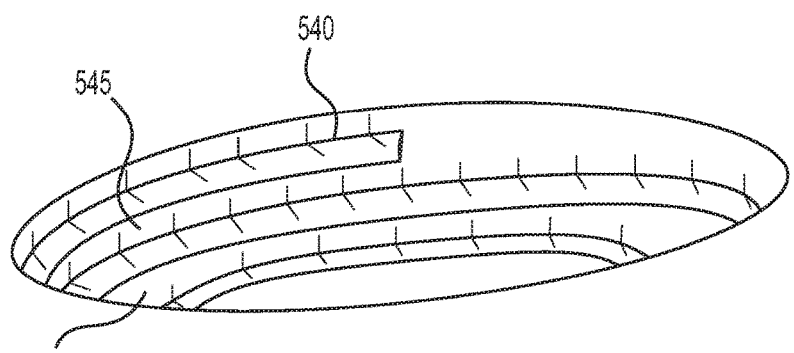

FIGS. 5A, 5B, and 5C are diagrams showing examples of packaging an interior corner in an oxygenator. FIG. 5A shows an interior corner 510 packaged into an exterior spiral on a conical body 500. The exterior spiral on the conical body 500 forms steps 502. An exterior spiral maintains fluid continuity, and a pressure drop from top to bottom keeps the fluid profile tight in the corner. FIG. 5B shows an interior corner 530 packaged into an exterior spiral on an elongated body 520. The exterior spiral on an elongated body 520 improves packaging. The exterior spiral on the elongated body 520 forms steps 522. FIG. 5C is a diagram of an interior corner 540 into an interior spiral, which forms steps 545.

Each oxygenator in the fluidic plate may include one or more interior corners, such as one, two, three, four, five, six, seven, eight, nine, ten, and more interior corners. The interior corner may be continuous along the length and/or height of the oxygenator. The interior corner may be discontinuous along the length and/or height of the oxygenator. In the spiral oxygenator with the at least one interior corner, the interior corner is continuous along the length and the height of the oxygenator.

A spiral oxygenator with the at least one interior corner may be a conical oxygenator containing a continuous spiraling interior corner along the outer circumference and the height of the oxygenator. The conical oxygenator with an interior corner may have a height between about 1 mm and about 20 mm, such as between 2 mm and 15 mm, or about 10 mm, and an exterior diameter at the base between about 2 mm and about 200 mm, such as between 5 mm and 150 mm, or between 10 mm and 100 mm.

A spiral oxygenator with the at least one interior corner may be an oblong oxygenator containing a continuous spiraling interior corner along the length and the height of the oxygenator. The oblong oxygenator with an interior corner may have a height between about 1 mm and about 20 mm, such as between 2 mm and 15 mm, or about 10 mm, and a length between about 2 mm and about 200 mm, such as between 5 mm and 150 mm, or between 10 mm and 100 mm.

The packaging of the interior corner into a continuous spiral forms steps on the body of the oxygenator. Therefore, oxygenators with interior corners may have one, but typically more than one, step along the height of the oxygenators. Oxygenators may include one, two, three, four, five, six, seven, eight, nine, ten, 11, or 12 steps along the height of the oxygenators. In preferred embodiments, the oxygenator is a conical or an elongated oxygenator with an interior corner forming an exterior spiral. In preferred embodiments, the oxygenator includes at least three steps along the height of the oxygenator. In preferred embodiments, the oxygenator geometry allows for a fluid path length between about 150 mm and 200 mm, such as about 175 mm, and a fluid profile having a width between 0.8 mm and 1.2 mm, such as about 1 mm, and a height between about 0.2 mm and about 0.5 mm.

Typically, the oxygenator with the at least one interior corner is machined into the platform itself with no crevices or interfaces requiring adhesive. This is a significant advantage for sterilization, cell compatibility, and usability. Further, this design is resistant to sloshing. Bubbles stay trapped at the top of the oxygenator without being passed on to the cell culture well.

Exterior Corner

The wetting fluid may be contained by a sharp edge (Oliver, et al., *Journal of Colloid and Interface science*, vol. 59, pp. 568-581 (May 1977), such as an exterior corner. The exterior corner may be used to create a fluid path suitable for oxygenation, as shown in FIGS. 6A-6D. One potential risk is spilling over the edge of the corner. This might be mitigated with an inverted configuration, where the fluid is suspended from a sharp-edged protrusion.

Typically, the exterior corner uses a sharp exterior edge to contain fluid expansion and guide it along an oxygenation path. As with the interior corner, a feature, such as a protrusion, may be introduced to the flow path to reduce the effective diffusion length. The exterior corner may also be inverted, suspending the flow from a guiding path on the lid.

Figure 6A:
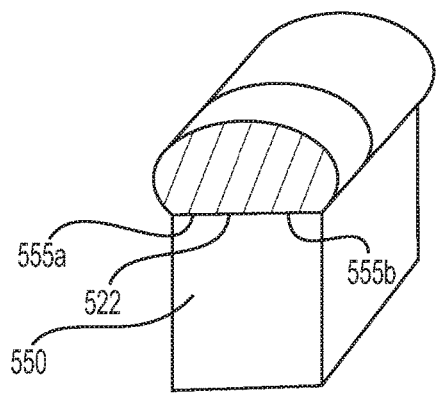
FIGS. 6A, 6B, 6C, and 6D are diagrams showing examples of an exterior corner.
Figure 6B:
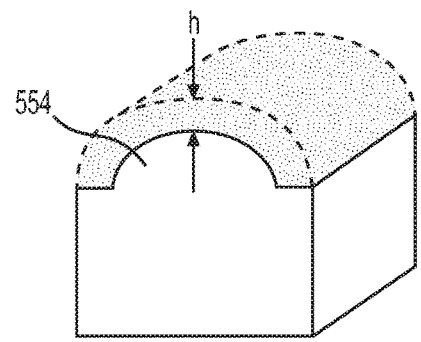
Figure 6C:
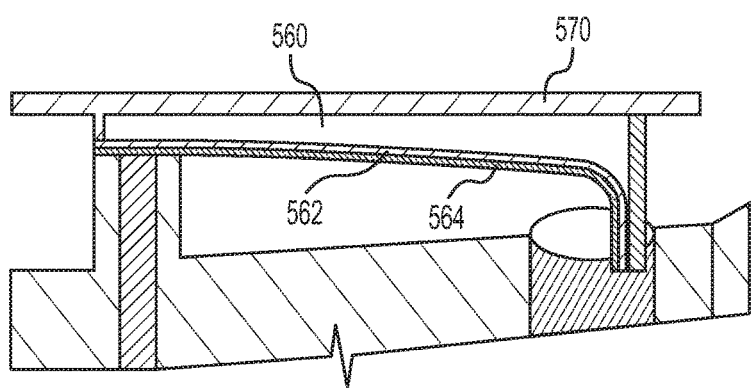
Figure 6D:
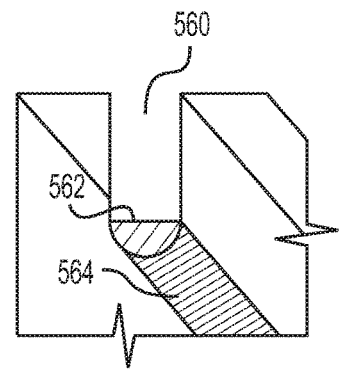

FIG. 6A shows an exterior corner 550 may use sharp exterior edges 555a and 555b to contain fluid expansion and guide it along an oxygenation path 552. FIG. 6B shows a feature, such as a protrusion 554, may be introduced to the oxygenation path to reduce the effective diffusion length h. FIG. 6C is a side view of an exterior corner 560 that is inverted, suspending the flow of fluid 564 from a guiding path 562 on the lid 570. FIG. 6D is a perspective view of an exterior corner 560 that is inverted, suspending the flow of fluid 564 from a guiding path 562.

Each oxygenator in the fluidic plate may include one or more exterior corners, such as one, two, three, four, five, six, seven, eight, nine, ten, and more exterior corners. The exterior corner may be continuous along the length and/or height of the oxygenator. The exterior corner may be discontinuous along the length and/or height of the oxygenator. In the spiral oxygenator with the at least one exterior corner, the exterior corner is continuous along the length and the height of the oxygenator.

A spiral oxygenator with the at least one exterior corner may be a conical oxygenator containing a continuous spiraling exterior corner along the exterior circumference and height of the oxygenator. The conical oxygenator with an exterior corner may have a height between about 1 mm and about 20 mm, such as between 2 mm and 15 mm, or about 10 mm, and an exterior diameter at the base between about 2 mm and about 50 mm, such as between 2 mm and 40 mm, or between 2 mm and 30 mm.

A spiral oxygenator with the at least one exterior corner may be an oblong oxygenator containing a continuous spiraling exterior corner along the length and the height of the oxygenator. The oblong oxygenator with an exterior corner may have a height between about 1 mm and about 20 mm, such as between 2 mm and 15 mm, or about 10 mm, and a length between about 2 mm and about 200 mm, such as between about 5 mm and about 150 mm, between about 10 mm and about 100 mm, or between about 2 mm and about 50 mm.

Channel

A long shallow channel may be used to oxygenate fluids at low volumes instead of interior or exterior corners. In this embodiment, the channel may not be much wider than the capillary length (between about 2 mm and 4 mm, or approximately 2.5 mm) or the fluid will separate and cling to the corners. The depth of the channel may vary and may be between about 2.5 mm and about 10 mm, such as about 2.5 mm, about 3 mm, about 4 mm, about 5 mm, about 6 mm, about 7 mm, about 8 mm, about 9 mm, or about 10 mm.

The height of fluid in the channel (and therefore diffusion length) may be difficult to define, especially if the fluid pins to the top edges of the channel.

The channel geometric feature uses a channel to guide the fluid flow. This channel could be spiraled around the interior of a well. The channel could snake back and forth down a ramp inclined anywhere from 0 degrees (flat) to 90 (vertical wall) to 180 (suspended upside-down).

Each oxygenator in the fluidic plate may include one or more channels, such as one, two, three, four, five, six, seven, eight, nine, ten, and more channels. The channel may be continuous along the length and/or height of the oxygenator. The channel may be discontinuous along the length and/or height of the oxygenator.

Filament

The fluid may be arranged to flow down a wetted filament, similar to condensation running down the exterior of slanted pipes and eventually dripping at a local minimum. A spiral filament may enable a more compact design relative to other embodiments. The filament may be formed into the desired geometry, and either removed for sterilization or disposed of after each use.

The filament geometric feature is similar to the inverted exterior corner. It uses the suspension of fluid from a feature to constrain the fluid path and provide oxygenation. The filament has the advantage of wrapping over itself in a spiral, allowing for tighter packaging. The filament cross section could be round, square, or angular. The surface area of the filament cross-section may be between about 1 $mm^3$ and about 20 $mm^3$.

Each oxygenator in the fluidic plate may include one or more filaments, such as one, two, three, four, five, six, seven, eight, nine, ten, and more filaments. The filaments may be continuous with an external diameter or width between about 0.01 mm and about 5 mm, and a length between about 0.01 mm and about 5 mm. In preferred embodiments, the external diameter or width is between about 0.1 mm and about 5 mm, such as between about 0.1 mm and about 4 mm, and a length between about 0.1 mm and about 5 mm, such as between about 0.1 mm and about 4 mm.

Gap-Spanning

In this embodiment, two filaments may be placed apart at a distance shorter than the capillary length, then the fluid paths may join to form a fluid bridge. This would increase further the exposed interface area relative to the diffusion depth for a given length of the oxygenator. The angle of each gap edge may be chosen with the contact angle of culture medium on that material in mind so as to make a fluid bridge energetically favorable.

The gap-spanning geometric feature typically contains two hydrophillic angled features with a gap between them. When fluid bridges this gap, the surface tension pulls it into a tight profile. The maximum diffusion distance h is further reduced by symmetry, if the fluid is oxygenated from both sides of the gap.

Each oxygenator in the fluidic plate may include one or more gaps, such as one, two, three, four, five, six, seven, eight, nine, ten, and more gaps. The width for the gaps may be between about 0.01 mm and about 5 mm. In preferred embodiments, the width of the gap is between about 0.1 mm and about 5 mm, such as between about 0.1 mm and about 4 mm, or between about 0.1 mm and about 2 mm.

Droplets

The diffusion length of oxygen through the culture media may be reduced by forming small droplets, which then drip into a collector and feed back into the cell culture well. To keep pace with the oxygen consumption of the cells, an array of multiple droplet sources may be used.

The droplets geometric feature relies on the short diffusion distance during the initial formation of a droplet. The maximum diffusion distance over time is the droplet radius. To maintain small droplets while allowing reasonable flow rates, an array of many droplet generating outlets may be used. An oxygenator with droplets may be an oxygenator with one or more, such as an array of, hollow tubes passing the fluid through. The fluid typically forms droplets at the end of the hollow tubes, which then drop on a collection vessel fluidically connected to the MPS well.

Surface Modification

In this embodiment, a barrier between hydrophillic and hydrophobic regions of a surface may be used for steering fluid in a long path. The barrier may be formed using surface modifications, and any length or shape of a path may be formed. Fluid may be constrained and guided by an interface between hydrophillic surface treatment and hydrophobic surface treatment.

An oxygenator with hydrophillic and hydrophobic regions may be formed with an additional surface treatment of the fluidic plate following fluidic plate manufacture.

Successive Barriers

In this embodiment, the fluid is limited to a very thin film in just a few regions along the fluid path. Doing so increases the overall oxygenation. This may be accomplished by introducing barriers between deeper segments. The barriers force a thin film over a distance shorter than the fluid capillary length, while the deeper segments provide stability to the overall flow path.

Oxygenators with successive barriers use the barriers to thin out the fluid profile along the fluid flow path, reducing diffusion distance at the barrier, while using intermediate reservoirs to stabilize the flow, since a thin film longer than the capillary length (between about 2 mm and about 4 mm) will not be stable.

Fluid Profile in the Oxygenator

Figure 24A:
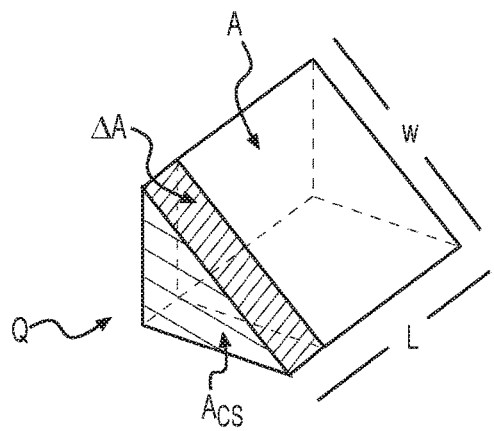
FIGS. 24A and 24B are diagrams of the plug flow model used for simplified oxygenator modeling.
Figure 24B:
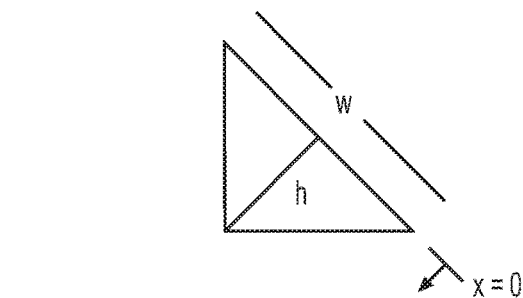

Typically, the fluid in the oxygenator follows a flow path with a particular fluid profile. The fluid profile may be the same or different along the same fluid path. The differences in fluid profile along the same fluid path may be due to the difference in height of the oxygenator, difference in length of the oxygenator, the presence of curves, turns, successive barriers, SCF channels, and other geometries along the fluid path. The fluid profile may be described by fluid height h, fluid width w and fluid length L at a particular location on the oxygenator (FIGS. 24A and 24B).

The values w and h for the fluids flowing through oxygenators described herein vary and may be for w between about 0.5 mm and 1.5 mm, such as 0.5 mm, 0.6 mm, 0.7 mm, 0.8 mm, 0.9 mm, 1 mm, 1.1 mm, 1.2 mm, 1.3 mm, 1.4 mm, or 1.5 mm, for h between about 0.2 and 1 mm, such as 0.2 mm, 0.3 mm, 0.4 mm, 0.5 mm, 0.6 mm, 0.7 mm, 0.8 mm, 0.9 mm, or 1 mm. Typically, the length L of the fluid path differs, and is dependent on the oxygenator geometry. Exemplary lengths for oxygenators vary between 50 mm and 500 mm, and may be 50 mm, 75 mm, 100 mm, 125 mm, 150 mm, 175 mm, 200 mm, 225 mm, 250 mm, 275 mm, 300 mm, 325 mm, 350 mm, 375 mm, 400 mm, 425 mm, 450 mm, 475 mm, or 500 mm.

For the same oxygenator, the values for w and h may vary and are dependent on the flow rate of the fluid as well as the position on the oxygenator at which the w and h are measured. For example, in an elongated external spiral oxygenator (revision 2 oxygenator) the h varies between 0.2 and 0.5 mm, the w varies between 0.8 and 1.2 mm, and the L is about 175 mm. With the variability in w, A too is variable, and is dependent on flow rate of the fluid as well as the position on the oxygenator at which the w is measured.

Exemplary flow rates for the oxygenators may be between about 0.005 µL/s and about 20 µL/s, such as between about 0.01 µL/s and about 18 µL/s, between about 0.1 µL/s and about 15 µL/s, between about 1 µL/s and about 10 µL/s, or between about 1 µL/s and about 6 µL/s.

c. Oxygenator Materials

Typically, the materials suitable for forming the oxygenators include the materials also suitable for forming the fluidic plate. Typically, the oxygenators are made of materials that do not substantially adsorb or absorb drugs, metabolites, or biomolecules. Suitable materials include polysulfone (PSU), TEFLON®/PTFE, polystyrene, cyclic olefin copolymer (COC), and stainless steel.

Suitable materials for membrane oxygenators include nano-porous polycarbonate (Wu, et al., Lab on a Chip, vol. 13, p. 2641 (2013)), micro-porous polypropylene or PTFE (Blackie, et al., *Membrane Oxygenation of Mammalian Cell Culture Fermenters Using Dupont Teflon AF*-2400 *Tubing*, pp. 299-301 (2002), or diffusive Dupont TEFLON® AF (Blackie, et al., *Membrane Oxygenation of Mammalian Cell Culture Fermenters Using Dupont Teflon AF*-2400 *Tubing*, pp. 299-301 (2002)), which are minimally interactive with small molecule drugs or biological molecules.

PDMS may be used for the bulk material, membrane material, or both (Lam, et al., *Transfucers and Eurosensors*, pp. 2489-2492 (2007); Volmer, et al., *Lab Chip*, pp. 1059-1066 (2005); Busek, et al., *Journal of Sensors and Sensor Systems*, vol. 5, pp. 221-228 (2016)). While its fabrication and gas transport properties are favorable, PDMS is limited in contexts where measurement or control of lipophilic drug, drug metabolite, or biomarker concentrations are important, as required in many MPS devices (Low, et al., *Clinical and Translational Science*, vol. 10, pp. 237-239)). These compounds both adsorb onto and absorb into PDMS, making the concentration in the local cell environment difficult to predict, measure, or interpret (Toepke, et al., *Lab on a Chip*, vol. 6, p. 1484 (2006)). Preferably, the platform described herein do not include PDMS.

d. Fluid Oxygen Concentration

Typically, the oxygen concentration of fluid delivered to the cells ranges between about 65 µM and about 400 µM, between about 65 µM and about 350 µM, between about 65 µM and about 300 µM, between about 65 µM and about 250 µM, or between about 65 µM and about 200 µM. Exemplary oxygen concentrations in fluids delivered to the cells in the MPS well may be about 100 µM, 125 µM, about 150 µM, about 175 µM, about 200 µM, about 225 µM, about 250 µM, about 275 µM, about 300 µM, about 325 µM, about 350 µM, about 375 µM, or about 400 µM.

3. Fluid Circulation

Any one of the embodiments of the oxygenator described above may be integrated with the MPS well to provide fluid oxygenation to the seeded cells. The fluid in the platform may follow different circulatory paths. An outline of an MPS well and its components is presented in FIGS. 7A-7D.

Typically, the fluid channel and pump arrangement determine the oxygen concentration of the media that is delivered to the cells. In preferred embodiments, the elements of the platform, such as the pumps, the oxygenator, the fluid channels, reservoirs, and the MPS wells are arranged such to: 1) provide reversible re-circulation flow through the scaffold; 2) circulate media at 150 µM $O_2$ or greater, with flow through the scaffold at 1 µL/s (MPS flow rate); and 3) couple pumps across replicate lanes.

Reversible re-circulation flow through the scaffold allows effective cell seeding and cell growth following cell attachment. When grown on the standard polystyrene scaffold, cells are "seeded" during the first 8 hours, during which media flows down through the scaffold. In this flow direction, the filter prevents cells from passing through, and they bind to the scaffold. After 8 hours, the flow is reversed and fluid flows up to prevent further accumulation of cells from clogging the scaffold channels. This upward flow continues for the duration of the experiment.

To meet the oxygen demand of cells with a high metabolic rate, such as hepatocytes, the system may circulate media at 150 µM 02 or greater, with flow through the scaffold at 1 µL/s (MPS flow rate). This oxygen concentration and flow rate are typically sufficient to grow between about $5 \times 10^4$ and about $10^7$ cells per MPS well with oxygen consumption rate of approximately 100 pmol/s. For example the oxygen concentration is typically sufficient to grow $5 \times 10^4$, $10 \times 10^4$, $20 \times 10^4$, $30 \times 10^4$, $40 \times 10^4$, $50 \times 10^4$, $60 \times 10^4$, $70 \times 10^4$, $80 \times 10^4$, $90 \times 10^4$, $100 \times 10^4$, and up to $1000 \times 10^4$ cells per MPS well, as about 250 000 rat hepatocytes or 600 000 human hepatocytes per MPS well. A 150 µM oxygen concentration may be a target minimum, but the range of acceptable values may be between about 50 μM and about 400 μM, such as between about 100 μM and about 200 μM. As a comparison, blood oxygen concentration is approximately 150 μM in the arteries and closer to 65 μM in the portal vein, which feeds into the liver (Tygstrup, et al., *Journal of Clinical Investigation*, vol. 41, pp. 447-454 (1962)). As hemoglobin is storing additional oxygen in the blood, cell culture media may be oxygenated to higher concentrations than these to deliver the same total amount of oxygen.

Typically, when more than one replicate lane is present in the system, each pump is coupled across replicate lanes. The pneumatic architecture controls one pumping degree of freedom (DOF) with three pressure/vacuum tubes (controlling one pump chamber and two valves). To reduce complexity of the set-up, each pump function (e.g. re-circulation, oxygenation, or media exchange) that is consistent across replicates may be controlled by a single pneumatic DOF, which includes one three-tube cluster. The flow rate may be varied over time on the same platform, or multiple platforms may be used; and more than one replicate lane on a platform may be desired. Therefore, platforms with parallel flow rates across replicates in a single platform are provided.

In some embodiments of the open-well systems, the flow circulation configuration operates with the circulating volume of about 500 μL, and may follow the circulation layouts selected from the group consisting of in-line circulation, co-flow circulation, counter-flow circulation, laminar Figure-8 circulation, and selective sourcing.

a. In-Line Circulation

The inline configuration (FIGS. 8A and 8B) is the simplest, it is used on the existing LIVERCHIP® platform, and is presented here for a comparison. The media flows in a single loop, with the cells consuming oxygen and the oxygenator replenishing it. The oxygenator flow rate is therefore the same as the cell perfusion flow rate. The inline circulation of the LIVERCHIP® platform uses an oxygenator consisting of a wide channel with enough exposed surface area to oxygenate the media as it travels back to the MPS.

Figure 8A:
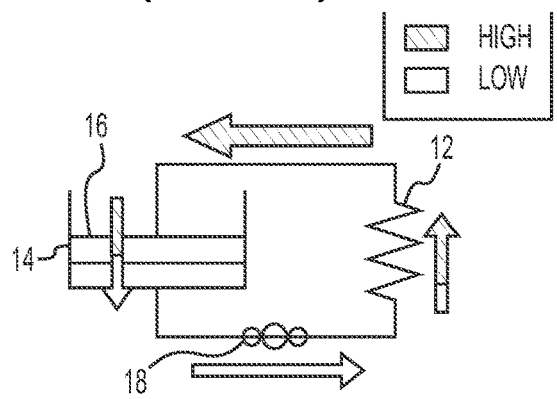
FIGS. 8A and 8B are diagrams showing inline configuration for fluid flow through a platform.
Figure 8B:
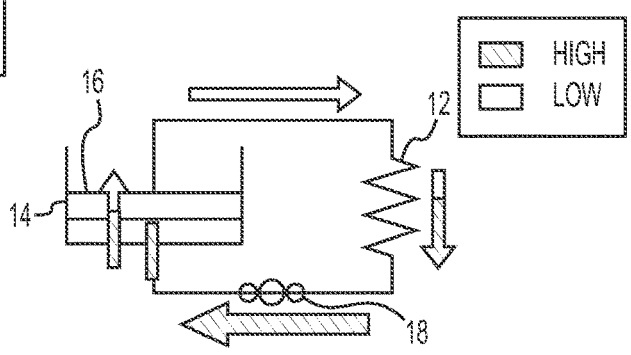

FIGS. 8A and 8B are diagrams showing inline configuration for fluid flow through a platform: the oxygenator 12 is on the same flow circuit as the MPS well 14 and cells 16 seeded on a scaffold. The flow is downward (FIG. 8A) for the first 8 hours to help the cells seed on the scaffold. After 8 hours, the flow reverses (FIG. 8B). This configuration requires a reversible oxygenator. Pump 18 direct the flow of fluid. High oxygenation level is shown with diagonal patterning, and low oxygenation level is shown in solid color.

Because the cell culture protocol requires reversing flow after the first 8 hours, the oxygenator needs to function in both directions, which precludes the use of a down-hill self-clearing oxygenator. An active flow path switching mechanism allows the use of a one-direction oxygenator, but introduces additional complexity and circulating volume.

b. Co-Flow

The co-flow configuration (FIGS. 9A and 9B) decouples the oxygenator from the MPS recirculation flow circuit. This allows a unidirectional oxygenator. When flowing downward, if the flow rates are equal, the system behaves like an inline system, and the cells are exposed to the highest saturation media in the system. When flow is upward, the cells are exposed to a mix of oxygenated media from the oxygenator and deoxygenated media from the MPS outlet. This results in the cells being exposed to a lower oxygen concentration for a given oxygenator efficiency than in an inline system.

Figure 9A:
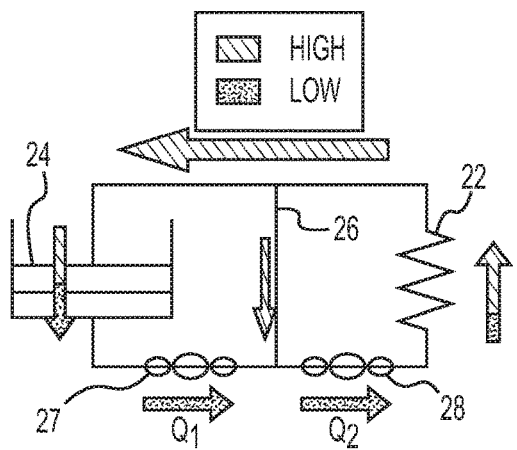
FIGS. 9A and 9B are diagrams showing co-flow configuration for fluid flow through a platform.
Figure 9B:
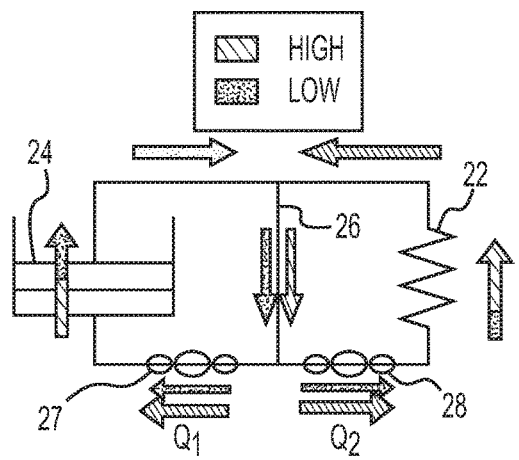

FIGS. 9A and 9B are diagrams showing co-flow configuration for fluid flow through a platform. FIG. 9A shows that during seeding, mixed oxygen concentration media enters the oxygenator 22, and high oxygen concentration media is fed to the cells 24. The small flow down the central channel 26 assumes that the flow rate $Q_2$ of the pump 28 is only slightly greater than the flow rate $Q_1$ of the pump 27. FIG. 9B shows that after seeding, mixed media is fed to cells 24 and to the oxygenator 22. $Q_2$ is in the same direction in both flow conditions, so a unidirectional oxygenator may be used. Pumps 27 and 28 direct the flow of fluid. High oxygenation level is shown with diagonal patterning, and low oxygenation level is shown in solid color.

c. Counter-Flow

The counter-flow configuration (FIGS. 10A and 10B) is similar to co-flow, but the cells are exposed to the high-concentration media during upward flow, rather than downward flow. This is advantageous, since in a typical experiment, the exposure to the lower concentration mixed media is limited to the first 8 hours of a multi-day experiment Like co-flow, counter-flow allows a unidirectional oxygenator. If the oxygenator flows downhill and is not a closed system capable of suction, the pump is typically positioned before the oxygenator.

Figure 10A:
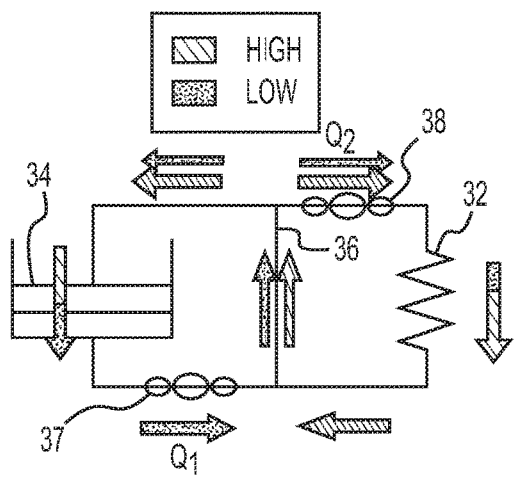
FIGS. 10A and 10B are diagrams showing counter-flow configuration for fluid flow through a platform.
Figure 10B:
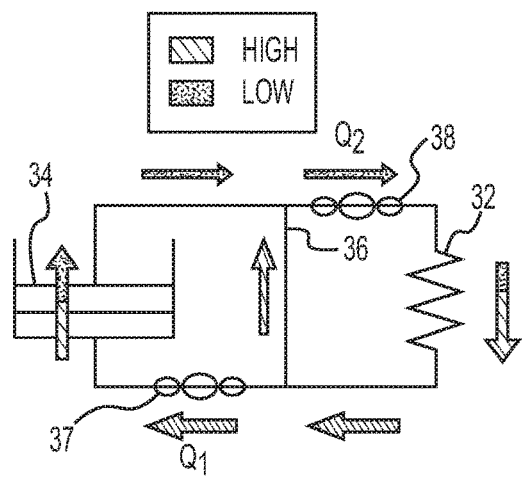

FIGS. 10A and 10B are diagrams showing counter-flow configuration for fluid flow through a platform. FIG. 10A shows that during seeding, mixed concentration media enters the cells 34 and oxygenator 32. FIG. 10B shows that after seeding, high concentration media is fed to cells 34. Pumps 37 and 38 direct the flow of fluid, including through the central channel 36. High oxygenation level is shown with diagonal patterning, and low oxygenation level is shown in solid color.

d. Laminar Figure-8 Flow

In this configuration (FIGS. 11A and 11B), the fluid circulation attempts to combine the strengths of the co- and counter-flow designs, so that the cells are exposed to high concentration media, but the oxygenator does not need to be reversible. During downward flow, the system behaves like an inline system if the oxygenator and recirculation flow rates are the same, feeding high concentration media to the cells. During upward flow, the short laminar section attempts to limit mixing, separating the flow paths into a high concentration stream for the cells and a low concentration stream for the oxygenator. This circulation loop may be manufactured with additional design considerations, and may require an additional volume compared to the other systems.

Figure 11A:
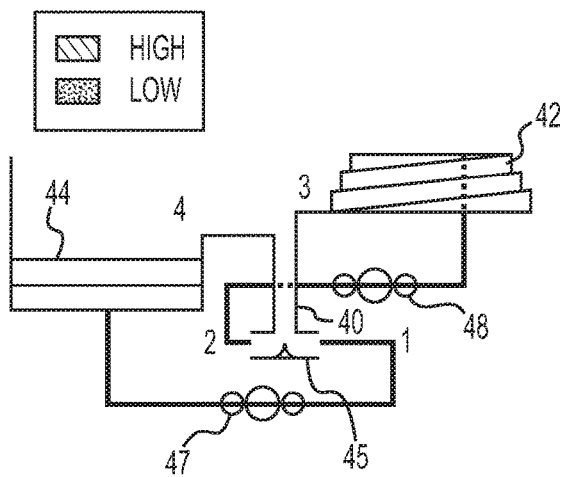
FIGS. 11A, 11B, and 11C are diagrams showing laminar Figure-8 flow configuration for fluid flow through a platform.
Figure 11B:
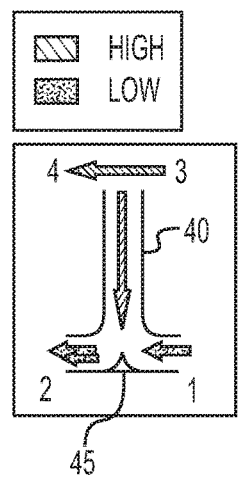
Figure 11C:
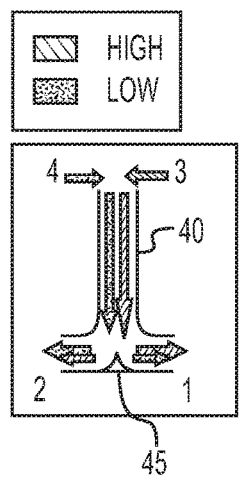

FIGS. 11A, 11B, and 11C are diagrams showing laminar Figure-8 flow configuration for fluid flow through a platform. A laminar flow channel 40 allows fluid paths of high and low concentration to flow side-by-side only mixing by diffusion. At the bottom of the channel, a flow splitter 45, such as a wedge, splits the flow, allowing the high and low concentrations to be directed to the cells 44 and the oxygenator 42, respectively. During downward flow, the flow coming from the cells 44 flows primarily around the flow splitter 42 (1 to 2, FIGS. 11A and 11B), through the oxygenator 12 (2 to 3), and into the cells 44 (3 to 4), with flow from 3 to 2 if the oxygenator flow rate is higher than the cell perfusion flow rate. During upward flow, media comes up through the cells 44 (1 to 4), primarily down the left side of the laminar channel 40 (4 to 2), through the oxygenator 42 (2 to 3), and primarily down the right side of the laminar channel 40 (3 to 1) (FIG. 11C). Pumps 47 and 48 direct the flow of fluid. High oxygenation level is shown with diagonal patterning, and low oxygenation level is shown in solid color.

e. Selective Sourcing

The cell seeding protocol requires that flow be down through the cell scaffold, which is shown in FIGS. 7A-7D, for the first eight hours to allow cells to attach, and then upwards for the remainder of the experiment to prevent the cells from occluding the scaffold channels. To allow the oxygenator to self-empty (thereby preventing volume from accumulating in the oxygenator and allowing the cells to dry out), the oxygenator is used in unidirectional flow circuit which is separated from the bidirectional scaffold perfusion flow circuit. To maximize the oxygenation of the media going to the cells during upward flow, the media intake is placed directly under the oxygenator output. To maximize the oxygen uptake in the oxygenator, the oxygenator intake is located on the opposite end of the MPS, where the concentration is expected to be lower. A schematic of this "selective sourcing" flow configuration is shown in FIGS. 12A and 12B.

Figure 12A:
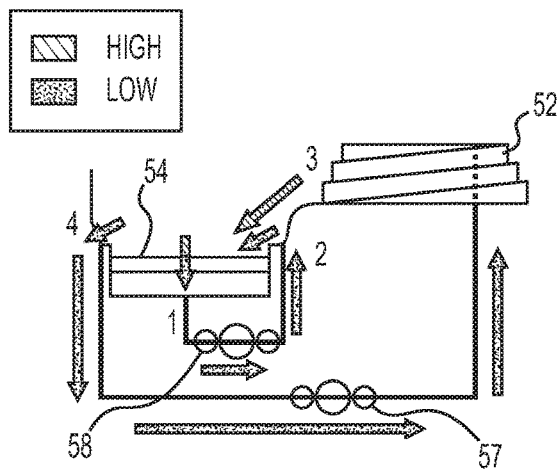
FIGS. 12A and 12B are diagrams showing selective sourcing configuration for fluid flow through a platform.
Figure 12B:
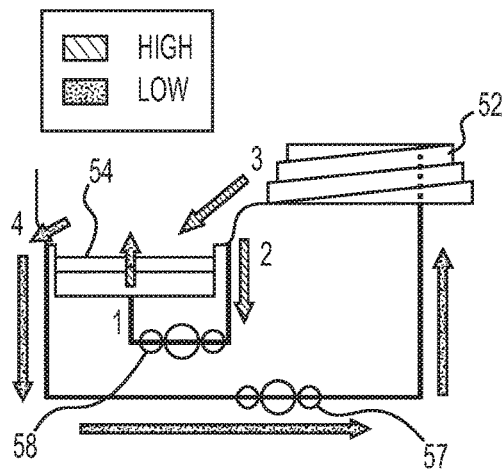

FIGS. 12A and 12B are diagrams showing selective sourcing configuration for fluid flow through a platform. During seeding (FIG. 12A), media flows down through the cells 54, where oxygen is consumed, then from 1 to 2. A mixture of media from 3 (high oxygen concentration) and 2 (low concentration) then flow both back through the cells 54, and also to 4, which feeds the oxygenator 52. During upward flow (FIG. 12B), the cells 54 are fed by media sourced from 2, which is a mix of high concentration from 3 and low concentration from the cells 54. The position of 2 directly under the oxygenator 52 output 3 increases the ratio of high to low concentration media, so the cells 54 see an oxygen concentration above the bulk average in the well. At the input to the oxygenator (4), the opposite occurs, pulling media that is below average oxygen concentration. Pumps 57 and 58 direct the flow of fluid. High oxygenation level is shown with diagonal patterning, and low oxygenation level is shown in solid color.

The selective sourcing circulation (FIGS. 12A and 12B) may feed the cells high concentration media during upward flow by placing the recirculation intake directly under the oxygenator output. During downward flow, the cells see a mixed concentration, but the oxygenator flowrate may be increased to increase oxygen transfer to the system. Both pumps may be on the same plane below the MPS, and the oxygenator may flow downhill to empty passively without reversing. Further, no extra reservoirs are required, making this configuration nearly as compact as the inline system.

4. Closed-Loop Oxygen Control

One advantage of having an oxygenator in a separate flow loop from the recirculation/perfusion pump, is that the oxygenator flow rate can be adjusted to adjust the concentration of a mixed system to a desired level. An oxygen probe, such as those made by Lucid Scientific (Atlanta, GA), may be integrated with the platform to sense the oxygen concentration, which would feed back to the pump controller to adjust the concentration. The concentration would be varied by increasing or decreasing the oxygenator flow rate.

Figure 13A:
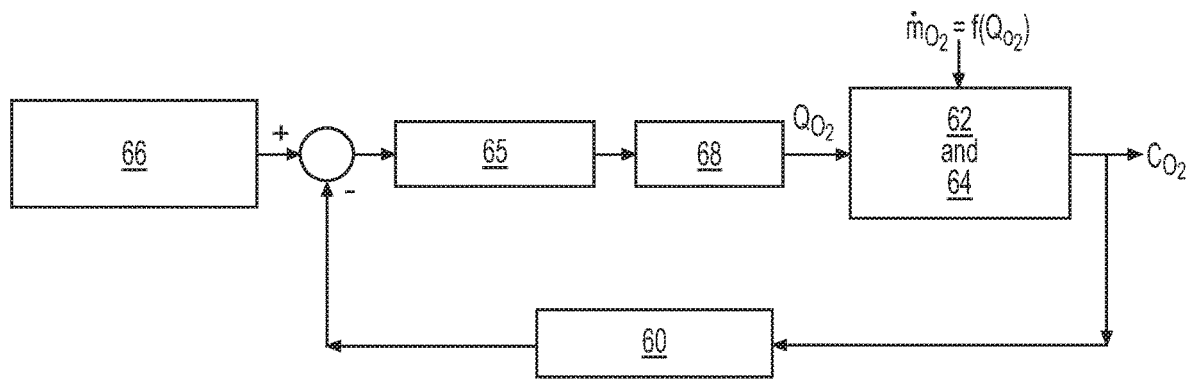
FIGS. 13A and 13B are diagrams showing closed loop oxygen control.
Figure 13B:
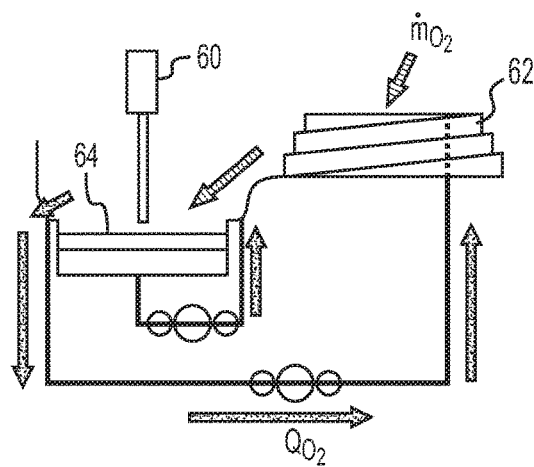

FIGS. 13A and 13B are diagrams showing oxygen concentration feedback control with platforms. A controller uses the error between measured and desired oxygen concentrations to adjust the oxygenator pump flow rate and thereby control the oxygen concentration in the MPS. FIG. 13B is a schematic of the oxygenator and MPS, with the oxygen probe measuring oxygen concentration in the MPS.

FIG. 13A is a block diagram of the oxygen concentration feedback control in a platform with a controller 65 controlling oxygenator pump 68 flow rate. The controller 65 uses the error between measured oxygen concentration measured by oxygen probe 60 and the desired oxygen concentration 66 to adjust the pump 38 flow rate, which regulates the flow rate in the oxygenator 62, and thereby controlling the oxygen concentration in the MPS well 64. FIG. 13 B is a diagram showing the oxygenator 62 and MPS well 64, with the oxygen probe 60 measuring oxygen concentration in the MPS well 64. Placement of the probe 60 requires careful consideration of local oxygen micro-environments, and depends on experimental need.

5. MPS Well and Scaffold Attachment Means

MPS wells are typically structured to allow bi-directional fluid flow through the well. The MPS well typically includes a three-dimensional space defined by a bottom surface and a circumferential wall. The bottom surface is typically the first surface of well floor. The well floor typically includes a second surface opposite to the first surface and at least one channel connecting the first surface with the second surface. The bottom surface may contact one or more built-in, or detachable, support structures. The well floor typically contacts at least one support structure with at least a portion of its first surface, and a capacitor with at least a portion of its second surface.

The support structures typically include means for cell or tissue support, attachment, and/or growth. The support structures may be any one of, or a combination of, a scaffold, a filter, and a scaffold support. In some embodiments, the scaffold, the filter, and the scaffold support are built-in in the well. In other embodiments, the scaffold support is built-in in the well, while the scaffold and/or the filter are detachable, and may be inserted into the well, or removed from the well, as needed.

Figure 7A:
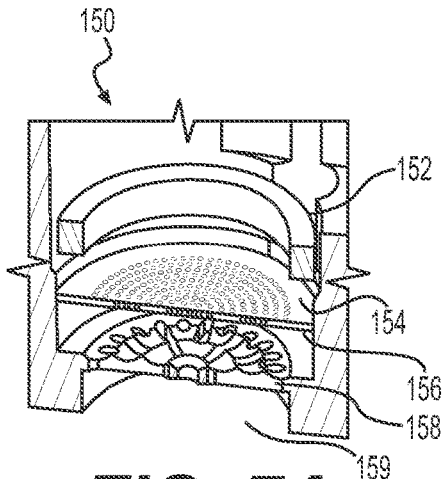
FIGS. 7A, 7B, 7C, and 7D are diagrams showing the components (FIGS. 7A and 7C) and the assembly (FIGS. 7B and 7D) of an MPS well 150 for the prior art platform (LIVERCHIP® MPS well, FIGS. 7A and 7B), and an MPS well 170 for the reduced volume revision 2 platform (Rev2, FIGS. 8C and 8D). Both platforms use the same polystyrene scaffold (CN Bio Innovations, Welwyn Garden City, UK) and filter (DURAPORE® 5 μm SVPP membrane filter, Millipore, Sigma). Cells are initially seeded above the scaffold 154 or scaffold 174 while the fluid is flowing downward and collect in the scaffold pores where the filter 156 or filter 176 prevents them from passing through. The scaffold support 158 or the scaffold support 178 prevents the filter from deflecting, which would allow the cells to move in between the filter and scaffold. At least a part of the scaffold support 178 contacts the well floor 177. After eight hours, the cells have attached to the scaffold walls and the flow is reversed to prevent cell growth from clogging the pores. The retaining ring 152 holds the assembly in place and is intended to prevent fluid from flowing around the scaffold and bypassing the cells. The Rev2 assembly improves this sealing function by using a VITON® gasket 173 and a retaining ring 172. The membrane capacitor 159 or the membrane capacitor 179, in combination with the filter and scaffold resistance, reduces the pulsatility of the flow, reducing the peak pressure below the scaffold (the membrane is not shown for the LIVERCHIP®).
Figure 7C:
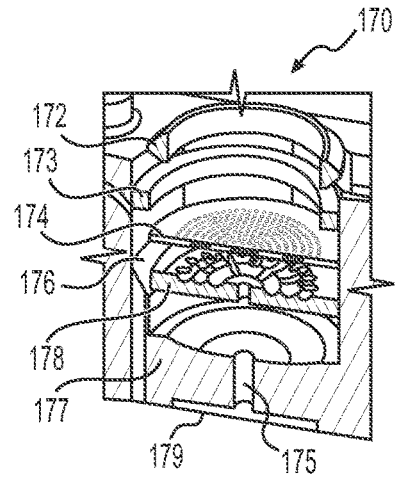
Figure 7B:
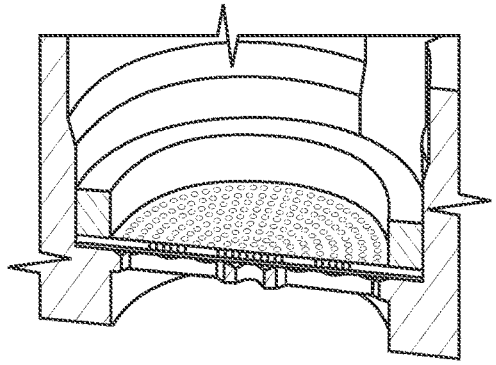
Figure 7D:
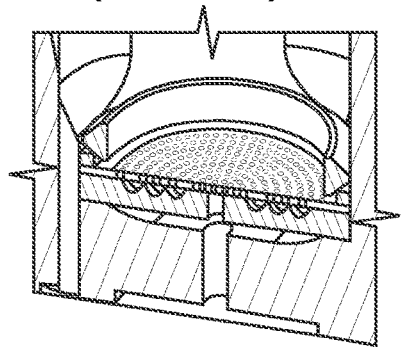

In an exemplary MPS well presented in FIGS. 7C and 7D, the well floor 177 includes at least one channel 175 and contacts at least a portion of the scaffold support 178 with its first surface, and at least a portion of the capacitor 179 with its second surface. The scaffold support contacts at least a portion of the filter 176 positioned between the scaffold support 178 and the scaffold 174. The filter 176 contacts at least a portion of the scaffold 174.

Typically, the seeded cells or tissue attach to the scaffold during the initial downward flow of the fluid. The filter serves to diffuse the flow and, in some aspects, in combination with a membrane capacitor, reduce the pulsatility of the diaphragm pumps (Inman, "*Development of a High Throughput 3D Perfused Liver Tissue Bioreactor*," Masters Thesis, Massachusetts Institute of Technology (2006); Inman, et al., *Journal of Micromechanics and Microengineering*, vol. 17, pp. 891-899 (2007)). During the initial downward flow of fluid that seeds the cells on the scaffold, the scaffold support prevents the filter from separating from the scaffold. Separation of scaffold and filter may result in cells migrating between the two and not binding to the scaffold openings.

In the embodiments where the scaffold and the filter are detachable, attachment means may be used to attach the scaffold and the filter to the MPS well, to the scaffold support, or both. Suitable attachment means typically provide fluid flow through the scaffold and the filter rather than through the edges of the filter and/or the scaffold.

Examples of attachment means include an elastomeric retaining ring, which relies on the deformation of the thin filter during installation, and its subsequent elastic response, to provide sealing. Because the filter is typically thin, any force generated is negligible, and the leak path around the scaffold is not sealed.

When the scaffolds are made of low fluid resistance materials, the majority of the media may flow through the scaffold rather than taking the higher-resistance path through the filter edge-wise and around the scaffold, because the flow resistance through the scaffold is comparatively low. However, when the scaffolds are made of higher resistance materials, there may be leaking around the scaffolds. This can result in uncertainty about local shear stresses and the transport rate of oxygen and nutrients to the cells, confounding interpretation of experimental data. The attachment means aim to minimize or prevent leaks around the scaffold. Suitable materials with low fluid resistance include materials for the scaffold and filter that when combined, provide a flow path through the scaffold and filter, rather than around the scaffold and filter by a ratio of at least 2. Materials with high resistance include materials for the scaffold and filter that when combined increase the resistance of the flow path through the scaffold and filter, and lower the resistance of the flow path around the scaffold and filter by a ratio of at least 2.

The combined materials for the scaffold and filter are typically considered of low fluid resistance when they permit less than about 5%, less than about 4%, less than about 3%, less than about 2%, or less than about 1% of the flow rate through the scaffold to leak around the scaffold. For example, if the flow rate through the scaffold is 2 µL/s, then scaffold and filter materials which permit a leak around the scaffold at about 1% of this, i.e., 0.02 µL/s, may be considered as scaffold and filter materials with low fluid resistance. Changing either the scaffold material or the filter material such that the resistance through the scaffold and filter increases by a factor of 2, i.e., the scaffold and filter materials permit a leak around the scaffold at about 2% of the flow rate through the scaffold, may be considered as scaffold and filter materials with high fluid resistance.

The characterization of materials as materials with high or low fluid resistance may also depend on the well set up, the total circulating volume, the flow rate, and other parameters that are application specific. For example, in some embodiments, the combined materials for the scaffold and filter are considered of low fluid resistance when they permit less than about 5% of the flow rate through the scaffold to leak around the scaffold, while in other embodiments, the combined materials for the scaffold and filter are considered of low fluid resistance when they permit less than about 1% of the flow rate through the scaffold to leak around the scaffold.

The attachment means may be formed to withstand at least 5 N of upward force. The attachment means typically secure the scaffold such that the secured scaffold does not leak more than 0.1 µL/s at a pressure differential of 40 kPa. The attachment means is typically easy to install, and may be inserted with an insertion force of less than 50N. The attachment means and its insertion method typically do not damage the scaffold, or other components of the platform. The attachment means typically does not occlude the holes on the scaffold, and is formed of a material that is cell- and drug-compatible. The attachment means may be easy to manufacture, and may be reusable.

a. Features for Scaffold Attachment Means
Attachment Means Withstands 5 N of Upward Force To maintain the scaffold in its position and prevent fluid from bypassing it, the attachment means that applies downward pressure on the scaffold should not become dislodged. The maximum fluid pressure multiplied by the area of the scaffold gives an upper bound on the upward force exerted on the scaffold assembly. The driving air pressure of the pneumatic pumps is typically 40-60 kPa, so the maximum fluid pressure is typically no greater than 60 kPa. Generally, the scaffold diameter is about 10 mm, so the force is about 4.7 N. The membrane capacitor under the scaffold, combined with the fluid resistance across the scaffold assembly, will limit the peak pressure at the scaffold to below the pump driving pressure.

The Scaffold May not Leak More than 0.1 µL/s at a Pressure Differential of 40 kPa Typically, the scaffold is fully sealed and no leaking occurs. Alternatively, a negligible leak, such as a leak at about 10%, about 9%, about 8%, about 7%, about 6%, about 5%, about 4%, about 3%, about 2%, or about 1% of the overall flowrate, may occur without loss of platform performance. For example, A leak rate of 0.1 µL/s is only 10% of the overall flowrate (1 µL/s), and the high pressure peaks would be both short in duration and likely lower than 40 kPa, due to the membrane capacitor.

Attachment Means Must not Damage Scaffold

Typically, the insertion and removal of the attachment means does not damage the scaffold or the platform itself. Typically, the platforms are reusable and should withstand many insertion/removal cycles.

Attachment Means does not Occlude Holes on Scaffold

The attachment means typically does not occlude the holes in the scaffold for the flow to pass evenly through each hole in the scaffold. This confines the sealing footprint area available on the scaffold to a narrow band at the periphery of the scaffold. The narrow band may have a size between 6 mm for inner diameter and 12 mm outer diameter. The narrow band may have a size between 7 mm for inner diameter and 11 mm outer diameter. The narrow band may have a size between 8 mm for inner diameter and 10 mm outer diameter.

Material is Cell- and Drug-Compatible

Incorporating a fluoroelastomer such as VITON® (The Chemours Company Fc, Llc, Wilmington, DE) may provide a more reliable sealing. In some embodiments the attachment means are formed of VITON®. Other examples of materials suitable for forming the attachment means include non-elastomeric materials such as polysulfone, polystyrene, or polypropylene.

b. Embodiments of Attachment Means
Sealing Lands

Figure 14A:
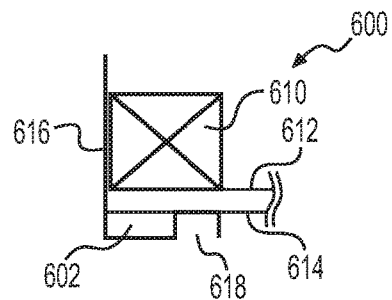
FIGS. 14A-14M are diagrams showing different embodiments of attachment means in an MPS well.

In this embodiment, the MPS well includes a sealing land as a contact area between the filter and scaffold support. When this contact area is reduced to a narrow band, a given downward force will produce a higher sealing pressure (FIG. 14A). The sealing lands may be used with any other embodiment of the attachment means.

Bi-Stable Spring

A bi-stable belleville washer, shown in FIGS. 14B-14F, may provide a strong downward force by engaging with features on the MPS wall. If a conical washer is sufficiently thin and elastic, it can be stable in the two positions shown, and will resist being flattened. Using a stainless steel washer, this may deliver the required forces in a compact mechanism. Means of easy removal may be a hole or a tab punched through the middle portion of the ring, which a custom tool may use to flip the spring to the original upward position. Once in this position, it could be easily removed with tweezers.

Angled Ring and Lip

Figure 14B:
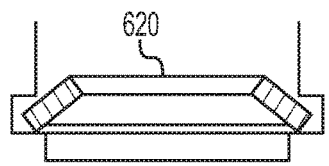
Figure 14C:
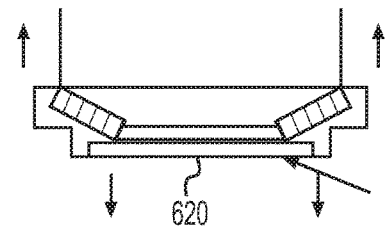
Figure 14D:
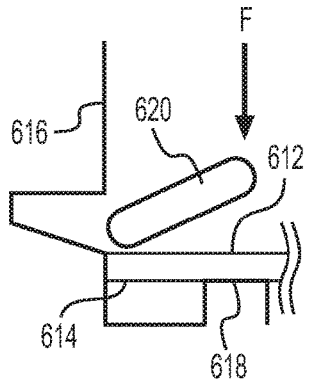
Figure 14E:
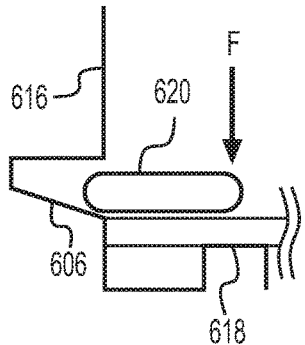
Figure 14F:
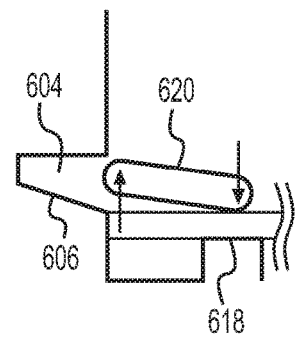
Figure 14G:
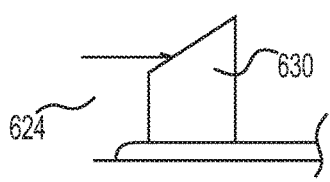
Figure 14H:
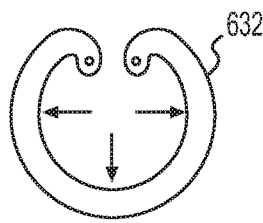
Figure 14I:
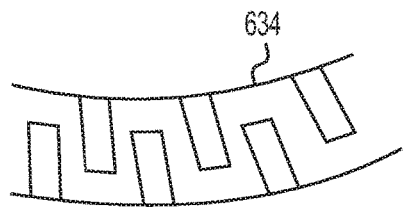

A retaining ring with an angled face to direct some of the radial force exerted by the ring downward may be used to provide sealing force on the scaffold (FIGS. 14G-14I). The angled face may be on the retaining ring, or on the MPS wall.

External Screw Mount with Spring

Figure 14J:
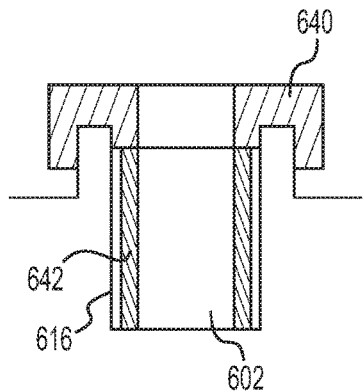
Figure 14K:
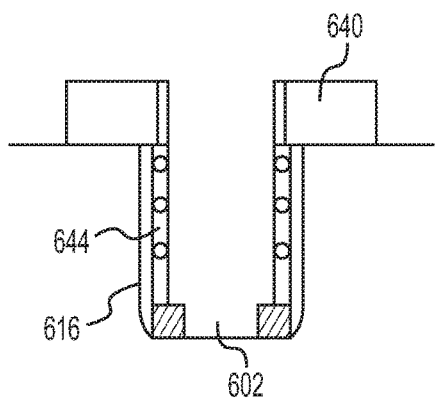

This attachment means may attach to the platform outside of or further up the MPS well, outside of the fluid, as shown in FIGS. 14J and 14K. This provides more options for attachment, such as a screw or bayonet mount. This fixes the position of the retaining device, and a predictable downward force is provided by an elastic element, whether a solid tube with a low Young's Modulus, a spiral or wave spring, or a custom flexure. In this embodiment, the fluid does not wick up between the spring and the MPS wall, and does not deplete the fluid at the bottom of the MPS and increase the total volume required to keep the cells covered. This may be achieved by keeping the gap small enough that the fluid volume is acceptable, or by use of a hydrophobic material or coating.

Snap Fit with Flexure

Figure 14L:
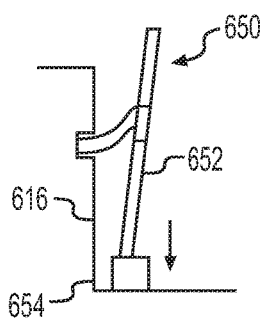
Figure 14M:
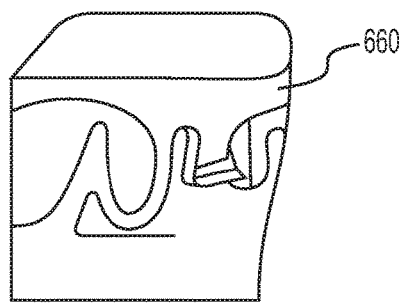

Similar to the external screw mount, the snap fit with flexure shown in FIGS. 14L and 14M uses a point of attachment outside of the fluid. A simple snap fit may engage with a pocket in the MPS wall and provide a downward force by elastic energy stored in the snap feature itself, or in a separated dedicated spring element. In this attachment means, similar to the external screw mount means, the fluid does not wick up between the spring and the MPS wall, and does not deplete the fluid at the bottom of the MPS and increase the total volume required to keep the cells covered. This may be achieved by keeping the gap small enough that the fluid volume is acceptable, or by use of a hydrophobic material or coating.

Deflecting Beam

Figure 15A:
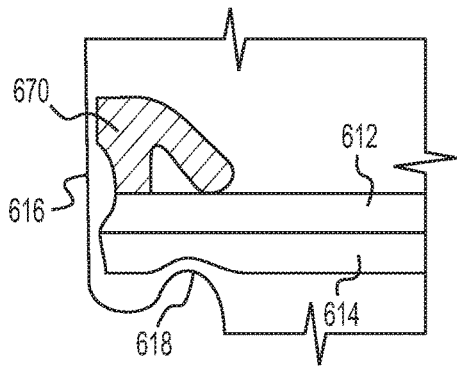
FIGS. 15A-15K are diagrams showing deflector beam, tilting ring, and wave spring embodiments of the attachment means.
Figure 15B:
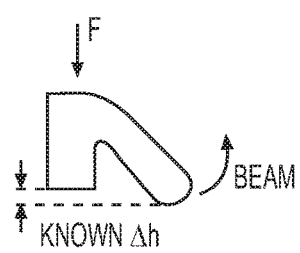
Figure 15C:
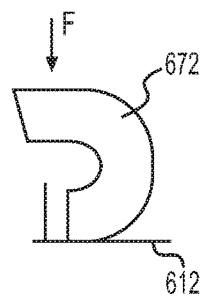

As a means of storing elastic energy and providing a downward sealing force, a deflecting beam may be integrated with an interference-fit ring (FIGS. 15A-15C). If the beam deflection remains elastic, this may provide a repeatable sealing force. The compact size and simplicity of the design may be outweighed by the challenge of achieving high enough forces without exceeding the elastic limit of such a small beam, as well as manufacturing and integrating a convenient means of removal.

Figure 15D:
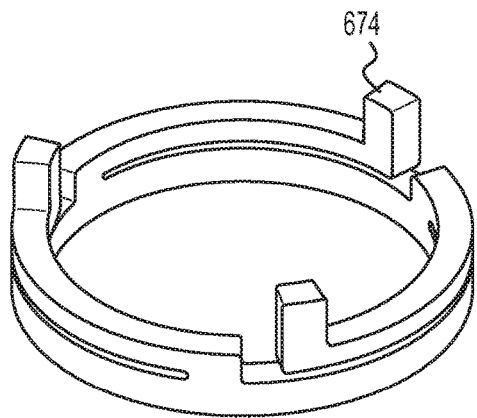
Figure 15E:
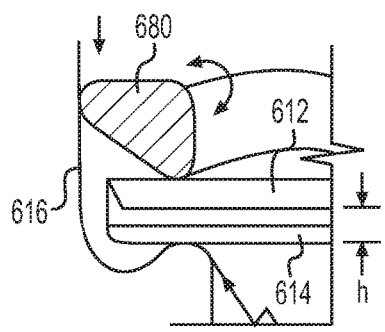
Figure 15F:
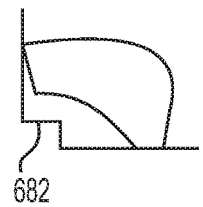

Another variation of this means may be a beam element that compresses both radially and axially. An example is shown in FIGS. 15D-15F. The advantage of such a means is that the radial stiffness may be lower than that of a ring, meaning that the holding force is less sensitive to small variations in well diameter. However, to achieve the high forces at such a small size, the elastic stress limit of the ring may be significantly higher than polymers allow. Stainless steel may perform adequately, but gouging the polysulfone MPS walls becomes a significant risk, and the spring must have a large contact radius to avoid excessive contact stresses in the polysulfone. An optimal beam geometry may provide a beam that is appropriately stiff in both directions at reasonable deflections, but which does not exceed the material yield stress. Making a beam wider will increase its stiffness linearly without increasing the maximum material stress, but this makes the beam stiffer in the perpendicular direction as the width to the third power. If the stiffness requirements in each direction are similar, this results in a roughly square cross section and the limiting factor becomes material yield stress. A material such as a superelastic nickel titanium alloy, stainless steel, NITINOL® alloys (Nitinol Devices and Components, Inc., Fremont, CA), such as NITINOL®55, or NITINOL®60, may be suitable for this attachment means.

Tilting Ring

Figure 15G:
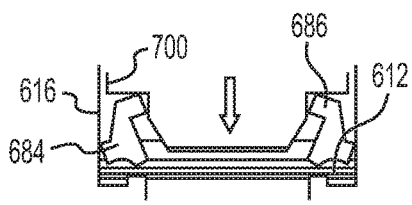
Figure 15H:
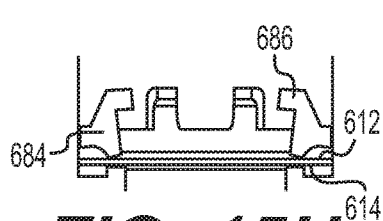
Figure 15I:
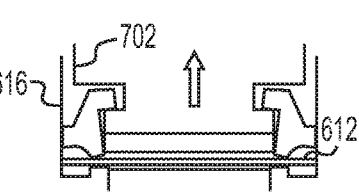

With an interfering ring of a triangular cross-section, as shown in FIGS. 15G-15I, if the outer top edge is pressed below the inner top edge, the hoop compression of the inner bottom edge results in reaction forces which create a moment on the ring. When installed, this moment is balanced by the frictional force from the wall and the compressive sealing force on the scaffold assembly.

The primary challenge to developing this concept is manufacturing to tight tolerances. The tilting ring typically requires elastic deformation to produce a reliable sealing force. The high stiffness of rings in radial compression results in a narrow window of radial deflections that provide adequate friction force but avoid plastic deformation.

One embodiment of the tilting ring concept uses deflection of multiple projections to provide the required twisting of the ring, rather than pushing on the outer edge (FIG. 15H). These projections could then be used for removal. The projections may be stiff enough to twist the ring outward against its own elastic force as well as the friction force on the wall. The beams are typically stiff enough to cause adequate torsion at this small scale.

Wave Spring

Figure 15J:
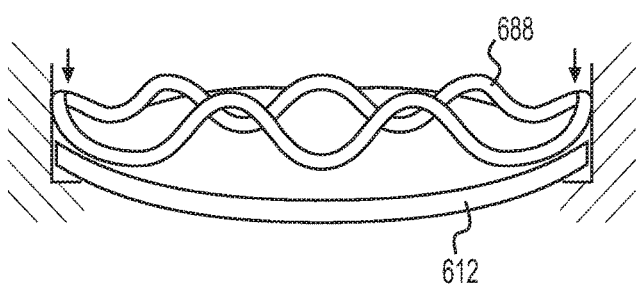
Figure 15K:
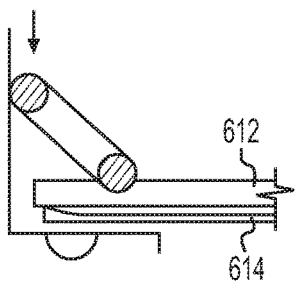

The wave spring, shown in FIGS. 15J and 15K, is a variation on the tilting ring means, using a waved piece of stainless steel wire bent into a shallow cone shape. The smaller diameter is placed down, and the larger diameter, which is slightly larger than the well, is pushed down. The crests at the top are held by friction against the well wall, and as they are pushed downward the bottom crests of the spring make contact with the scaffold, twisting the ring inward and causing reaction forces that push down on the scaffold to seal. The wire is generally stiff enough to resist this twisting. The primary advantage that this method has over the retaining ring is that the waves introduce more compliance to the ring, allowing looser tolerances in the diameters of the ring and the well.

Ring with Elastomer

Elastomers such as VITON®, which have a high yield strains and low Young's moduli offer reliable sealing at a small size. Possible configurations for attachment means using such elastomers are shown in FIGS. 16A-16C. The low yield strain of non-elastomeric materials such as polystyrene or stainless steel requires long beam lengths to reach high forces while remaining elastic, and when directly compressed, their high Young's moduli result in high forces at deflections below machining tolerances. Elastomers, by contrast, can deform under low forces to make conformal contact with mating surfaces, which improves sealing, and can store elastic compressive forces at reasonable deflections without plastically deforming.

An exemplary attachment means is a chamfered retaining ring and a VITON® gasket, as shown in FIG. 7D, a configuration which can seal up to 40 kPa, well above any anticipated pressure drop in the platforms.

FIGS. 14A-14M are diagrams showing different embodiments of attachment means and MPS well assembly 600. FIG. 14A shows a sealing land 618 in an MPS well 602, with an MPS well wall 616, retaining ring 610, scaffold 612, and filter 614. The sealing land 618 reduces the contact area on the scaffold support to a narrow band and increases sealing pressure for a given downward force. FIGS. 14B-14F are diagrams showing a bi-stable spring 620. In FIG. 14B, a bi-table spring 620, such as a belleville washer, is in a relaxed state. In FIG. 14C, the bi-stable spring 620 engages with features on the MPS wall 616 to provide a downward force on the scaffold 612 and filter 614. In FIG. 14D, the bi-stable spring 620 is in its relaxed state, the outer diameter of the washer can fit within the pocket 604 of the MPS wall 616. A downward force initiates deflection. In FIG. 14E, as the bi-stable spring 620 deflects past the equilibrium point, the outer edge expands, and a ramp 606 on the MPS wall 616 pushes this edge upward. This creates a small gap under the bi-stable spring 620 required to push it past equilibrium. In FIG. 14F, the pocket 604 in the MPS wall is short enough that it catches the edge of the bi-stable spring 620 before the washer can relax to the full height. The bi-stable spring 620 may include tabs or similar features for removal. FIG. 14G shows a ring and lip embodiment of an attachment means. An elastic chamfered ring 630 with an outer diameter slightly larger than the MPS wall diameter relaxes into a groove 624 in the MPS wall. A downward force on the ring compresses the filter material and allows the ring to relax further into the groove. When the downward force is released, the radial outward force of the ring results in a force downward on the filter and scaffold assembly due to the chamfered edge. Various existing expanding ring designs, such as ring 632 in FIG. 14H, could increase the allowable deflection over a solid ring. One such design (FIG. 14I) involves a zig-zag pattern cut into a ring 634 to convert hoop compression into bending of many small beams in series, thus allowing greater deflection while remaining within the material elastic limit. FIGS. 14J and 14K are diagrams showing the external screw mount embodiment of the attachment means. A screw or bayonet mount 640 to the top of the MPS well 602 with MPS wall 616 compresses an elastic tube 642 (FIG. 14J) or a spring 644 (FIG. 14K) to provide a downward sealing force on the scaffold assembly (not shown). FIGS. 14L and 14M show the snap fit embodiment of the attachment means. Cantilever snap feature 650 engages with a pocket 654 in the MPS wall 616. The downward sealing force can come from deflection of a beam 652 on the snap feature 650 (FIG. 14L), or from a separate spring element, such as a flexure 660 cut from a single tube (FIG. 14M).

FIGS. 15A-15K are diagrams showing deflector beam, tilting ring, and wave spring embodiments of the attachment means. FIG. 15A shows an outer ring 670 interferes with the MPS wall 616, and this radial force results in a frictional force that keeps the ring in place. When the user presses the ring downward, a thin section of the ring deflects elastically in bending, providing a consistent downward sealing force that is less than the friction force against the wall. FIG. 15B shows that by incorporating a height difference between the beam and the base of the ring, a repeatable deflection (and therefore force) can be achieved, regardless of the insertion force F. FIG. 15C shows a rotated configuration, such as a rotated outer ring 672, which reduces the footprint of the ring, potentially providing a greater force without occluding the scaffold 612. FIG. 15D shows an alternate deflecting beam design. The beams 674 act as both the radial spring element that generates friction force, and also the vertical spring that is loaded during installation to provide a downward sealing force. FIGS. 15E and 15F show a tilting ring 680. A downward force on the outside top edge of the tilting ring 680 results in a stored moment from the compression of the inside bottom edge. Because the outside top edge is constrained by friction against the MPS wall, this results in a downward sealing force on the scaffold 612 and filter 614. FIG. 15F shows that deformation, and therefore reaction force, can be made more repeatable by a feature, such as a step 682, that limits the deflection distance h. FIGS. 15G-15I are diagrams showing a tilting ring 684 with deflecting clips 686. In FIG. 15G, an insertion tool 700 displaces multiple protruding clips 686 radially outward and down, causing the outer edge of the ring to slide downward on the MPS wall 616. When the tool is removed, the ring 684 partially untwists, exerting a downward force on the scaffold 612 (FIG. 15H). To remove the ring 684, a removal tool 702 with fine teeth engages with the protruding clips 686 to remove the tilting ring 684. FIGS. 15J and 15K show a wave spring 688, which includes a ring stainless steel wire that has waves formed into a shallow cone (FIG. 15J). Similar to the tilting ring 684, when the top crests are pushed down by the installation tool, this induces reaction forces that provide a downward sealing force against the scaffold 612 and filter 614 (FIG. 15K).

FIGS. 16A-16C are diagrams showing different embodiments of a retaining ring with an elastomer as attachment means. In FIG. 16A, a constrained volume causes a downward force to provide sealing against both the MPS wall 616 and the scaffold 612. This same effect could be achieved by a round gasket 692, or a square gasket 690, pressed into a gap between the MPS wall 616 and the scaffold 612 (FIGS. 16A and 16B). If a ring with a smooth interference fit against the wall is used, the radial force may provide adequate sealing against the wall, and only a seal against the scaffold is necessary (FIG. 16C).

6. Media Exchange

The media exchange system in the platforms actively pumps fresh media from a fresh media reservoir with a pump, e.g., with a media exchange pump, and the waste media passively spills over into an effluent collection reservoir. If the flow rate of fresh media into the system is significantly lower than the circulation and oxygenation flow rates, then the system is considered fully mixed, and the fluid spilling into the effluent is a uniform mixture of old and new media. For continuous media exchange, where the media feed rate is orders of magnitude lower than the recirculation rate, this fully-mixed model applies.

Another pumping channel for effluent collection may be used to actively evacuate old media. In this embodiment, the difference in flow rate between the source and effluent pumps may not cause accumulation or depletion of media in the system. An effluent intake similar to the MPS and Oxygenator inlets shown in FIGS. 2A and 2B could avoid depleting the MPS by drawing air when the volume dropped lower than the intake. This can also be solved by including an effluent spillway as well as an effluent pump, and ensuring that the media input rate is slightly is higher than the media extraction rate.

Storing the fresh and effluent media off-platform may allow large enough volumes to flush the system with fresh media, thereby achieving batch exchange. In batch exchange, the entire volume of fluid in an individual replicate lane is exchanged with the same volume of fresh fluid.

7. Closed Fluidic Systems

In the closed fluidic systems, the volume is constrained and free of surface forces, and all constraints are fully wetted. The closed systems allow for adequate oxygenation of the same amount of cells as open-well systems, but with further reduced circulating volumes of fluid. Circulating volumes less than 500 µL may be used in closed fluidic systems.

The closed fluidic system may have the same basic structure of a fluidic plate and pneumatic plate sandwiching a polyurethane membrane. A single-use closed fluidic plate, or a single-use closed fluidic platform, may also be generated as needed. If the platform is adapted to a disposable design, its diaphragm pumps may be adopted to be formed of any suitable material, such as COC, and bonded to the bottom surface of a fluidic plate.

The membrane oxygenator for the closed fluidic systems typically uses a single in-line circuit much like the LIVER-CHIP®. This feeds media directly from the oxygenator to the cells in both flow directions. There are three main differences between this platform and the LIVERCHIP®: (1) the use of a membrane oxygenator, (2) a media exchange system, and (3) a cap that seals the MPS but that may be removed to accommodate cell seeding. A cross section of one embodiment of this proposed platform is shown in FIG. 17C, and a top level view is shown in FIGS. 17A and 17B.

a. Low Circulating Volume in Closed Fluidic Systems

The closed fluidic systems may have a circulating volume between about 50 μL and about 150 μL. The volume trapped in circulation and the fluidic capacitor may be about 55 μL for the 6×RL, which may be reduced to about 40 μL. In the closed fluidic systems, the oxygenator may have a volume of 10 μL, and for 8 mm diameter of exposed scaffold, an additional 50 μL may be added. As the vertical fluid space above the scaffold and through the scaffold support may be as low as 1 to 2 mm, making this volume about 50 μL or 100 μL, a reasonable total is 100 to 150 μL of a circulating volume in the open-well platforms. The circulating volume of the open-well fluidic system allows for 50 to 60% reduction in the circulating volume relative to that in the LIVERCHIP® platforms. The circulating volume in the closed fluidic systems is about one tenth of the LIVER-CHIP® volume. The comparative values for fluid volumes in the three different systems are shown in Table 2. These low circulating volumes may more readily reveal autocrine biomarkers or other biological molecules of interest.

An additional consideration in the closed fluidic system is the height of the effluent, which sets the system pressure, and avoiding a negative pressure on that line. The hydrophobic membrane will resist fluid leaving the system, but may allow gas to enter if the system is at lower than atmospheric pressure. The effluent exit to atmosphere should therefore be located some amount above the system level.

b. Membrane Oxygenator for Closed Fluidic Systems

Membrane oxygenation may be used in this volumetrically confined system. Hydrophobic nanoporous membranes (pore sizes between about 100 nm and 450 nm) made from polypropylene, polycarbonate, and PTFE appear to have mass transfer coefficients exceeding that of a free surface, likely due to the velocity profile near the membrane reducing the diffusion boundary layer thickness (Balgobin, "Bubble-Free Oxygen and Carbon Dioxide Mass Transfer in Bioreactors Using Microporous Membranes," Masters, University of Western Ontario (2012)). Mass transfer is reported to increase with contact angle; a higher oxygen transfer rate was observed with more hydrophobic materials.

The transfer rate through a free surface may be estimated as follows. At 1 μL/s, equation 2.21

$$\phi \equiv \frac{C_{out} - C_{in}}{C_{sat} - C_{in}} \approx \left(1 - e^{-\frac{1}{Pe_h}}\right) \qquad \text{Equation 2.21}$$

suggests a diffusion depth to exposed surface area ratio h/A of 0.0005 [mm$^{-1}$] will give an oxygenation potential of 1.00 (i.e., fluid leaves the oxygenator fully saturated). Assuming a 2 mm wide two-sided oxygenation channel 100 μm tall, that is oxygenated from top and bottom, a 50 mm length is required to achieve h/A=0.0005 [mm$^{-1}$]. The same dimensions, but oxygenated from one side, would still give an oxygenation potential of 0.998 (the model over-predicts the oxygenation potential, but this gives a rough guide to appropriate dimensions). The hydraulic resistance $R_h$ can be approximated by $$R_h = \frac{12L\mu}{wh^3} \qquad \text{Equation 6.1}$$

where L is the oxygenator length (0.050 m), μ is the dynamic viscosity (0.78 mPa*s for DMEM/F12 Medium at 37° C.) (Wang, et al., Journal of Biomechanics, vol. 45, pp. 1212-1218 (2012)), w is the channel width (0.002 m) and h is the channel height (0.0001 m). Multiplying by a flow rate of 1 μL/s (1×10$^{-9}$ m$^3$/s) gives a pressure drop of less than 0.2 kPa, which the pneumatic pumps can easily accommodate (Inman, et al., Journal of Micromechanics and Microengineering, vol. 17, pp. 891-899 (2007)), and well below the pressure required to drive liquid across a suitable membrane (for a 1 μm pore diameter EPTFE membrane this pressure was found to be on the order of 100 kPa. The volume of fluid in the oxygenator would be 10 μL. Equation 2.21 allows quick prediction of oxygenator efficiency for a wide range of channel dimensions.

One advantage of the membrane oxygenation method, in addition to allowing a closed-volume system, is that flow is reversible, and the inline flow configuration can be used. This reduces the number of pumps required, and feeds media from the oxygenator directly to the cells when flowing upwards or downwards. While it does not allow for real-time oxygen control by changing the flow rate—changing the perfusion rate would change local shear stresses and might inadvertently alter cell function—such control could potentially be achieved by controlling the local gas environment outside the membrane. A further advantage of micro- or nano-porous membranes is that the oxygenator typically functions as a bubble trap, allowing gas to flow out through the membrane, while retaining the fluid.

To allow removable fluidic sealing of the membrane, a clamping block with an elastomeric gasket can compress the membrane in long channels, confining flow to the uncompressed region. Potential configurations for such a design are shown in FIGS. 18A-18D. Depending on the stiffness of the membrane relative to the width of the channel, the channel height could be defined by deflection of the membrane alone, or by a spacer. To make the system more compact, the oxygenator could have a membrane on the top and bottom, but this may result in a leak path that is challenging to seal. For a single-sided oxygenator, two potential clamping plate configurations are shown in FIGS. 19A and 19B. In each of these clamped configurations, the membrane hydrophobicity is advantageous. Even if there is a very small gap, surface tension forces will prevent fluid from penetrating if the pressure differential is not extreme.

Figure 18A:
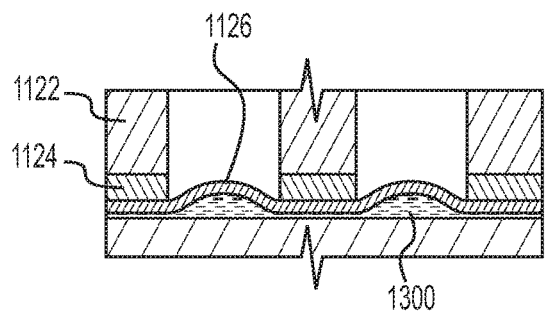
FIGS. 18A-18D are diagrams showing a cross-section through different embodiments of membrane oxygenators for the closed fluidic systems.
Figure 18B:
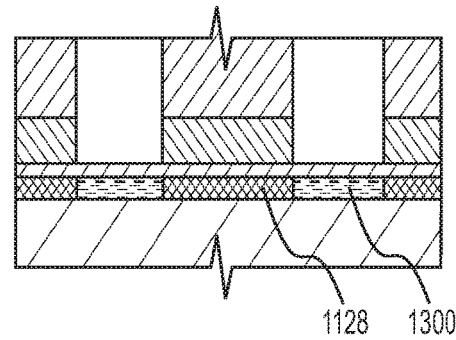
Figure 18C:
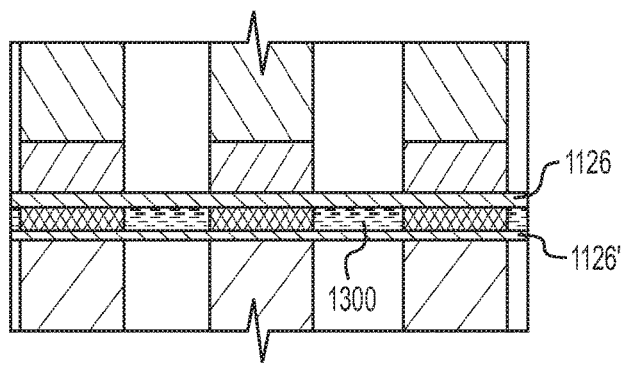
Figure 18D:
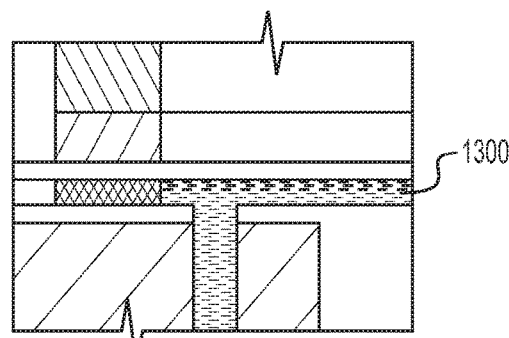
Figure 19A:
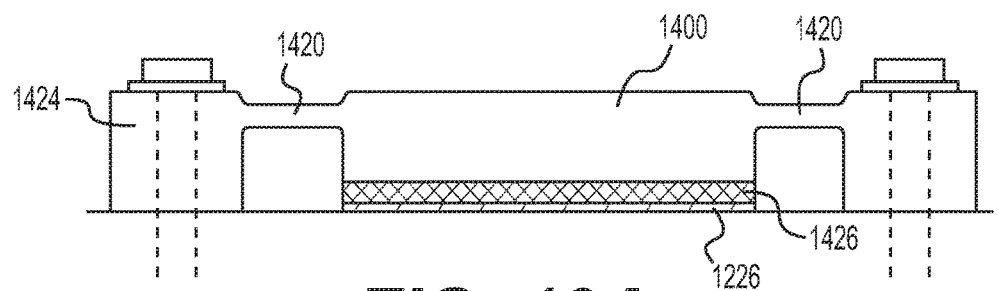
FIGS. 19A-19C are diagrams showing means of attaching a membrane to the platform. The membrane 1226 may be clamped by a plate 1400 that has narrow elastic beams 1420 connecting to posts 1424 that are bolted to the platform. The elastic beams 1420 provides a spring element that would minimize bowing of the clamping plate, and an elastomer gasket 1426 above the membrane distributes the force to provide an even sealing pressure to the membrane.
Figure 19B:
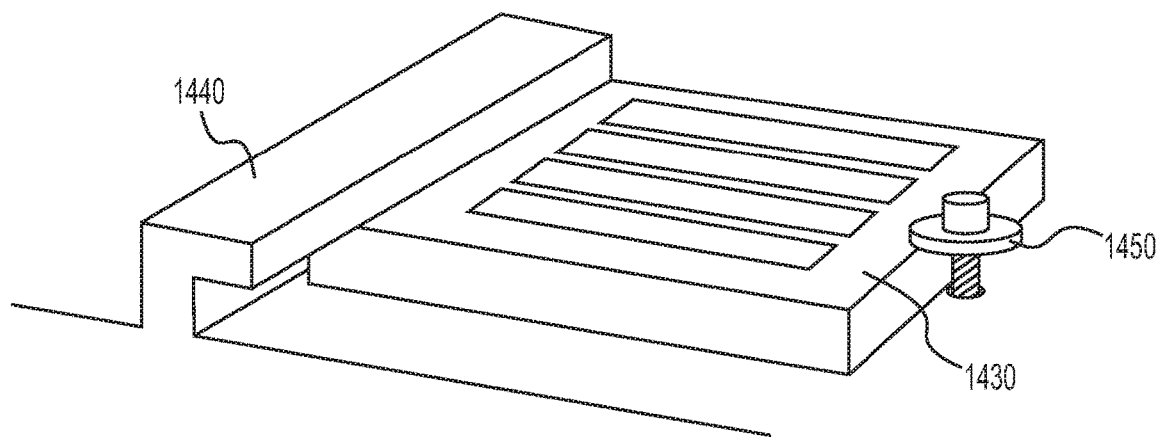
Figure 19C:
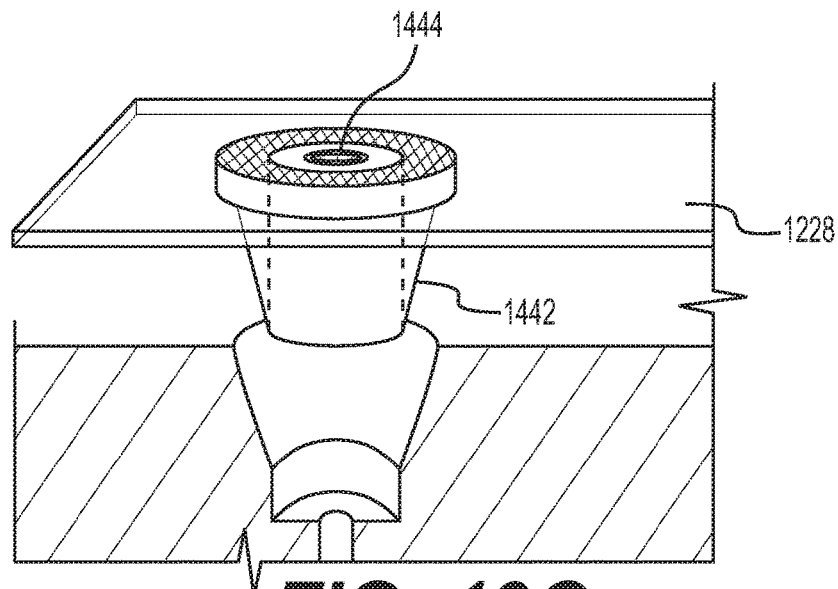

To gain the benefits of a double-sided oxygenator, while mitigating the leak path shown in FIG. 18D, the membrane may be bonded to a secondary plug which would seal to the platform. Such a configuration is shown in FIG. 19C. The top membrane could then be bonded to this bottom membrane, eliminating the need for a clamping block.

c. Media Exchange in Closed Fluidic Systems

Figure 20:
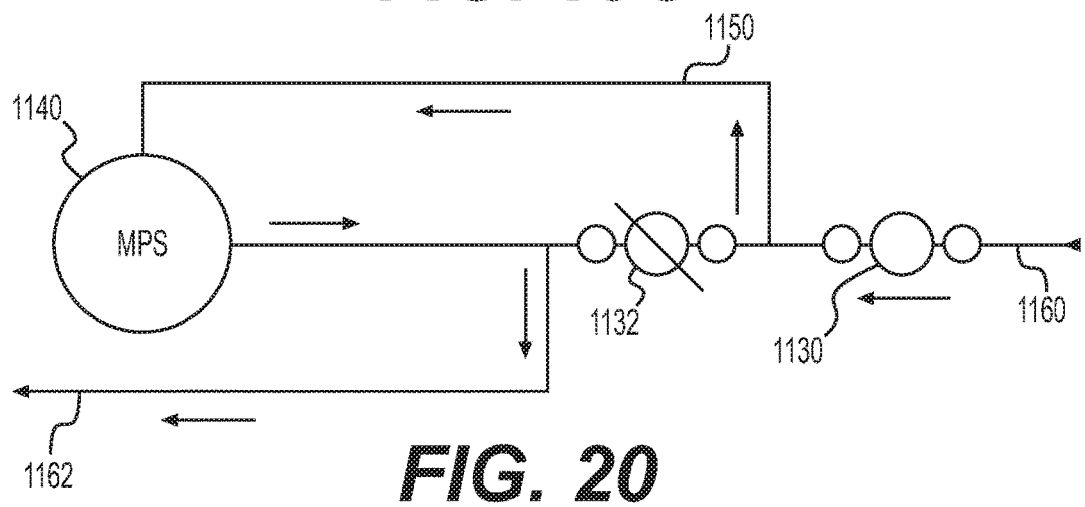
FIG. 20 is a diagram of media exchange configuration for the closed fluidic system. The media exchange configuration has media inlet 1160 and effluent 1162 on either side of the recirculation pump 1132. To feed media in, all chambers of the recirculation pump 1132 are closed, blocking this path. The media exchange pump 1130 then adds the desired amount of media through the oxygenator path 1150. If media is flushed through the system, the dead volume in the channels around the recirculation pump 1132 is on the order of 1 µL. This could also be eliminated by pumping backwards for one or two cycles. Some mixing between old and new media may occur in the MPS well 1140.

A media exchange inlet and an outlet may connect to the circulating fluid path on either side of the recirculation pump, as shown in FIG. 20. This may allow a greater control over the media being added. Continuous media exchange allows delivery of fresh media to the cells, because the addition flow rate is orders of magnitude smaller than the recirculation flow rate. This typically results in a fully mixed system, so the fresh media exposure of the cells can be modeled straightforwardly. Batch exchange occurs by sealing the recirculation pump while fresh media flushes the system. This system would also allow programmed feeding schedules, so that a set amount of media may be dosed at discrete times. This approach in general offers an easier system to model than an open system, allowing biologists to answer questions that depend on these different dosing schemes. The inlet and outlet tubes may be standard HPLC fittings. Other connectors such as LUER-LOK® (Becton, Dickinson and Company, Franklin Lakes, NJ) may also be suitable. In packing multiple replicate lanes on a chip, it may be advantageous to ensure that the effluent ports and the fresh media supply ports are on opposite sides of the platform if they have to connect to an external supply. Depending on packing and the relevant volumes, the reservoirs could also be on the platform itself.

d. MPS Caps for Closed Fluidic Systems

The MPS must be sealed for this to be a closed-volume system. Cell seeding in a closed-volume system requires the cells to be pipetted onto the scaffold and allowed to settle. The cell seeding may be accommodated by using a sealing cap. A sealing cap with either a solid surface or an oxygenation membrane may be placed into the well after the cells are seeded. In one embodiment, the caps are inserted downward. A cap that is inserted downward may displace fluid around the sides, which can be aspirated. Once seated, the cap may also push fluid out through the effluent channel, which typically remains open. The cap may seal in place by a locking taper, screw threads, or a bayonet mount. In another embodiment, the caps slide from the side. A sliding cap may cause less disturbance to the fluid, pushing a fluid front off the top as it slides in place.

Typically, the caps are applied without introducing bubbles, and that any fluid displaced by the cap typically exits either around the cap or out the effluent tube, so as not to create flow or pressure pulses that could displace the cells. Therefore, the MPS caps typically do not introduce bubbles to the MPS well and allow the displaced media to exit around the cap, or out of the effluent tube.

8. Clamping and Sealing

The components of the platform, once assembled, may be held together by any suitable means, such as by screws, clamps, adhesives, pins, bolts, gaskets, or any combination thereof. For example, the screws holding the pneumatic and fluidic plates together may be replaced with an alternate clamping method using no screws or a substantially reduced number of screws.

One reason for using screws in the platforms is that because the polyurethane membrane is so thin, it is stiff enough in compression that bending of the acrylic and polysulfone plates becomes a consideration. If a thicker elastomer gasket is placed under the membrane, deformation occurs primarily in the gasket, allowing a less even distribution of forces, and potentially fewer screws. This gasket approach was designed by Continuum Innovations (Boston, MA) may be used with platforms that do not seal adequately without them. The main challenge is achieving deterministic and repeatable pump volumes: Continuum addressed this with acrylic protrusions that hold the pump and valve geometry, but that surrounded by an elastomer to provide fluidic sealing. Such gasket configurations, if the sealing lands are significantly more compliant in compression than the platform is in bending, could allow the use of significantly fewer screws, or even a custom clamp.

In a disposable platform, the plates may be temporarily clamped, compressing the gasket, and then bonded, either ultrasonically or with an adhesive. Suitable adhesives include cyanoacrylates, UV-cure acrylic adhesives, and solvents providing solvent-bonding. After clamping is released, the bond would maintain a pressure seal. This might enable use of membrane materials that cannot be effectively bonded.

B. Membrane

Generally, the fluidic plate and the pneumatic plate are separated by a membrane. These three components may be assembled and disassembled as needed. In some embodiments, the membrane may be bonded to the system, or absent.

1. Structure

The membranes typically include two opposing surfaces, with one surface contacting the bottom of the fluidic plate and the opposing surface contacting the top of the pneumatic plate.

The membranes typically include openings, e.g., holes, to accommodate the numerous channels connecting the fluidic and pneumatic plates. The membranes are typically flexible, have an overall thickness between about 10 μM and 200 μM, such as about 10 μM, about 25 μM, about 50 μM, about 75 μM, about 100 μM, about 125 μM, about 150 μM, about 175 μM, or about 200 μM, and length and width sufficient to cover the bottom of the fluidic plate and the top of the pneumatic plate.

2. Materials

Typically, the membranes are formed of an elastomeric material, such as Exemplary membrane materials include thermoplastic polyurethane (TPU) membrane sterilized by ethylene oxide gas (EtO).

C. Pneumatic Plate

Active fluid flow in the platforms may be achieved by any suitable actuation means. The actuation means may be grouped together into a pneumatic plate to be used in combination with the fluidic plate. The actuation means may be separate from the fluidic plates, and may be attached or detached from the fluidic plate as needed.

Suitable actuation means include diaphragm pumps, magnetic pumps, electro-mechanical pumps, syringe pumps, and combinations thereof.

The choice of actuation means is typically dependent on the flow rate needed to achieve a target oxygen concentration. Generally, diaphragm pumps are sufficient and suitable for achieving flow rates and oxygenation suitable for cell and tissue culture.

Diaphragm pumps typically include a central pump chamber and two valves. The pumps typically allow for bi-directional volume-determined flow. See Inman, *Journal of Micromechanics and Microengineering*, vol. 17, pp. 891-899 (2007), for detail on the pump operation.

1. Structure and Function of Diaphragm Pumps

Bi-directional micropump typically includes a clamshell-like pump chamber, two active valves and a fluidic capacitor. The contoured shape of the pump chamber used in combination with a thin, flexible membrane reduces actuation pressure requirements and leads to a constant stroke volume. The capacitor converts pulsatile flow from the pump into continuous flow.

The pump may be made by sandwiching a thin, flexible membrane between two plates. The top plate typically contains the top half of the pump chamber, valve seats and fluidic channels. The bottom typically plate contains the bottom half of the pump chamber, the valves and connections to the pneumatic lines.

A valve is opened when negative air pressure pulls the membrane toward the bottom plate. Positive air pressure closes the valve by pressing the membrane against the valve seat. The pump chamber fills when negative pressure is applied to the membrane, and drains in response to positive air pressure.

In some embodiments, the pump chamber typically has a 1.5×3 mm footprint and a 1.58 mm radius of curvature. The combined volume of the top and bottom halves of the pump chamber may be 0.92 µL. The circular valves have the same width and radius of curvature as the pump chamber. The fluidic channels may have a 0.4 mm×0.4 mm D-shaped cross-section. The fluidic channels may have any cross-section, such as rectangular or square, with sharp corners. The diaphragm pumps functioning as recirculation pumps or media exchange pumps typically include pumps with valve chamber and pump chamber geometry providing about 1 µl/stroke volume. The oxygenator pump may include a pump chamber geometry providing between about 1 µl/stroke and 3 µl/stroke volume, such as about 2 µl/stroke volume.

Small inserts between the top plate and the membrane prevent pneumatic pressure from deflecting the membrane into the fluidic channels. This eliminates pneumatic bleed off.

In order to maintain a set flow rate, a constant volume of fluid is pumped during each cycle. This is facilitated by the contoured surfaces of the pump chamber that limit the maximum deflection of the membrane. Additionally, the fluidic channel was cut across the length of the pump chamber. This prevents the flexible membrane from throttling or closing the outlet of the pump chamber before all fluid is ejected, alleviating problems of valve leakage.

Similarly, a small channel in the bottom plate ensures that the membrane does not prematurely seal off the pneumatic input when vacuum is applied. These channels significantly improve pump consistency and performance.

2. Methods of Making

The pumps may be fabricated by standard CNC machining but may be readily amenable to other fabrication and replication techniques such as laser machining (Young et al., *J. Biomech. Eng.*, 121:2-6 (1999)) or micromolding (Xia et al., *Ann. Rev. Mater. Sci.*, 28:153 (1998); Heckele et al., *J. Micromech. Microeng.* 14:R1-R14 (2004)). With CNC machining, a clean room microfabrication facility is not needed, and a variety of machinable materials can be chosen based on the target application.

III. Methods of Making the Platforms

A. Materials

Generally, the materials suitable for forming the fluidic plate are materials that are not cytotoxic to cells, do not absorb lipophilic drugs, and can be subject to sterilization. Exemplary materials suitable for forming the fluidic plate include polysulfone (PSU), TEFLON®/PTFE, polystyrene, plasma-activated polystyrene, cyclic olefin copolymer (COC), and stainless steel.

Many microfluidic and organ-on-chip systems are fabricated from PDMS (Polydimethylsiloxane, a silicone rubber). PDMS can be poured into 3D printed molds with fine feature resolution, which allows for faster prototyping than with materials that require machining or etching. It can be bonded to itself and to glass by plasma surface activation. It is relatively biologically and chemically inert, and it is highly permeable to oxygen relative to other polymers (Oomen, et al., *Lab Chip*, 16:3394-3414 (2016)). This last property has led to the use of thin PMDS membranes in extracorporeal membrane oxygenators (ECMO) used in medical contexts to oxygenate blood (Gimbel, et al., *Lab Chip*, 16:3227-3234 (2016); Hoganson, et al., *Lab Chip*, 11:700-707 (2011)).

PDMS is a versatile elastomer that is easy to mold (and thus highly amenable for prototyping), has good optical properties, and is oxygen permeable. Hydrophobic compounds including steroid hormones and many drugs may exhibit partitioning into PDMS, thus precluding quantitative analysis and control of drug exposures (Toepke M W, et al., *Lab Chip*, 6:1484-1486 (2006)).

In preferred embodiments, the fluidic plate is fabricated from polysulfone (PSU). PSF is a rigid, amber colored, machinable thermoplastic with food grade FDA approval (21CFR177.1655) and USP Class VI biocompatibility. It is generally resistant to a wide range of chemical solvents, can be autoclaved, and is commonly used for instrumentation and medical devices. PSU also has dramatically lower surface adsorption and almost no bulk absorption of hydrophobic and lipophilic compounds (Ng S F, et al., *Pharmaceutics*, 2:9-223 (2010)).

All fluidic surfaces of the platform may be passivated prior to each experiment using serum albumin to further reduce the binding of biological molecules or drugs in the platform. The fluidic plate may also be cleaned and reused as many times as needed.

The top fluidic plate may be machined from a monolithic block of selected material, e.g., polysulfone (PSU) plastic, to include one or more replicate lanes, with each replicate lane including at least one compartment selected from the group consisting of media reservoir, oxygenator, spillway, and effluent collection. Microfluidic channels and pumps are machined into the underside of the fluidic plate to convey fluid from the MPS well or oxygenator. The individually addressable micro-pumps are fabricated in-line with the built-in fluid channels, and may be based on a 3-chamber, peristaltic pump-pump-pump design or a valve-pump-valve design. Additional pumps under each well provide recirculation flow, reducing nutrient and oxygen gradients within each compartment.

B. Methods of Making

The platforms may be fabricated through molding, machining, and sterilization processes. A monolithic surface micromachined fluidic plate is preferred. It provides reliable performance and it is easy to clean. All fluid contacting surfaces are accessible for cleaning. All components have relatively long life time, and no delamination occurs in sterilization processes such as autoclave. Pneumatics can be easily cleared of condensation. Generally, the platform uses only two plate components bonded together, such that all pneumatic channels occupy the same plane within the plate. Inlets may be stacked by interleaving their channels and using drilled features to connect the inlets at different vertical positions to the channel layer, thus packing them more densely on the side face of the manifold.

The turnaround cycle for modularized computer-aided design (CAD) and machining is relatively quick. It is easy and rapidly customizable according to user's individual needs. Computer numerical controlled (CNC) machines, such as lathes and mills, may be used to manufacture the components of the platforms.

C. Techniques for Assembly and Bonding

The fluidic plate, pneumatic plate, and membrane (in sterilization bags) are generally assembled in a biosafety cabinet. Before assembly, a sterile microplate lid is generally taped onto the fluidic plate to protect the sterility of the cell culture region. The layers can then be assembled upside down to aid with visual alignment through the acrylic plate. Once the alignment pins mate with the fluidic plate, the platform can be carefully removed from the cabinet, keeping pressure to maintain the seal between the plates. Screws can be inserted and tightened in a nonsterile environment as long as the plates are not separated. Two fully assembled platforms can be daisy chained by connecting them with short lengths of tubing connecting straight across to the corresponding ports. Daisy chained platforms are most easily transported with a large metal tray.

Platforms are assembled at a few days (e.g., 4 days) prior to the start of cell-culture experiment of interest. Surface passivation (priming) of sterile platforms can be conducted with 1% BSA and penicillin-streptomycin in PBS in volumes appropriate to each compartment. Pump function and tubing connections can generally be visually confirmed by pumping from the mixer to each dry compartment, then by running the recirculation pumps backwards to clear all air from the channels. Spillways can be manually wetted with small volumes to ensure spillway operation. Platforms are usually run overnight in the incubator to passivate and confirm full operation before the addition of cells.

In some embodiments, fluidic plates are bonded to create closed fluidic paths using a sintering method between plastic plates of specific pointedness.

In some embodiments, polyurethane (PU) membranes between about 20 and 200 microns thick, preferably between 50 and 100 microns thick, such as 50 microns thick, may be stretched on tension rings to maintain a constant tension. They can be laser cut with the corresponding pattern of screw holes on the pneumatic plate, if screw holes are present to align the top plate with the pneumatic plate.

A membrane diaphragm (optionally containing elastomer in regions corresponding to the pump and valve of the pneumatics) can be stretched between the pneumatics plate and the plate for the fluidic culture, and pressed to adhere to the pneumatic plate. In some embodiments, automation is used to attach the membrane to the fluidic plate.

Alternatively, elastomer patches may be used on the membrane layer to create seals and hermetic pathways in fluidic plates. Elastomer material may be used only at regions of a membrane or a patch corresponding to pneumatic pump and valves. Membranes containing elastomer patches can be prepared ahead of time and kept sterile for assembly of the chip. This would facilitate the assembly and operation of organ-on-chip plates where an elastomer is deflected to create a pumping action only in localized regions of the plate. A wide range of elastomer types and thicknesses may be applicable.

D. Surface Treatment to Control Wettability

Surface patterning may be used to control wettability of open fluidic passages in the organ-on-chip platforms. Machining patterns include zebra (linear), shark, concentric, and smooth surfaces.

The use of different machining processes and micro texturization can dramatically affect wettability of culture plates for organs-on-chips. For example, a surface finish may significantly modify polysulfone wettability up to about a 40° change in the contact angle with water or a cell-culture media. Incubator conditions may also increases wettability to a slight extent of about 2-3° difference. It may be preferable for mesofluidic devices to have an increased wettability in order to improve the performance.

In general, dark polysulfone is more hydrophobic than light polysulfone. Selection of different grades of polysulfone provides another means to vary the wettability of the plates.

E. Sterilization

One or more sterilization procedures may be performed on the cell-culturing fluidic plate, the actuation membrane, and optionally the pneumatic plate. Sterilization techniques include gas treatment (e.g., ethylene oxide), ionizing radiation, sonication, surface treatment (e.g., surfactant), and autoclave.

Generally before use, the top plate (e.g., polysulfone top plate) is cleaned and sterilized. First, the plate can be submerged in about 10% bleach for about 30 to 60 minutes, followed by a short rinse in distilled water. A residue-free surfactant may then used to remove any remaining contaminants by sonicating, submerged in about 10% solution (e.g., 7× solution, MP Biomedicals #MP0976680HP) for about 15 minutes. Two subsequent 15-minute sonication cycles in fresh deionized water may follow to remove all surfactant before a final deionized water rinse. The plate may then be air dried, sealed in a sterilization bag, and autoclaved.

Generally, the pneumatic plates do not require formal sterilization, but prior to assembly they may be wiped thoroughly with a wipe sprayed with 70% ethanol to remove any dust or particles from the sealing areas that contact the membrane.

Pneumatic actuator membranes may be rinsed in about 10% 7× solution and with excess deionized water. Generally, an ethylene oxide gas sterilization step follows after the membranes are air dried, and the membrane is allowed 24 hours to degas in a chemical fume hood.

IV. Methods of Using the System

In vitro to in vivo translation (IVIVT) is an interpretive step that compares and validates MPS results to clinically-relevant outcomes. The apparatus may be applied with the IVIVT method in assessing additional factors such as endogenous growth factor, inflammatory and hormone signals in the prediction of pharmacokinetics and pharmacodynamics (PK and PD). Compared with in vivo to in vitro correlation (IVIVC) and in vivo to in vitro extrapolation (IVIVE) methods in the prediction of PK, IVIVT goes a step further to include analysis of these additional factors and thus additionally predict PD, clinical toxicology, biomarkers, and patient stratification using information from MPS technologies. Combined with physiologically-based PK (PBPK) models for IVIVT, the platforms provide an improved quantitative forecast on human responses to test agents, taking into accounts missing organs, organ and media size mismatches, and drug exposure.

In some embodiments, the system can also be used to exemplify diseases or disorders. For example, the platforms may be used to establish micro-metastases in the context of a relatively large (about 1 million cells or less) mass of liver cells, and then to analyze complex cell-cell communication network signatures using both measurements that can be routinely made in patients (on the circulating medium) as well as measurements that cannot also be made on patients—the kinetics of tumor cell growth and death.

A. Preclinical Drug Discovery

The platforms typically support survival and functional culture of one or more organs on the chip for an extended period of time such as days, two, three, four, five weeks, two months, three months, or longer. Long-term multi-organ cultures are particularly advantageous for studying the pharmacology of low-clearance drugs, supporting repeated drug exposures, analyzing drug-drug interactions, and modeling chronic diseases.

The platform can be used for target identification and validation, target-based screening, phenotypic screening, and other biotechnological applications.

Cell and media volumes provide enough signal for commercial assays such as ELISAs and high-content, multiplexed assays.

Multiple-omics measurements across the scales of information flow in cells, from DNA to RNA to protein, protein activity states, and metabolites, as well as similar types of analysis of patient-derived immune cell function.

Although standard culture systems are reasonably effective for most small molecule drug PK assays, a vast number of diseases lacking adequate therapies have inflammation implications and are not well represented or modeled in standard culture systems. The platforms may be particularly suitable for later stages of drug development that generally involves the immune system.

The platforms may recapitulate a complex immunologically-based drug-drug interaction between the anti-IL6 receptor antibody, tocilizumab, and the metabolism of simvastatin—a phenomenon that could not be reproduced in standard cultures (Long T, et al., *Drug Metab Dispos* 44, 1940-1948 (2016)). A wide range of drug agents (small molecules, peptide, proteins, nucleic acid, etc) may be tested in the apparatus for medicinal, cosmetic, or scientific applications.

Agents are selected based on the disease or disorder to be treated or prevented.

B. Cells and Tissues

Differentiated cell types and specialized cell types such as stem cells and paneth cells, as well as microbiome for some embodiments such as gut MPS, may be added to the platform.

The microphysiological systems (MPSs) supported by the platform may comprise primary cells, cell lines, pluripotent stem cells, progenitor cells, organoids, or any combination of mammalian or non-mammalian cells seeded on the scaffolds.

Three-dimensional tissues comprising multiple cell types on a scaffold designed to distribute flow through the tissue may also be used.

Other cell lines or cell types may be added dependent on use. The MPS system and the subcomponents may be used for in vitro culturing of cells and tissues with high oxygen demand, or for in vitro culturing of cells and tissues that would benefit from continuous supply of fluid at a constant oxygenation level. Cells and tissues with high oxygen demand include hepatocytes and liver tissues, muscle cells and tissues including cardiomyocytes and cardiac tissue, neuronal cells and tissues, and blood cells and tissues, such as lymphocytes.

The most overwhelming biological design constraint for in vitro liver bioreactors is meeting the basic metabolic demands of the cells or tissue. Oxygen tension is a controlling factor in many aspects of liver phenotype varying along the sinusoid from 85 µM periportal to approximately 45 µM pericentral. Hepatocytes consume oxygen at 10- to 100-fold the rates of most cells, and because hepatocellular function is so intimately linked to oxygen tension there exists an enormous need to balance oxygen consumption with oxygen delivery. In cell culture, oxygen is depleted very quickly compared to other key nutrients like glucose and amino acids, which are present in culture medium at roughly comparable concentrations to those in blood. Each hepatocyte contains over 1500 mitochondria which consume oxygen at a rate of 0.3-0.9 nmol/sec/$10^6$ cells, while the average rate of oxygen utilization by many other cells is about 2-40 picomol/sec/$10^6$ cells. This is an especially substantial challenge in 3D cultures, as the oxygen gradient across a layer of 5 cell diameters, which represents a distance of approximately 120 µm, ranges for liver from normoxic to hypoxic (Ebrahimkhani et al., *Adv Drug Deliv Rev.* 0: 132-157. doi:10.1016/j.addr.2014.02.011 (2014)).

C. Disease and Disorder to be Modeled

The organ-on-chip platforms are a useful tool for disease modeling and drug development, especially in identifying and defining the appropriate "minimal set" of interacting organ systems to represent a disease state.

Drug development for a variety of diseases and/or disorders may be improved utilizing the platforms by culturing relevant tissues or cell types for systemic studies. Complex individual organs-on-chips that capture the local features of disease, especially inflammation, are preferably applicable for modeling systemic diseases or diseases that are associated with multiple organs or involve multiple types of cells. The diseases and/or disorders that may be modeled in the bioreactor include, but are not limited to, cancers/tumors (e.g., tumors in the breast, bones, liver, lungs, and brain), chronic inflammatory diseases (e.g. diabetes, arthritis, endometriosis, and Alzheimer's), non-malignant growth of endometrium outside the uterus (endometriosis) or displaced into the uterine muscle (adenomyosis), abnormal liver functions such as those caused by non-alcoholic fatty liver disease, The system provides a means for exposing the cells to an agent to determine its effect on the cells administering the agent in different dosages, in a different dosing regimen, or in combination with one or more other agents and determining its effect on the cells, as well as wherein the agent is administered to different cell types or cell types associated with one or more diseases or disorders. This allows one to test agents in vitro with human cells under conditions mimicking a human, at least in part, under controlled conditions, looking for effects on other cell types, as well as on the cells one wants to monitor for an effect. This is more rapid, more controlled, and yet not restricted to a single class of cells or tissues.

V. Kits

Kits containing any one or a combination of pre-assembled platforms, sterile lids, pneumatic connectors, tubing, cell culture media, and additives to the cell culture media, are provided. Kits may also include disassembled platforms, wherein the end user assembles the MPS well components provided in the kit. The components include MPS well scaffolds, filters, scaffold support, attachment means, membranes, fluidic plates, pneumatic plates, cell culture fluids, and instructions for assembly.

The kits may also include tools for measuring circulating fluid volume, oxygen concentration, and insertion or removal tools for the attachment means.

The present invention will be further understood by reference to the following examples.

EXAMPLES

Example 1. Oxygenator Design and Testing—Conical SLA Resin Spiral and PSU Spiral Breadboards, and Conical and Elongated PSU Spiral Oxygenators as Revision 1 and Revision 2 Oxygenators Materials, Methods, and Results Designing an open-well system at very low volumes requires careful attention to surface tension effects, which can be difficult to predict by modeling alone. The design process relied heavily on quickly iterating prototypes and breadboard models to test individual components of the system.

The corner flow oxygenation concept was selected for implementation based on the anticipated performance relative to the requirements and anticipated development/manufacturing time as expressed in Table 1. Integration of the oxygenator into the platform itself with no crevices or interfaces requiring adhesive is a significant advantage for sterilization, cell compatibility, and usability.

Two surrogates were used in the process: (1) a 1% bovine serum albumin (BSA) solution in phosphate buffered saline (PBS) was used as a less-expensive substitute for the cell culture medium, (2) and stereolithography (SLA) resin prototypes were plasma-treated to approximate the wetting properties of polysulfone (PSU) (Liston, et al., *Journal of Adhesion Science and Technology*, vol. 7, pp. 1091-1127 (1993)). Polysulfone is highly inert, autoclavable, and minimally adsorbing of a wide range of drug compounds. For these reasons, it has been used in previous platforms (Domansky, et al., *Lab Chip*, no. 10, pp. 51-58 (2010); Edington, et al., *Scientific Reports*, (In Press)) and was chosen as a suitable material for the top plate of the platform. However, it is expensive and time-consuming to fabricate PSU prototypes, and SLA prototyping allowed much faster and less expensive development and testing of prototypes.

To validate plasma-treated SLA as a surrogate prototyping material, an equal volume of BSA solution was pipetted onto the two surfaces and compared.

To evaluate plasma treated SLA (Clear v2 Resin, Formlabs, Somerville, MA) surface as an easily prototyped surrogate for machined polysulfone (PSU), an equal volume of fluid was pipetted onto clean surfaces of plasma treated SLA and untreated PSU. The size of the drop was an indication of wetting, and showed rough equivalence between the two surfaces. The drop on the polysulfone appeared larger, indicating that the contact angle of 1% BSA solution on PSU was lower than that on plasma treated SLA, but they were relatively close, and plasma-treated SLA should work as a prototyping surrogate for observing surface tension effects.

Figure 21:
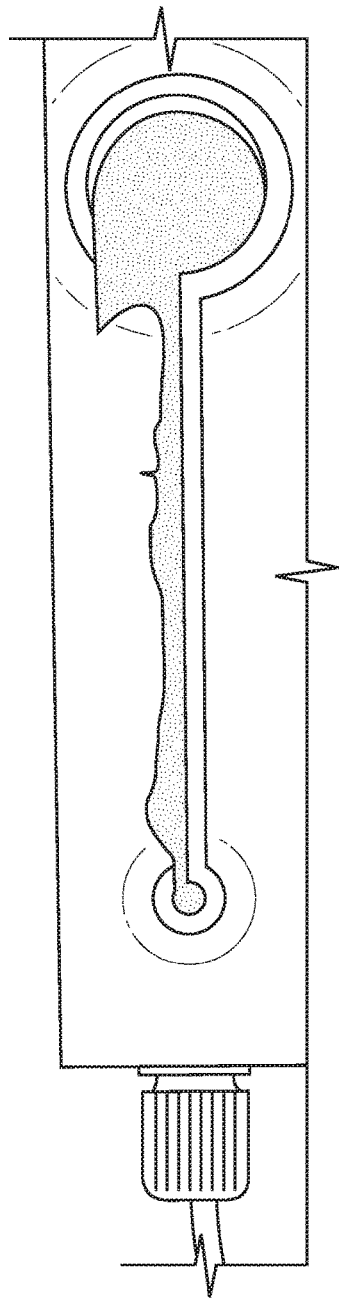
FIG. 21 is a diagram showing a top view of an SLA model generated to evaluate corner wetting behavior. Fluid is introduced through the tube on the left and sinks in the well on the right. The SLA has been plasma treated. Fluid is 1% BSA in PBS with food dye for better visibility.

The simple SLA breadboard model shown in FIG. 21 was an initial tool to assess the scale and viability of flow in a corner as an oxygenator concept. It demonstrated the desired wetting behavior, though not spontaneous capillary filament formation, indicating the contact angle is greater than 45 degrees (Concus, et al., *Proceedings of the National Academy of Sciences of the United States of America*, vol. 63, pp. 292-299 (1969)). Once the channel was wetted, fluid traveled in the conduit formed by the corner and the free surface, as long as fluid was being evacuated from the opposite end. If fluid entered one end without being removed from the other, the free surface expanded out away from the corner and held volume. If the inlet was elevated relative to the outlet by tilting the device, the excess fluid accumulated in the exit well, and the free surface tightened into the corner, due to the pressure drop $\rho g h$ across the channel.

Oxygenator Design—SLA and PSU Spiral Breadboards

One challenge involved with achieving adequate oxygenator length on a small platform was how to change the flow-path direction to allow tight packaging. Switchbacks were considered, but the additional exposed surfaces at the switchback corners may spread fluid into other regions or create fluid instabilities at the corner. A spiral configuration resolved this challenge by maintaining an approximately straight path if the curvature of the spiral is significantly larger than the curvature of the fluid free surface. An interior spiral breadboard from stereolithography (SLA) resin was manufactured, plasma treated and evaluated, but an exterior spiral was chosen for two primary reasons. First, with an interior spiral, the cell culture well must sit within the bounds of the spiral, or a secondary collection pool at the base of the spiral must be pumped into the well. It is thus difficult to have passive emptying into the well. Second, if the interior curve is made too tight, fluid pools at the corner as described by the Young-Laplace equation, increasing the diffusion length. For an exterior corner, the path curvature at the corners is negative relative to the fluid interface curvature, and the Young-Laplace equation forces the radius of curvature of the fluid free surface to become smaller, shortening the diffusion length (see Example 3).

An exterior spiral SLA resin breadboard was formed and plasma treated for 1 min to approximate the wetting properties of polysulfone. There was undesired accumulation at the exit caused by stable wetting in the exit channel. Because there was a feature at the bottom of the spiral that allowed fluid to accumulate, the fluid profile was significantly thicker at the base than at the top. This was resolved by including a wetted exit ramp into the cell culture well that provided a continuous fluidic connection to a region at a lower pressure head, thereby evacuating excess fluid from the oxygenator flow path (FIG. 22).

Figure 22:
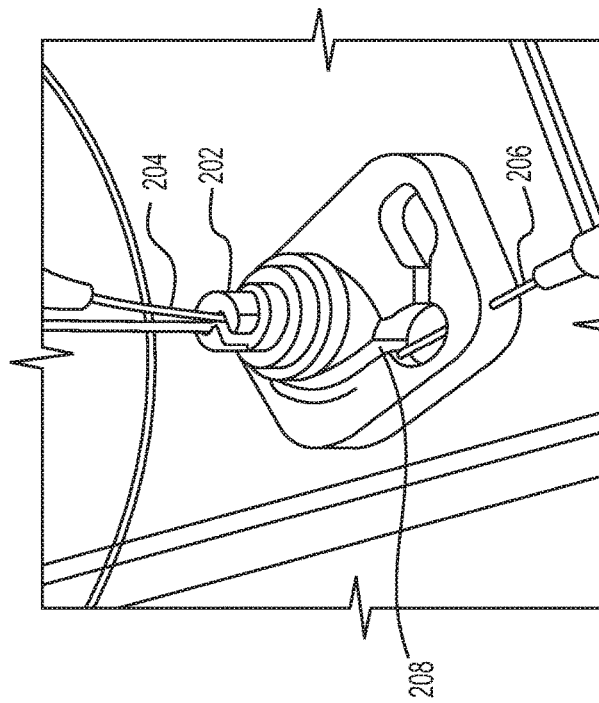
FIG. 22 is a diagram showing perspective views of SLA resin exterior spiral breadboard.

Once the fluid behaved as desired, the oxygenation potential of an exterior spiral breadboard model was measured using probes (810 μm needle probes, Lucid Scientific, Atlanta, GA) placed at the inlet and outlet (FIG. 22).

A polysulfone spiral oxygenator (PSU spiral) was also fabricated to validate plasma treated SLA as a surrogate, and to present any issues caused by machining the spiral. The PSU spiral oxygenator had a height of 16 mm, and the corner channel had a radius of 0.5 mm as machined by the cutting tool. The oxygenator exit region was cut away to facilitate manufacturing and to enable the fluid to spill out into a wide plate rather than backing up into the oxygenator. Data presented in Example 3 show the similarity between SLA and PSU spiral performance, and validate plasma treated SLA as a surrogate prototyping material Revision 1 and Revision 2 Oxygenators The next oxygenator iteration, on the revision 1 platform (FIG. 23), was shorter in height (8 mm) than the previous spirals, in order to reduce the platform height and the thickness of raw polysulfone stock needed for manufacture. This compressed spiral showed an oxygenation potential similar to the taller PSU spiral discussed in Example 3.

For packing multiple replicates on a single platform, it is easiest to have the pump geometry in the same position across all replicates, allowing the pneumatic channels to run straight across the platform without crossing. The spiral was adapted to an elongated format to facilitate packing replicate loops on the same platform. This SLA model also includes small grooves around the curves intended to facilitate wetting, but which instead seemed to prevent effective emptying. The fluid has backed up at the curve, preventing the corner from filling down-stream. This first SLA breadboard included narrow guidance grooves around the oxygenator curves, intended to facilitate wetting upon initial startup of the oxygenator.

The revision 2 oxygenator was a spiral oxygenator elongated to facilitate packing multiple replicates on the platform, and was 4 mm in height, half the height to reduce the cost of the raw polysulfone stock needed to machine the platform.

TABLE 1

Decision matrix for oxygenator concept selection.

| | A[#] | B | C | D | E | F | G | H | I |
|---|---|---|---|---|---|---|---|---|---|
| Cell/drug compatibility | 0 | + | + | + | 0 | + | 0 | − | + |
| Vol < 500 µL | 0 | 0 | − | − | + | 0 | − | − | − − |
| Sterilization/ usability | 0 | ++ | ++ | ++ | 0 | + | − | + | ++ |
| Fit with pneumatic infrastructure | 0 | 0 | 0 | 0 | 0 | 0 | − | 0 | 0 |
| φ > 0.8 @ 1 µL/s | 0 | + | + | 0 | + | + | 0 | + | + |
| Bubble Clearing | 0 | ++ | ++ | 0 | ++ | + | 0 | + | + |
| Resume after 5 min | 0 | − − | − − | − | − | − | 0 | − − | 0 |
| Volume-limiting | 0 | − | − − | − − | − | − | − | − − | − − |
| Manufacture complexity | 0 | + | + | + | 0 | − | − | − | + |
| Robustness | 0 | − | − − | − | − | − − | 0 | − − | − |
| Cost | 0 | ++ | ++ | ++ | + | ++ | + | 0 | ++ |
| Development risk | 0 | + | + | + | 0 | − | − | − − | 0 |
| Total | 0 | +6 | +3 | +2 | +3 | 0 | −5 | −8 | +3 |

[#]membrane oxygenation is taken as the standard, and the anticipated performance of each oxygenator is ranked as much better (++), better (+), the same (0), worse (−) or much worse (− −) than a membrane oxygenator against the functions and attributes listed at left. The total scores for each oxygenator indicate the appropriateness of pursuing each.
A—membrane oxygenator,
B—internal corner,
C—External Corner,
D—Channel,
E—Filament,
F—Gap,
G—Droplet,
H—Surface modification, and
I—Barriers.

Example 2. Revision 2 Oxygenator

Materials and Methods

After further SLA validation of the wetting characteristics of an elongated spiral oxygenator without guidance channels, the revision 2 platform was machined from polysulfone (FIG. 3). This oxygenator was 4 mm in height, half the height of Rev 1 oxygenator (8 mm), and one fourth the height of the PSU spiral breadboard (16 mm). Each lane was surrounded by a barrier to prevent cross-contamination. The flat surfaces were sloped so as to empty to the end of the oxygenator, and the radius at the base of the barrier walls was large enough to prevent fluid accumulation.

To oxygenate the media through a free air-liquid interface while constraining the fluid path and limiting the volume that can collect in the oxygenator, a spiral oxygenator was developed that captured the fluid in the corner of a spiral cut into the hydrophilic polysulfone, as shown in FIG. 3. The corner served to limit the maximum thickness of fluid that oxygen must diffuse into, and the spiral provided enough length in a small footprint for the fluid to exit the spiral adequately oxygenated.

Results

The revision 2 of the Six-replicate Reduced-volume (6×2R) oxygenator performed better or the same as the LIVERCHIP®, and with better control of the fluid at less than a quarter, and approximately one eight, of the volume held in the LIVERCHIP® oxygenator. For example, the fluid volume in the LIVERCHIP® oxygenator is about 400 µL, with a total circulating volume of about 1.2 mL. Instead, the fluid volume in the revision 2 oxygenator is between about 10 µL and about 50 µL, with a total circulating volume in the lane of about 500 µL.

The oxygen concentration that actually reaches the cells, however, depends the flow direction. For downward flow, a conservative fully mixed model suggests that the oxygen concentration going to the cells in steady-state will be a maximum of 125 µM, which may not reach 150 µM. After 8 hours, when upward flow begins, an experiment with the revision 1 6×R prototype indicated that the 150 µM concentration was met and oxygenation was better than on the LIVERCHIP® for the remainder of the experiment.

Example 3. Measuring Oxygenator Performance

Materials and Methods

Analytical Modeling

An analytic modeling for predicting oxygenator performance and highlighting its dependence on various physical parameters was used as follows. The model was compared to measured data.

The performance of the oxygenator can be described by an efficiency φ, the oxygenation potential:

$$\phi \equiv \frac{C_b - C_a}{C_{sat} - C_a}, \quad \text{Equation 2.2}$$

where the oxygen concentration difference of inlet ($C_a$) and outlet ($C_b$) is normalized by the maximum possible oxygenation, that is when the outlet is at saturation $C_{sat}$. This parameter allows comparison of oxygenators across experiments, where the input concentration is likely to vary, and is independent of cell oxygen consumption activity. Further, it can be directly measured with a probe each at the oxygenator inlet and outlet.

The analysis that follows expresses this oxygenation potential in terms of relevant parameters of the system: flow rate Q, diffusion depth h, air-liquid interface area A, and the diffusion coefficient $DO_2$. It may be assumed that plug flow, which requires that (1) there is no diffusion in the direction of advection, i.e. down the length of the oxygenator channel and also that (2) the velocity field is uniform. The validity of the first assumption may be checked by estimating the Péclet number, Pe, which compares the advective transport rate to the diffusive transport rate in the direction of advection (Asano, *Mass transfer: from fundamentals to modern industrial applications*. Weinheim; Wile-VCH, 2006). The Péclet number is often expressed as $$Pe_L \equiv \frac{adv.\ rate}{diff.\ rate} = \frac{LU}{D} \quad \text{Equation 2.3}$$

where U is a characteristic velocity, L is a characteristic length, and D is a diffusion coefficient. For the oxygenator its value using order-of-magnitude values was estimated: the characteristic velocity is the flow rate Q≈1 µL/s divided by the fluid cross sectional area Acs≈1 mm², L≈100 mm is the length of the oxygenator, and $DO_2=3\times10^{-3}$[mm²/s] is the diffusion coefficient for oxygen in water at 37° C. The Péclet number is then $$Pe_L = \frac{LQ}{D_{O_2} A_{cs}} \approx 10^4 \quad \text{Equation 2.4}$$

which indicates that advective transfer dominates, and diffusion along the length of the oxygenator is negligible. In later calculations a different Péclet number, Peh, was used, which addresses diffusion perpendicular to advection, while PeL is only used here to validate the plug flow assumption that diffusion in the direction of advection is negligible.

Considering the diffusion of oxygen into a plug of fluid over time through the surface ΔA in FIGS. 24A and 24B. Fick's First Law (Asano, *Mass transfer: from fundamentals to modern industrial applications*. Weinheim; Wile-VCH, 2006) relates the transport rate of a species across a boundary to the concentration gradient at the boundary. In one dimension, this is expressed as $$J = -D_{O_2} \frac{dC}{dx} \quad \text{Equation 2.5}$$

where J is the mass flux across the surface in [mol/mm²s] and C is the concentration in [mol/mm³]. The units of µM, equivalent to [µmol/L], are used below. At that point, the units of concentration will be set by the boundary conditions and µM is more convenient. While here [mol/mm³] was used to match the relevant length dimensions.

Figure 25A:
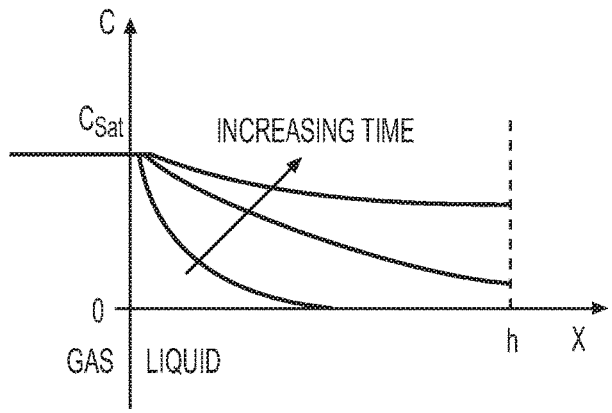
FIGS. 25A and 25B are graphs showing the change in oxygen concentration.
Figure 25B:
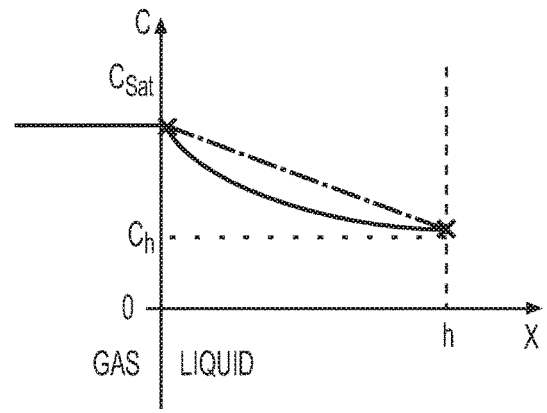

To find total oxygen entering the plug volume, the oxygen flux at the airliquid interface is needed. As a first approximation, the concentration gradient may be linearized as shown in FIGS. 25A and 25B. The oxygen flux at the surface is $$J|_{x=0} = -D_{O_2} \frac{dC}{dx}\bigg|_{x=0} \approx -D_{O_2} \frac{C_h - C_{sat}}{h} \quad \text{Equation 2.6}$$

where Ch is the oxygen concentration at the wall (x=h) of the oxygenator opposite the gas-liquid interface (x=0), and the flux is in the direction of decreasing concentration. The linear concentration gradient that was assumed to mean that the oxygen transport rate at the interface is the same as at the wall, and can be written $$J = \frac{\dot{n}}{\Delta A} \quad \text{Equation 2.7}$$

where $\dot{n}$ is the species transport rate in [mol/s] and ΔA is the area in [mm²] of the gas-liquid interface for the individual plug. A mean concentration Cm may be defined as the quantity of species n [mol] in the system divided by the volume V [mm³]:

$$C_m = \frac{n}{V} = \frac{2n}{\Delta A h} \Rightarrow J = \frac{\dot{n}}{\Delta A} = \frac{h}{2} \frac{dC_m}{dt}. \quad \text{Equation 2.8}$$

With a linear concentration gradient, $$C_m = \frac{C_h + C_{sat}}{2} \Rightarrow C_h = 2C_m - C_{sat}. \quad \text{Equation 2.9}$$

Using J in (2.8) and substituting 2.9 into (2.6), the following may be obtained:

$$\frac{h}{2}\frac{dC_m}{dt} \approx -D_{O_2}\frac{C_h - C_{sat}}{h} \quad \text{Equation 2.10}$$

$$-\frac{h^2}{2D_{O_2}}\frac{dC_m}{dt} = (2C_m - C_{sat}) - C_{sat}$$

$$\frac{dC_m}{dt} + \frac{4D_{O_2}}{h^2}C_m \approx \frac{2D_{O_2}}{h^2}C_{sat}.$$

Solving the differential equation in (2.10):

$$C_m \approx A_1 e^{-\frac{t}{\tau_D}} + A_2 \quad \text{Equation 2.11}$$

where A1 and A2 are constants and $\tau_D = h^2/4D_{O_2}$ is the time constant of diffusion. Applying the boundary conditions $C_m = C_o$ at t=0 and $C_m = C_{sat}$ as t→∞ gives $$C_m \approx (C_o - C_{sat})e^{-\frac{t}{\tau_D}} + C_{sat}. \quad \text{Equation 2.12}$$

Rearranging, gives $$C_m \approx -(C_{sat} - C_o)e^{-\frac{t}{\tau_D}} + (C_{sat} - C_o) + C_o \quad \text{Equation 2.13}$$

$$(C_m - C_o) \approx (C_{sat} - C_o)\left(1 - e^{-\frac{t}{\tau_D}}\right)$$

$$\frac{(C_m - C_o)}{(C_{sat} - C_o)} \approx \left(1 - e^{-\frac{t}{\tau_D}}\right).$$

Equation 2.13 describes the time evolution of the mean concentration of a single plug. If this plug enters the oxygenator at an initial mean concentration $C_o=C_{in}$, it will exit at $C_m=C_{out}$ after a residence time $t=\tau_a=L/U$. At the exit of the oxygenator, $$\frac{t}{\tau_D} = \frac{\tau_a}{\tau_D}.$$
Equation 2.14

Recalling the definition of the oxygenation potential (equation 2.2), and using 2.14, equation 2.13 becomes:

$$\phi \equiv \frac{C_{out} - C_{in}}{C_{sat} - C_{in}} \approx \left(1 - e^{-\frac{\tau_a}{\tau_D}}\right).$$
Equation 2.15

The residence time τa can be estimated by referring to FIGS. 24A and 24B. For a triangular oxygenator, $$A = Lw$$
Equation 2.16

$$A_{cs} = \frac{1}{2}hw = \frac{hA}{2L}$$
Equation 2.17

$$U = \frac{Q}{A_{cs}} = \frac{2LQ}{Ah}$$
Equation 2.18

$$\Rightarrow \tau_a = \frac{L}{U} = \frac{hA}{2Q}.$$
Equation 2.19

To relate this residence time $\tau_a$ to the diffusion time constant $\tau_D$, Péclet number $Pe_h$ was used, which refers to the rate of diffusion orthogonal to the direction of advection to a depth h (while $Pe_L$ used above refers to diffusion in the direction of advection to a length L). This $Pe_h$ captures how much or how little diffusion can occur in the time that the fluid plug travels through the oxygenator, and depends on the flow rate Q, system geometry as represented by h/A, and diffusion coefficient $DO_2$:

$$Pe_h = \frac{adv.\ rate}{diff.\ rate} = \frac{1/\tau_a}{1/\tau_D} = \frac{\tau_D}{\tau_a} = \frac{Qh}{2D_{O_2}A}.$$
Equation 2.20

The flow rate is on the order of 1 μL/s, and the lengths are on the order of 1 mm. Note that for a rectangular oxygenator with $A_{cs}$=hw and A=wL, the Péclet number is also $Qh/2DO_2A$.

Substituting this modified Péclet number into equation 2.15 gives an expression $$\phi = \frac{C_{out} - C_{in}}{C_{sat} - C_{in}} \approx \left(1 - e^{-\frac{1}{Pe_h}}\right)$$
Equation 2.21

To describe φ in terms of a mean concentration that is integrated over the profile, a model described by Glicksman and Lienhard for heat transfer applications may be used (Glicksman, *Modeling and Approximation in Heat Transfer.* New York: Cambridge University Press, 2016). For diffusion into a bulk slab, the first term of a Fourier series to approximate the concentration profile may be used (see Fourier model below). This model relates the normalized mean temperature, or in this case concentration, to the dimensionless Fourier number, which describes the ratio of diffusive transport to storage rate. In mass transfer, for characteristic time t and length h, $$Fo_m = \frac{D_{O_2}t}{h^2}$$
Equation 2.22

At the end of the oxygenator, $t=\tau_a$. Thus, approximating the triangular geometry as a slab of thickness h/2 and using equation 2.19 yields $$Fo_m = \frac{D_{O_2}}{h^2}\frac{hA}{2Q} = \frac{DA}{2Qh}$$
Equation 2.23

Using tabulated coefficients for the slab geometry, the oxygenation potential may be expressed as $$\phi = \frac{\overline{C} - C_o}{C_{sat} - C_o} = 1 - 0.8106e^{-2.47Fo_m}$$
Equation 2.24 where $\overline{C}$ is the spatially averaged concentration in x from the free surface down to x=h.

The measured values of φ for revision 2 decrease more with increasing flow rate than either model predicts if h/A is held constant. This is in contrast to the models based on the PSU spiral measured geometry, where φ was calculated using an h/A value that was specifically measured for each flow rate. As the flow rate increases, the cross sectional area, the radius of curvature, or both must increase to compensate for the higher flow rate. This can be illustrated by combining the Young-Laplace and Bernoulli equations, where the two reference points for the Bernoulli equation are taken one at the top of the oxygenation spiral and the other in the fluid well where the pressure is atmospheric and the velocity is negligible. The Young-Laplace equation can be further simplified by assuming a straight path, where the radius of curvature in the top plate $R_x \rightarrow$inf. Expressing the velocity as $Q/A_{cs}$ then gives equation 2.27 (note that $A_{cs}$ is a function of $R_y$ and the fluid path width):

$$\Delta P = \gamma\left(\frac{1}{R_x} + \frac{1}{R_y}\right)$$
Equation 2.25

(Young-Laplace Equation), $$(P_1 - P_2) + \frac{\rho}{2}(v_1^2 - v_2^2) + \rho g(h_1 - h_2) = 0$$
Equation 2.26

(Bernoulli Equation), $$-\frac{\gamma}{R_y} + \frac{\rho}{2}\frac{Q^2}{A_{cs}^2} + \rho g\Delta h = 0$$
Equation 2.27 where ΔP is the pressure difference in [Pa] between the two sides of the interface, γ is the surface tension of the interface in [N/m], and $R_x$ and $R_y$ are orthogonal radii of curvature of the surface (see FIG. 26). In 2.26, ρ is the fluid density in [kg/m³], and g=9.8[m/s²]; $P_{1,2}$ are the pressures in [Pa], $v_{1,2}$ are the average fluid velocities in [m/s], and $h_{1,2}$ are the heights in [m] at points one and two in the system.

In practice, the free surface is observed to flatten out at higher flow rates, with a slight increase in the fluid path width until it is limited by the oxygenator edge. As the free surface changes from concave to flat, exposed surface area is decreasing as the diffusion length is increasing, so h/A must increase. This would result in a decreased φ as the flow rate increases. This is supported empirically when there is a negative pressure on the fluid from the ρgh height difference, as shown in FIG. 30.

FIG. 28 also shows measurements from the revision 1 spiral. These measurements show a significantly higher oxygenation potential than those of revision 2, though the oxygenator length was similar. Two effects can explain this: a fluid path curved in the top plate and a greater height difference. A convex curved path, by equation 2.25, requires a more concave curvature in the fluid profile. This tightens the fluid path against the corner, decreasing h/A and therefore increasing oxygenation potential relative to a straight path. The greater height difference has a similar effect in decreasing the radius of curvature, a relationship described by equation 2.27.

The relative contribution of these effects can be estimated as follows. Comparing two cases with an equal pressure differential at the interface yields $$\frac{1}{R_x} + \frac{1}{R_y} = \frac{1}{R'_x} + \frac{1}{R'_y} \qquad \text{Equation 2.28}$$

$$\frac{R'_y}{R_y} = 1 + \frac{R'_y}{R'_z} - \frac{R'_y}{R_x} \qquad \text{Equation 2.29}$$

Let $R'_y \approx 1$ mm be the radius of curvature of the fluid profile in the cross sectional plane for a corner-channel that has a radius in the top plane of $R'_x \approx -10$ mm (where curvature is positive if the center is on the air side of the interface, and negative if the center is on the fluid side: see FIG. 26). Comparing to a straight-path oxygenator ($R_x \to$ inf), $R'_y/R_y \approx 0.9$; a change of at most a 10% from this curvature effect may be expected.

To assess the effect of height, rearrange equation 2.27 and compare between two cases, assuming the cross-sectional area stays constant:

$$R'_y - R_y = \frac{\gamma}{\rho g} \left( \frac{1}{\Delta h'} - \frac{1}{\Delta h} \right)$$

approximating $$\Delta h' = 2\Delta h \approx 0.01 \text{ m}$$

$$R_y \approx 0.001 \text{ m}$$

$$\rho \approx 1000 \text{ kg/m}^3$$

$$g \approx 9.8 \text{ m/s}^2$$

$$\gamma \approx 0.06 \text{ N/m}$$

gives $$\frac{R'_y}{R_y} = 1 - \frac{\gamma}{2\rho g \Delta h R_y} \approx 0.4.$$

This indicates that between the two measured oxygenators, the difference in oxygenation potential derives primarily from the height difference, and the curvature effect is relatively minor.

Fourier Number and One-Term Model

The equations describing diffusion of heat through a solid of uniform properties can be used by analogy to characterize mass diffusion. For unsteady heat transfer in one dimension, without heat generation, the temperature profile in a material of uniform thermal diffusivity α is described by the heat equation:

$$\frac{\partial T}{\partial t} = \alpha \frac{\partial^2 T}{\partial x^2} \qquad \text{Equation 2.B1}$$

For mass transfer, the analogous one-dimensional equation without species formation is known as Fick's Second Law:

$$\frac{\partial C}{\partial t} = D \frac{\partial^2 C}{\partial x^2} \qquad \text{Equation 2.B2}$$

where D is the diffusivity of the relevant species in the specific medium ($D_{O_2}=3\times10^{-3}$[mm²/s] is the diffusion coefficient for oxygen in water at 37° C.).

Non-dimensionalizing with the characteristic time τ, depth h, and saturation and initial concentrations $C_{sat}$ and $C_o$ yields $$t^* = \frac{t}{\tau} \qquad \text{Equation 2.B3}$$

$$x^* = \frac{x}{h} \qquad \text{Equation 2.B4}$$

$$\Phi = \frac{C - C_{sat}}{C_o - C_{sat}} \qquad \text{Equation 2.B5}$$

Φ is distinct from φ, the oxygenation potential, and $$\Phi = 1 - \varphi \qquad \text{Equation 2.B6}$$

The non-dimensionalized diffusion equation is then $$\frac{\partial \Phi}{\partial t^*} = \frac{D\tau}{h^2} \frac{\partial^2 \Phi}{\partial x^{*2}} \qquad \text{Equation 2.B7}$$

The non-dimensional cluster $D\tau/h^2$ is known as the Fourier number, notated for mass transfer here as $F_{Om}$. The Fourier number describes the ratio of the diffusive transport rate ($D/h^2$) to the species storage rate ($1/\tau$). For the oxygenator, the relevant time is the advection time constant $\tau_a$ $$Fo_m = \frac{D_{O_2}\tau_a}{h^2} = \frac{D_{O_2}A}{2Qh} = \frac{Dw}{2Qh}L \qquad \text{Equation 2.B8}$$

where A is the gas-liquid interface area, w is the interface width, Q is the oxygenator flow rate, and L is the oxygenator length. The factor of two comes from the triangular cross-section.

Glicksman et al., *Modeling and Approximation in Heat Transfer*. New York: Cambridge University Press (2016) describe the normalized average temperature θ using a one-term approximation of the Fourier series that describes the developing concentration profile for a rectangular slab:

$$\bar{\Theta} = \frac{T - T_\infty}{T_a - T_\infty} = D_1 e^{-\lambda_1 Fo} \qquad \text{Equation 2.B9}$$

where $D_1$ and $\lambda_1$ are coefficients that depend on the Biot number Bi, which describes the ratio of the heat transfer rates outside and inside the medium of interest. In the case of oxygen mass transfer, the rate of oxygen transport through air is orders of magnitude greater than that through water, so the Biot number is essentially infinite, meaning that the concentration at the liquid surface is instantaneously brought to saturation. Similarly to define a normalized average concentration, $$\bar{\Phi} = \frac{\bar{C} - C_{sat}}{C_o - C_{sat}} \qquad \text{Equation 2.B10}$$

where $\bar{C}$ is a concentration spatially averaged from the interface at x=0 to the opposite wall at x=h. Drawing an analogy between $\bar{\Theta}$ and $\bar{\Phi}$, and using the tabulated coefficients of Glicksman et al., 2016, for Bi→∞ and plate geometry, $$\bar{\Phi} = \frac{\bar{C} - C_{sat}}{C_o - C_{sat}} = 0.8106 e^{-2.47 Fo_m}. \qquad \text{Equation 2.B11}$$

Using equation 2.B6 the oxygenation potential of the oxygenator is then $$\phi = \frac{\bar{C} - C_o}{C_{sat} - C_o} = 1 - 0.8106 e^{-2.47 Fo_m} \qquad \text{Equation 2.B12}$$

For a very large Biot number, Glicksman and Lienhard suggest that the one-term approximation is appropriate for a Fourier number above 0.2. For the PSU spiral oxygenator flowing at 1 μL/s, $$Fo_m = \frac{Dw}{2Qh} L \approx \frac{(3 \times 10^{-3})(1)}{2(1)(0.3)} \times L \qquad \text{Equation 2.B13}$$

$$Fo_m = 0.2 \Rightarrow L \approx 40 \text{ [mm]}. \qquad \text{Equation 2.B14}$$

For an oxygenator length of 175 mm, this suggests that the one-term solution is appropriate for approximately 77% of the length.

Calculating Fluid Profile Under Flow

To assess the oxygenation model empirically, the fluid profile under flow (1-4 μL/s) in the incubator (35-37° C. during measurements) was measured using a Dyno-Lite USB microscope (AnMo Electronics Corporation, TWN). The images were processed using ImageJ software, as shown in FIGS. 27A-27E. Because the profile varied with height, the h/A values from position C were used in calculating the PSU Spiral values in FIG. 28.

Measuring Oxygenation Potential of Revision 1 Oxygenator

To measure the oxygenation potential, deoxygenated BSA solution was flowed through the oxygenator, and the dissolved oxygen concentration was measured at the inlet and outlet. The oxygenation potential, φ, was then calculated using equation 2.2. A 1% bovine serum albumin (BSA) in phosphate-buffered saline (PBS) was deoxygenated by bubbling nitrogen in a glass container. The media was then pumped through PEEK tubing (1/16 in. OD, 1/32 in. ID) with a pneumatic membrane pump. For subsequent tests, at flow rates higher than 2 μL/s, deoxygenated BSA solution was extracted from the bubbler with a syringe and flow was controlled using a syringe pump, as the pump block could not supply these higher flows. Because the oxygenation potential was concentration-independent, the media did not have to be completely deoxygenated at the inlet. Probes were positioned so as to fully immerse the tip in the fluid path. The setup was allowed to sit in the incubator at 37 degrees C. for at least 30 minutes to bring the platform to temperature. The media had sat in the incubator for 1-2 additional hours to deoxygenate and come to temperature.

The BSA was then pumped through a pump block and to the top of the spiral, where probes at top and bottom measure the dissolved oxygen concentration difference.

A simple plug flow model predicts that as the oxygenator length increases for a constant flow rate, the outlet concentration will approach saturation with a decaying exponential as a function of length (see equation 2.21). This was experimentally assessed by probing the oxygen concentration at various locations on the spiral, as shown in FIG. 27E.

The resulting data do show a decaying exponential approach to full oxygenation as the length increases. Between the polysulfone and SLA materials, the difference is minor. The Peclet model uses w=1.5 and h=0.2 measured for position C (FIGS. 27A-27E). Substituting these values into equation 2.21 yields $$\phi \approx 1 - e^{-0.045 L} \qquad \text{Equation 2.30.}$$

The model over-predicted the oxygenation potential.

Measuring Oxygenation Potential of Revision 2 Oxygenator

To test the oxygenation potential of the revision 2 oxygenator, deoxygenated media was first fed from above through PEEK tubing. This setup resulted in dramatic fluctuations in the probe readings due to bubbles at the top of the oxygenator. To resolve this issue, a 1 mm OD stainless steel cannula was inserted in the oxygenator inlet hole from the bottom and fixed in place with a cyanoacrylate adhesive that loosens with isopropyl alcohol (LOCTITE® 4851, Henkel, DEU). Deoxygenated media was allowed to flow through the oxygenator using a syringe pump (Pump 11 Pico Plus Elite, Harvard Apparatus, Holliston, MA). The dissolved oxygen concentration was measured with probes at inlet and outlet.

Measuring Volume of Fluid Captured During Flow

The volume captured during flow is challenging to measure directly. 50 μL pipetted onto a spiral that had been primed with BSA and then dried appeared qualitatively to produce a profile similar to that seen at 2 μL/s, but this was a rough estimate.

When flow at 2 μL/s was suddenly stopped and the fluid immediately aspirated with a pipette tip and massed, a maximum of 12 mg were recovered (12 μL). Neither of these values were definitive, but lacking a better way of measuring the oxygenator volume while it is pumping, they serve as an estimated range. The LIVERCHIP®, for comparison, has an estimated oxygenator volume of 400 μL (1.2 mL total volume, less 50 μL for the retaining ring and scaffold, less 750 μL in the MPS and channels.

The comparison between the volumes of fluid in different regions of a replicate lane with revision 2 oxygenator and those of LIVERCHIP® are presented in Table 2.

Results

FIG. 28 shows predictions of the oxygenation potential $\varphi$ for arbitrary h/A next to measured $\varphi$ values from the LIVERCHIP®, an intermediate prototype, and the final revision 2 prototype. Equation 2.21 shows that $\varphi$ is a concentration-independent characterization of oxygenator performance and depends only on system geometry, oxygenator flow rate, and the diffusion coefficient.

Increasing either h/A or Q decreases $\varphi$; the faster a fluid plug is moving, or the farther the oxygen must diffuse into the system for a given surface area, the farther from $C_{sat}$ the plug will be upon exiting. At these flow rates, the Revision 2 prototype matches LIVERCHIP® oxygenator performance, while the earlier breadboard (PSU_spiral) shows better performance (at the cost of oxygenator height).

As shown in FIG. 28, the model above over-estimates the oxygenation potential. This may be partly due to the linearized concentration profile used to calculate the average concentration $C_m$. As shown in FIG. 25B, a linear profile will always over-predict a mean concentration calculated by dividing the area under the curve by h. As shown in FIG. 25A, the error is particularly large early on in the development of the profile, before the diffusion has reached the distance h.

This one-term approximation model, shown in FIG. 29, better predicts the measured oxygenation potential for the PSU spiral, when the changing h/A values are taken into account. The Rev2 data, however, appear even more divergent than in the Péclet number model when h/A is constant (compare to line 3 in FIG. 28).

The remaining discrepancy between the one-term model and the measured values for the PSU Spiral is small enough to be explained by lack of differences between the true geometry and the approximated slab, the plug flow assumption of a uniform velocity profile, or a combination of the two.

FIG. 31 shows the similarity between SLA and PSU spiral performance, and validate plasma treated SLA as a surrogate prototyping material.

The revision 2 showed an oxygenation potential similar to the LIVERCHIP® at low flow rates, but considerably lower than the earlier breadboards (FIG. 28). This may be due to the smaller Δh (4 mm for revision 2, 8 mm for revision 1, and 16 mm for earlier breadboards).

TABLE 2

Comparison between total circulating volumes of LIVERCHIP ®, revision 2, and closed fluidic systems platforms. Volumes (μL) of fluid in each system at different regions is shown for comparison.

| | Volume (μL) in | | |
|---|---|---|---|
| | LIVERCHIP ® | Replicate lane of Revision 2 oxygenator | Replicate lane of closed fluidic system |
| Oxygenator | 400 | ~50 | 10 |
| MPS and channels | 800 | ~450 | <140 |
| Total circulating | 1200 | 500 | <150 |

Overall, a wide array of free-surface oxygenator concepts, in addition to a standard membrane approach, were tested. Of these, the spiral corner flow oxygenator had the advantages of being robust to disturbances, self clearing, and simple to fabricate as part of the platform itself, improving ease and quality of sterilization. The SLA breadboards were validated to develop these into an elongated spiral oxygenator that performs equivalently to the oxygenation channel on the LIVERCHIP®.

A tighter radius on the fluid free surface yields better oxygenation. How tightly the fluid clings to corner depends on surface and fluid wetting properties, path curvature (spiral versus straight path), and pressure drop from top to bottom which is height dependent. The taller spirals showed better oxygenator performance, but the relationship between the fluid surface radius and the oxygenation was not analytically developed. This modeling, in concert with testing, provides guidance as to how sensitive the configuration is to changes in height, and what the right balance is between performance and additional material cost.

Example 4. Testing Circulation Layouts

Materials and Methods

In-Line Reactor Model

In the existing LIVERCHIP® platform, media flows in a single circuit through the cell scaffold and along a long open well where the media is reoxygenated by passive diffusion. This can be understood with the simple model shown in FIG. 32A. In steady state, $(C_{high}-C_{low})=r/Q$. Using the definition of the oxygenation potential (eqn. 2.21), the steady-state concentrations in the system (where the subscript i indicates the inline model) are $$C_{low,i} = C_{sat} - \frac{r}{Q_i \phi_i} \qquad \text{Equation 3.1}$$

$$C_{high,i} = C_{sat} - \frac{r}{Q_i \phi_i}(1 - \phi_i) \qquad \text{Equation 3.2}$$

Mixed Reactor Model

During downward flow, and for sufficiently high oxygenator flow rates during upward flow, it is assumed that the oxygenator is in a closed loop with a fully mixed chamber at concentration C, which is steadily consuming oxygen at rate r. The input to the oxygenator is therefore C, and the mass transfer into the oxygenator is $\dot{m}O_2=Q(C_{out}-C_{in})$, or $\dot{m}O_2=Q\varphi(C_{sat}-C)$, where $\varphi$ is the oxygenation potential.

The rate of change of mass in the fully mixed system of volume V is balanced by the mass transfer into the oxygenator and the oxygen consumption by the cells:

$$V \frac{dC_m}{dt} = \dot{m}_{O_2} - r = Q_m \phi_m (C_{sat} - C_m) - r \qquad \text{Equation 3.3}$$

Substituting for $\dot{m}O_2$ and solving for concentration C:

$$C_m = \left( C_{sat} - \frac{r}{Q_m \phi_m} \right)\left( 1 - e^{-\frac{Q_m \phi_m}{V} t} \right) \qquad \text{Equation 3.4}$$

The steady-state (t→∞) bulk concentration is therefore $$C_m(t \to \infty) = \left( C_{sat} - \frac{r}{Q_m \phi_m} \right) \qquad \text{Equation 3.5}$$

and the transient response time constant is $V/Q_m\phi_m$. Because this model assumes a fixed oxygen consumption rate r, $(C_{sat} - r/Q\phi)$ can be less than zero; which is clearly non-physical. This error could be mitigated using better model of oxygen consumption kinetics, such as the first-order Michaelis-Menten model (Inman develops this model for the scaffolds used). However, as a hardware design tool to develop a platform that can oxygenate equivalently to the LIVERCHIP® performance, this simplified model is sufficient.

Equation 3.4 allows to see the bulk concentration (and in this model, the concentration entering the oxygenator) in terms of oxygenator flowrate $Q_m$ and oxygenation potential φ. The φ may then be estimated for a given geometry by using equation 2.21.

The steady-state bulk concentration is $C = C_{sat} - r/Q_m\phi_m$. Plotting (FIG. 33) this concentration against flowrate for different geometries (represented by h/A), a range of acceptable flow rate ($Q_m$) and geometry (h/A) combinations may be found that will provide adequate mass transfer (r) without requiring a bulk concentration C below a minimum acceptable lower limit (no less than zero). The solid lines are the mixed model predictions for varying geometries, and indicate that a ratio h/A of below 0.001 would be required at a minimum of 5 µL/s oxygenator flow rate to meet the requirement of 150 µM oxygen concentration flowing to the cells. The dashed lines are model predictions using the measured oxygenation potential values shown in FIG. 28. The mixed model predicts that while the revision 1 prototype at 4 µL/s will meet the functional requirement of 150 µM steady state concentration, the revision 2 prototype will not. However, this may only be the case for the first eight hours of downward flow. The Selective Sourcing Validation Experiment discussed below suggests that during upward flow, the system behaves more like an inline system for oxygenator flow rates near 2 µL/s.

In-Line Versus Mixed Equivalence

Comparing equations 3.2 and 3.5 shows the parameters required of the two systems to achieve equivalent oxygen concentration in the cell environment. In the inline system, the cells experience the high concentration media directly from the oxygenator. In the mixed system, the cells experience a mixed concentration because the freshly oxygenated media is diluted by the bulk concentration in the MPS. Equating the concentration going to the cells in these two scenarios, $$C_{cells,i} = C_{high,i} = C_{sat} - \frac{r}{Q_i \phi_i}(1 - \phi_i) \qquad \text{Equation 3.6}$$

$$C_{cells,m} = C_m = C_{sat} - \frac{r}{Q_m \phi_m} \qquad \text{Equation 3.7}$$

$$Q_m \phi_m = \frac{Q_i \phi_i}{(1 - \phi_i)} \qquad \text{Equation 3.8}$$

Equation 3.8 gives a simple criterion for the desired $Q_m$ and $\phi_m$ of a mixed system required to match the steady-state concentration of a given inline system. Based on the oxygenation potential of 0.8 measured on the LIVERCHIP® at a flow rate of 1 µL/s (the scaffold perfusion flow rate recommended by the manufacturer), equation 3.8 predicts that $Q_m\phi_m = 4$ µL/s is required to match the steady-state concentration observed on the LIVERCHIP® (shown as a dashed line in FIG. 34). Predicted and measured $Q_m\phi_m$ values are shown in FIG. 34. This Figure suggests that h/A four times smaller than that of the revision 2 prototype would be required to reach LIVERCHIP® equivalency. This can also be seen by comparing the predicted concentrations in FIG. 33 to the steady state concentration of 170 µM at 1 µL/s shown in FIGS. 35A and 35B. This reduced h/A could likely be achieved by making the oxygenator four times longer, 2 times taller, or some combination of longer and taller.

LIVERCHIP® Oxygenation Measurement

To measure oxygen consumption rates on the LIVER-CHIP® platform, a custom lid was fabricated that held fiber optic probes (Lucid Scientific, Atlanta, GA) submerged in the tail and 1 mm above the scaffold. To protect the oxygen probes during sterilization, an acrylic shield was assembled.

Rat hepatocytes (250 k) were seeded on the LIVER-CHIP®, and assembled with the custom lid.

Selective Sourcing Validation Experiment

The selective sourcing concept aims to pull media for feeding the cells from under the oxygenator (potentially a high concentration zone), while feeding the oxygenator from the opposite side of the MPS well (potentially low concentration). At very high oxygenator flow rates, the MPS is expected to be fully mixed, but it is difficult to predict at what flow rate that mixing begins to dominate.

To assess the selective sourcing effect, the revision 1 prototype was used. Feeding deoxygenated Bovine Serum Albumin (BSA) solution into the MPS and removing partially oxygenated fluid created a net oxygen mass transfer out of the system, simulating oxygen consumption by the cells (FIG. 36).

A 1% BSA solution in saline (PBS) was deoxygenated by bubbling nitrogen in a glass jar which was vented outside the incubator. A piece of 1/16 in. OD PEEK tubing withdrew fluid from the bottom of the jar, below the bubbling tube to prevent bubbles from being pumped into the oxygenator. A pneumatic diaphragm pump block pumped this deoxygenated fluid into the bottom of the MPS, and withdrew partially oxygenated fluid from the recirculation intake directly under the oxygenator output. Separately, two channels on a second pump block were combined in parallel to flow fluid at 2 µL/s to 4 µL/s into the oxygenator, drawing from the side of the MPS opposite the recirculation intake. Fiber-optic oxygen probes (Lucid Scientific, Atlanta, GA) measured dissolved oxygen concentration at the three locations marked by black arrows in FIG. 36 and also in the deoxygenation jar.

Oxygen Saturation
A. Oxygen Partial Pressure

The partial pressure of oxygen in the incubator—and therefore the dissolved oxygen concentration in the media—depends on ambient total pressure and the partial pressures of other gases present, such as $CO_2$ and water vapor. These calculations assume the media is water, and follow Wenger et al. (Wenger et al., *Hypoxia*, 3:35 (2015)), except that the humidity in the incubators is near 80% relative humidity. The saturation vapor pressure at 37° C. is 6.28 kPa and the room oxygen content is 20.9% by volume (Wenger et al., *Hypoxia*, 3:35 (2015)). Incubator $CO_2$ is regulated at 5%, and atmospheric pressure is assumed to be 101.3 kPa. The water vapor partial and $CO_2$ pressure are therefore $$P_{H_2O_3} = (80\%)6.28 \text{ [kPa]} = 5.024 \text{ [kPa]} \quad \text{Equation 3.9}$$

$$P_{CO_2} = (5\%)101.3 \text{ [kPa]} = 5.065 \text{ [kPa]} \quad \text{Equation 3.10}$$

The balance of the partial pressures is taken up by oxygen and nitrogen, in the same ratio as outside the incubator. The oxygen partial pressure in an incubator at 80% humidity, 5% $CO_2$, 1 atm, and 37° C. is then $$P_{O_2} = (20.9\%)(101.3 - 5.065 - 5.024) \text{ [kPa]} = 19.1 \text{ [kPa]} \quad \text{Equation 3.11}$$

B. Dissolved Oxygen Concentration

Henry's law relates the aqueous concentration $C_{aq}$ of a gas to the partial pressure P by a constant $H^{(cp)}$:

$$C_{aq} = H^{cp} \times P \quad \text{Equation 3.12}$$

This constant $H^{cp}$ is temperature dependent, and can be calculated (Sander, *Atmospheric Chemistry and Physics*, 15(8):4399-4981 (2015)) by $$H^{cp} = H_{ref} \times \exp\left[1700\left(\frac{1}{T} - \frac{1}{T_{ref}}\right)\right] \text{ where} \quad \text{Equation 3.13}$$

$$H_{ref} = 1.3 \times 10^{-3} \left[\frac{M}{atm}\right] = 12.8 \times 10^{-6} \left[\frac{M}{kPa}\right] \quad \text{Equation 3.14}$$

$$T_{ref} = 298[K]$$

The saturated concentration of dissolved oxygen in water at 37° C. (310 K) is therefore $$C_{sat} = 10.2 \left[\frac{\mu M}{kPa}\right] \times 19.1 \text{ [kPa]} = 195 \text{ } \mu M. \quad \text{Equation 3.15}$$

Results

The selective sourcing configuration was chosen as the best compromise between feeding the cells high oxygen concentration and keeping fluid volume low and manufacturing straightforward. The inline concept feeds the cells the highest concentration, but precluded the self-clearing oxygenators considered. The Laminar Figure-8 configuration was promising.

Results from the Selective Sourcing Validation Experiments

In the Selective Sourcing validation experiment, the concentration values measured at the locations shown in FIG. 36 are presented in FIG. 37. The recirculation was flowing upward at 1 µL/s, as it does after the flow reversal at eight hours. Before timepoint A, the oxygenator pump block was flowing at 2 µL/s. Shortly after timepoint A, it began pumping at 4 µL/s. After some initial effects (likely from clearing dead volume), the probes showed an exponential rise to a new steady-state value. The cause of an apparent steady increase at the oxygenator inlet around timepoint B was unknown, but the observed effect was small.

If the system behaves more like an inline system, then the "MPS Out" reading (point 2 in FIGS. 12A and 12B), which the cells would be exposed to during upward flow, should be the same as the oxygenator output, "Oxy. Out" (point 3 in FIGS. 12A and 12B). If, on the other hand, the system behaves like a lumped fully mixed system, "MPS Out" should match the predicted steady state concentration value given by equation 3.5. FIG. 38 shows this comparison at two different flow rates. At timepoint A (2 µL/s), the simulated consumption rate r'=1 [µL/s]×($C_{MPS\ out} - C_{MPS\ in}$) [µM]=178 pmol/s and φ=0.86. At timepoint B (4 µL/s), r'=165 pmol/s and φ=0.73. It appeared that in both cases, the system behaved closer to an inline system at 2 and 4 µL/s, though less so at 4 µL/s. This suggested that the model developed in Mixed Reactor Model was a very conservative lower bound that is more applicable at higher flow rates than at lower ones. Further, while the mixed model assumed in FIG. 34 suggests that higher flowrates yield better performance, these data suggested the opposite occurs at lower flow rates, and an inline model is more appropriate. Because the inline system is more effective, keeping the system in this unmixed regime can yield higher oxygen concentration delivered to the cells. Note that the simulated oxygen consumption rate r' is a function of the "MPS Out" concentration, and therefore different between timepoints.

This simulated oxygen consumption experiment was challenging to perform with the revision 2 platforms because the pumping was on-board and difficult to interrupt. However, because the MPS well geometry was the same between revisions 1 and 2, it was expected that the trend shown in FIG. 38 would hold for revision 2 as well, and at an oxygenator flow rate of 1-2 µL/s, the inline model would give a better prediction of the steady state oxygen concentration of media going to the cells. While using the mixed model would lead to selecting an oxygenator flow rate of 3 µL/s or above, FIG. 39 suggests that if the selective sourcing behaves like an inline system at low flow rates, a flow rate of 1-2 µL/s would in fact give a higher cell feed concentration.

This selective sourcing effect is only expected to occur after during upward flow, when the cell feed pulls from under the oxygenator output. In the first eight hours flowing down through the scaffold, the oxygenator output and deoxygenated media from the cells would flow into the MPS above the scaffold in the same location (as shown in FIG. 12A). The system is therefore likely to behave more like the mixed system, and should be operated at a higher oxygenator flow rate. FIG. 39 suggests 3 µL/s would offer the highest cell feed concentration at 125 µM for the mixed model; this is below the 150 µM, but may be acceptable for a short duration.

Results from the LIVERCHIP® Oxygenation Measurement

The oxygen readings over time from the LIVERCHIP® are shown in FIGS. 35A and 35B. This was a simple pilot test of only one channel to validate the sterilization process of the oxygenation lid and obtain a ballpark Figure for the consumption rates.

1 kPa partial pressure in the incubator environment corresponds to 10.2 µM. Multiplying the concentration differences between tail and scaffold by the flow rates, an oxygen consumption rate of approximately 100 pmol/s was obtained. Two subsequent measurements of 600 k human hepatocytes from two different donors showed a consumption rate of approximately 60 and 80 pmol/s.

Therefore, the selective sourcing concept was chosen as a compromise to balance the fabrication considerations that favored the mixed co-flow concept against the higher concentration achieved in an in-line system for a given consumption rate and oxygenator efficiency. The mathematical models developed to describe the in-line and mixed systems serve to bound the expected steady state concentration going to the cells. Empirical testing with the revision 1 prototype simulating oxygen consumption indicated that for upward flow, the system behaved like an inline system at low oxygenator flow rates. This indicated that the revision 2 system would achieve 150 µM cell feed concentration after eight hours, while not meeting the requirement during the initial downward flow.

Reversible recirculation is achieved by decoupling the oxygenator and recirculation loops, and the degrees of freedom are coupled across replicates as described in Example 1.

Example 5. Design and Testing of Scaffold Attachment Means

Materials and Methods

Testing Apparatus

A test apparatus was built to test the sealing of retaining ring prototypes. Two pockets 10 mm in diameter, one with the sealing land and one without, were CNC machined into polysulfone. A pneumatic connector (L LEGRIS® 3171-53-20, Parker Hannifin, FR) sealed to the polysulfone with an o-ring and connected to ⅛ in. outer diameter (1/16 in. ID) tubing. Retaining rings were tested with a 9.8 mm diameter polyester shim the same thickness as the scaffold (0.10 in.) to simulate a fully occluded scaffold. The machined pockets simulated the MPS well. The pockets were filled with water until an air-water interface was visible in the connected tube, and the retaining ring prototypes were assembled with the usual filter and a solid polyester disc replacing the scaffold to simulate full occlusion. The tube was then lightly pressurized, starting at <1 kPa, and slowly increased to 40 kPa (measured with FLUKE® 717 300G Pressure Calibrator). The air-water interface in the tube was observed to move in two cases: 1) while pressure increased, due to deflection of the polyester disk, and 2) when fluid was leaking. To avoid confounding these two effects, the pressure was therefore maintained static for 60 seconds at discrete pressure intervals to observe movement of the interface due to leaking alone. The inner diameter of the tube was approximately 1/16 in., allowing an estimate of leak rate by measuring the time over which the interface moved a known distance. Interface movements of less than 1 mm were observable, allowing detection of leaking lower than 0.2 µL/s. A hold time longer than 60 sec was used to detect any slower leaks.

Tilting Ring

The tilting ring concept is installed by pushing the outer edge of the top surface downward, where it stays due to friction with the MPS wall. The elastic compression of the inside edge acts as a spring, applying a downward sealing force on the scaffold assembly. Several prototypes were machined to test the efficacy of this approach; the three main profiles explored for the tilting ring concept are shown in FIGS. 40A-40D. For profiles in FIGS. 40B and 40C, the removal clips were omitted for testing purposes.

The tilting ring prototypes were fabricated from high impact polystyrene on a desktop CNC mill (OTHERMILL® Pro, Bantam Tools, Berkeley, CA). CAD and toolpaths were generated in AUTODESK® Fusion 360 (Autodesk, Inc. San Rafael, CA). The primary fabrication challenge was indexing the part between milling operations on opposite faces. The most effective method used for these prototypes, illustrated in FIGS. 40E-40G, was to mill the bottom features on a cylindrical blank from the flat stock, then to press-fit this blank onto a machined post before machining the removal clips on the top. Because the locating post remained fixed after milling, its center was known, and the top features could be machined concentric to the bottom features.

Beveled Ring with VITON® Gasket

An elastomeric sealing solution was developed as a short-term solution for experiments where VITON® was an acceptable material and required better sealing than the LIVERCHIP® retaining ring could provide. The beveled ring with VITON® gasket offers several advantages over the tilting ring described above. First, the tolerances are looser than for the tilting ring concept because plastic deformation is allowable in this case. Second, an axially symmetric design allows fabrication on a lathe, where tight diametric tolerances are easier to maintain. Third, the increased deflection and conformal contact of the elastomer will provide a more reliable seal. The gaskets and ring described below sealed to 40 kPa in the test apparatus described above.

The assembly, shown at right in FIGS. 7C and 7D, consisted of a chamfered retaining ring and a rectangular cross-section VITON® gasket. The chamfered retaining ring design was chosen to direct force on the gasket both downward and radially outward, sealing both possible leak paths around the gasket, while being easier to fabricate than the stepped design shown in FIG. 16A. The ring is chamfered on the top and bottom and can be inserted in either orientation, so the user does not risk inserting it upside-down. The gasket was punched from a 1/64 in. thick VITON® sheet using a custom two-part punch and a 1-ton arbor press. The two-part punch included one short part with larger internal diameter, and one long part with smaller external diameter fitting inside the short part) machined from 4140 Alloy steel. The shorter punch is used first, then the longer punch is inserted inside the shorter one to form the internal diameter of the gasket.

The chamfered retaining ring was fabricated from polystyrene on a lathe with a custom-ground cutoff tool, to an outer diameter of 10.10±0.01 mm. This method was aimed at quickly fabricating the 20 rings needed for pilot experiments; for larger quantities, a Swiss screw machine shop could fabricate these rings to high precision on a six to eight week time-line.

To remove the ring, a tool was fabricated from stainless steel rod. A tool for removing retaining rings from platforms without tweezer pockets includes a long handle and a tip turned about 90° to the main axis of the long handle. The tip is pointed. The pointed tip can either pry under the retaining ring or dig into its inside bore. In the former case, the user must be careful not to gouge the MPS wall. The length of the point and curvature of the heel are such that the point is pushed into the retaining ring, but the heel does not touch the scaffold. Bottom: A simple stainless steel guard ensures that the point does not injure the user during storage and handling, nor perforate the sterilization pouch. While this was a simple and effective solution, it did require user care to avoid damaging the platform itself.

The scaffold support was similar to the LIVERCHIP® support, except that it is a separate component from the platform itself. Separating the scaffold support allowed the bottom of the MPS to be much higher than it is in the LIVERCHIP®. Raising the MPS well helped with passive draining of excess volume—introduced by the media exchange pump—from the MPS into the effluent collection. The LIVERCHIP® does not have automated media exchange, and thus has no spillway, so the MPS height is not a concern on that platform.

The scaffold support was machined from a 1 mm thick polystyrene tissue culture lid (Costal universal lid #3099, Corning Incorporated, Corning, NY) using the OTHER-MILL® Pro (OMC2 LLC, Berkeley, CA) desktop mill. Each face was sanded with 1000 grit sandpaper, and additional deburring was performed with a toothbrush under a stereo microscope. For larger batches, a cryogenic deburring method such as dry ice blasting could be employed.

Results

LIVERCHIP® Retaining Ring

With the testing apparatus in place, the existing retaining ring was observed to leak in excess of 1 µL/s at pressures below 1 kPa, which was the lower detection limit. Because of possible differences in diameters, it is difficult to predict from this test the ring's performance in the actual LIVER-CHIP® platform, but the presence of removal pockets cut into the wall of the well where the LIVERCHIP® retaining ring seals will likely limit any improvement that could be obtained from a smaller diameter well.

The diameter of the pocket is critical to the retaining ring performance, as it determines, for a given ring geometry and friction coefficient, the holding force achievable. To measure the internal diameter, a metrology grade rubber was cast into each pocket, and measured with a micrometer (293-340, Mitutoyo, JP). To avoid compressing the rubber, the diameter was taken when it could no longer slide easily through the micrometer jaws. The pockets with and without the sealing land measured 10.02±0.01 mm and 9.98±0.01 mm, respectively. For machining the pockets, the toolpaths were identical before the final cut to form the sealing land. This final cut put the outer cutting edge of a smaller end mill at the same outer diameter, making a second cutting pass on the same surface, which may be responsible for the small difference in diameters.

Tilted Ring

While the LIVERCHIP® retaining ring is inserted using a tubular punch with a flat bottom, the tilting ring concept requires an insertion tool with a beveled edge to apply force only at the outer edge. For the ring with removal clips, the insertion tool requires clearance pockets, and therefore does not press down on the outer edge in the two locations behind each clip.

The first machining operation resulted in a tilting ring with two clips, which allow removal. The presence of these clips required an insertion tool with clearance notches. A prototype with six clips was also fabricated to evaluate the tilting ring variant. The existing LIVERCHIP® retaining ring consists of a polypropylene annulus with a rectangular cross section.

On first installation of the tilting ring with profile 802 (FIG. 40A), fluid accumulated behind each clip where the insertion tool had not pressed down the outer edge. After pressing the clips radially outward by hand, the ring sealed up to 25 kPa in the test block pocket that included a sealing land, using a standard filter and the polyester scaffold simulator disc. A ring with profile 804 (FIG. 40B), without removal clips, leaked at 5 kPa. This was thought to be caused by the increased bulk and therefore stiffness of the profile. Profile 806 (FIG. 40C), which is less stiff to twisting, sealed up to 25 kPa.

While below the target 40 kPa, this was far better performance than the existing retaining ring exhibits. However, the performance was critically dependent on the extent of interference between the ring and the pocket. The actual interference in these tests was below the set-ups' ability to measure, partly because the rubber cast and retaining rings both deflect when measured with physical means. An optical comparator did not offer the precision needed. To emphasize the risk of these tight tolerances: when the tool was changed from a ⅛ in. end mill to ¹⁄₁₆ in., and the tolerance of linear interpolation was adjusted slightly, rings of the same profile no longer sealed beyond 1 kPa or so. This supported the use elastomeric gaskets for near-term experiments.

The six-clip prototype was built to evaluate whether the twisting of the ring could be accomplished by deflecting the removal clips alone, rather than pushing on the outer edge. This prototype did not seal, likely because the clips were too weak to overcome both the ring stiffness and the wall friction to twist the ring enough that provided a downward force after the clips were relaxed. It may be challenging to achieve the required clip stiffness if the ring is to be a uniform material.

Beveled Ring with VITON®Gasket

The gaskets and ring described below sealed to 40 kPa in the test apparatus described above.

The assembly, shown at right in FIG. 4-1, consisted of a chamfered retaining ring and a rectangular cross-section VITON® gasket. The chamfered retaining ring design was chosen to direct force on the gasket both downward and radially outward, sealing both possible leak paths around the gasket, while being easier to fabricate than the stepped design shown in FIG. 16A. The ring is chamfered on the top and bottom and can be inserted in either orientation, so the user does not risk inserting it upside-down.

The attachment means are some of the many potential solutions to the problem of fluid bypassing the cell scaffold. The retaining ring with a VITON® gasket presented above was developed as a short-term solution to provide significantly better sealing (>40 kPa vs <1 kPa for the LIVER-CHIP® retaining ring). The tilting-ring approach showed promise, sealing to 25 kPa, but is fundamentally limited by the narrow machining tolerances required to prevent plastic deformation.

Example 6. Platform Design, Manufacturing and Testing

Materials and Methods

Revision 2 Platform

The components of the revision 2 platform (6×2R) are shown in FIG. 1. Each of six replicate lanes consisted of a media exchange reservoir, an oxygenator spiral, a microphysiological system (MPS) culture well, and an effluent collection reservoir (FIGS. 2A and 2B). The top plate was CNC machined from polysulfone, with open fluidic features on the top connected through vertical holes to closed passages and pumps on the bottom face. A polyurethane membrane (50 µm Aromatic Polyether Polyurethane film, extruded by American Polyfilm, Branford, CT) separated the top plate from the pneumatic bottom plate, where raised sealing lands seal the membrane against the bottom face of the top plate. FIGS. 2A and 2B show a single lane of the top plate above the sealing land on the bottom plate, and FIG. 41C shows how the sealing land seals around channels cut in the top plate to form the diaphragm pumps and fluid channels. The diaphragm pumps are described in detail by Inman (Inman et al., *Journal of Micromechanics and Microengineering*, 17(5):891-899 (2007)). The platforms were held together by ½ in. long 4-40 screws with Belleville washers, which acted as preload springs.

A media exchange system, consisting of a fresh media reservoir, a pump, and passive spilling into an effluent collection reservoir, replenished nutrients and flushed out waste products.

Programmable Media Exchange

Fresh media was stored in a reservoir designed to hold a maximum of 1 mL. The top of the reservoir had a sharp edge designed to constrain the meniscus and minimize the chance of fluid bridging between the reservoir and the oxygenator or neighboring reservoirs. The 1 mL capacity fresh media reservoir includes as a sharp edge at the top to confine the meniscus, and an intake hole that is offset from the wall to allow flow rate measurement with the flow rate measuring tool. The flow rate measuring tool was stainless tube with a clear region and two clips along the tube. The clear region is placed in 1 mm fluid exit holes in the MPS and media supply reservoir, such that the o-ring seals against the platform. The time required for a fluid front to pass through the clear region of tubing between the two clips is measured using a stopwatch. The tube volume of 39.3 µL between the clips is divided by this time to obtain the flow rate.

The media exchange pump shown in FIG. 2B fed fresh media into the oxygenator channel. The resulting excess media volume was discharged from the MPS by passive spilling through the spillway and into the effluent collection. To estimate the concentration of nutrients and waste products in the fluid leaving the MPS, it was considered that the total circulating volume was well-mixed. If the media feed was continuous, and 500 µL were introduced each day, the media addition rate was 0.006 µL/s; comparing to the oxygenator and recirculation flow rates of 1 µL/s or greater, it was reasonable to assume the fresh media was well-mixed with the MPS volume.

Pump and Screw Layout

The LIVERCHIP® has 12 channels, with one pump per channel, each one in a straight line from one end of the lane to the other. The layout of the screws and the pneumatic channels is therefore relatively straightforward. The 6×R, while it has only 6 lanes, has 3 pumps per lane, and the recirculation channel must double back. In prototyping previous platforms with similar pumps and sealing lands, leaking had been a significant problem, and a rule of thumb was developed that no more than one sealing land should occur between two screws. The finite element study helped to qualitatively assess the design. Because this sealing is critical to proper function, it may be worthwhile to fabricate an SLA model for leak testing before fabricating parts. A "polycarbonate-like" resin such as ACCURA® 60 (3D Systems, Rock Hill, SC) may be a suitable alternative to polysulfone, as it has an elastic modulus approximate to the elastic modulus of polysulfone enough to make meaningful design decisions. For the screw layout for revision 2, a fluid leak testing showed that one row of screws could be removed without resulting in leaking when the platform was left pumping water with food dye overnight. The clamping screws were tightened to 5 cNm. Tightening to 15 cNm prevented the pumps from actuating; this may be caused by the compressed polyurethane squeezing into the pump and valve chambers, causing the membrane in the chamber to buckle.

Pneumatic Bottom Plate

The pneumatic bottom plate is separated from the culture medium by the membrane, and therefore does not have to be sterile or biocompatible. It is constructed from two acrylic plates that are solvent-bonded together, after the internal pneumatic channels are machined. These internal channels connect air and vacuum from the pneumatic fittings to the pump chambers.

Because of the high density of fasteners, and the presence of three pumps (each of which requires three distribution channels), there was a very thin wall between the screw clearance holes and the pneumatic channels on the Rev 2 pneumatic plate. The thin walls did not provide a reliable seal.

To resolve this issue, after the leak test indicated that a row of screws could be removed, an altered revision with a thicker wall was sent for manufacture (the change is shown in FIGS. 41A and 41B).

After machining, the fluidic and pneumatic plates were deburred using a dry ice blasting service (Nitrofreeze, Worcester, MA). This freezes any small burrs from machining and breaks them off with the impact of fine dry ice pellets, leaving a clean surface without risk of grit remaining in the platforms.

Results

The manufactured revision 2 platforms met the following requirements: (1) the device was made cell and drug compatible by using materials used and approved in existing platforms; VITON® does not appreciably adsorb the compounds measured, and absorption may be entirely negligible during short-term experiments; (2) the circulating volume was at the threshold of 500 µL, varying on the order of 7% from well to well; the precise value was dependent on the measurement of the volume captured in the oxygenator, which was also flow-rate dependent; (3) media exchange could be programmed and could store 1 mL of fresh media, and collect the waste by passive spilling; (4) the platform accommodated the same sterile technique that has been used on other platforms, and could be similarly moved between the incubator and Biological Safety Cabinet; (5) the platform accepted a commercially-available Costal universal lid; and (6) the pneumatic manifold integrated with the existing hardware.

Flow Rate Measurement

To measure the recirculation flow rate, the flow rate measuring tool was inserted in the central hole in the MPS bottom and pressed down such that the o-ring sealed. The MPS was filled with fluid such that the recirculation inlet did not run dry. Fluid was pumped up through the tool, paused, and pumped back down, to obtain measurements for upward and downward flow. The upward flow was therefore pushing against a pressure head of less than 100 mm of water, and the downward flow was assisted by the same.

The inlet to the oxygenator did not allow the tool tip to seal, so the hole at the start of the oxygenator spiral was plugged using a pipette tip (20-200 µL) that was plugged with silicone, and the flow rate was measured through the media exchange inlet. The media exchange pump and valves were actively held open during this test.

The measured flow rates across the 6 wells are shown in FIG. 42. All pumps measure about 10% lower than predicted based on nominal geometry. This may be due to the pump chamber geometry being smaller than expected, in which case a calibration factor may be added to the pump driving software, but it is necessary to re-measure these flow rates with a pneumatic plate that does not leak and can provide full actuation pressures.

Volume Recovery

To measure the circulating volume, the MPS and oxygenator were flooded with BSA solution until spilling occurred, and allowed to sit in the incubator for 1.5 hrs to come to temperature. The pumps were off, and none of the scaffold assembly was present in the MPS. After spilling, the volume remaining in the MPS and oxygenator was pipetted onto a scale, and the mass remaining in each well was recorded. An average of 510±33 µL was recovered (95% confidence). Subtracting the volume of the retaining ring and gasket (39 µL), scaffold (25 µL), and scaffold support (54 µL), all measured calculated from 3D CAD models, and adding the fluid trapped in channels (55 µL) and an estimated 50 µL in the oxygenator when running, the circulating volume was 497±33 µL. Note that this value depends on an estimate of the oxygenator volume. While pipetting 50 µL of BSA solution onto the oxygenator produced a profile comparable to that during flow at 2 µL/s, but stopping flow and immediately aspirating was only able to recover 10-15 µL. Nonetheless, the oxygenator volume was small compared to the overall 500 µL volume.

Evaporation Test

Evaporation of media during cell culture is a critical consideration for an open well platform. As the water evaporates, the concentration of the nutrients and waste products increases, which will introduce error. Further, significant evaporation can lead to drying of the MPS, causing either direct drying of the cells or pulling air bubbles into the recirculation, either of which will adversely affect the cells.

An initial test of the evaporation rate on the revision 2 platform was conducted by placing a silicone sheet over the bottom of the leaking pneumatic plate and wrapping the seam with electrical tape. The measured evaporation rate ranged from 144 to 220 µL/day, and the outer two lanes show the most evaporation. These values were much higher than the approximately 60 µL/day observed on the LIVER-CHIP® (unpublished data). A properly sealed pneumatic plate may lower evaporation rate.

Overall, six replicate lanes were effectively packaged on a single platform that as compatible with a standard tissue culture lid. The layout of pumps, channels, and screws successfully sealed the fluidic side while allowing separate pumping for perfusing the cell scaffold, flowing through the oxygenator, and providing fresh media. The waste media spilled passively into an effluent reservoir, which effectively controlled fluid height, limiting the circulating to the 500 µL target.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A fluidic device for cell or tissue culture comprising:
   a first plate comprising one or more lanes, each lane comprising
   a) at least one well for cell or tissue culture comprising a three-dimensional space defined by a bottom surface and a circumferential wall; and
   an inlet and an outlet in each well;
   b) at least one oxygenator comprising a body with a three-dimensional geometry and an oxygenator inlet and an oxygenator outlet, wherein the at least one oxygenator is in an open-well flow-through platform; and
   c) a network of fluid paths providing fluid connectivity between the at least one well for cell or tissue culture and the at least one oxygenator through the inlet, and optionally, the outlet of each well, wherein the at least one well for cell or tissue culture, the at least one oxygenator, and at least one fluid path in the network of fluid paths providing fluid connectivity from the at least one well to the at least one oxygenator have a total circulating volume of fluid between about 300 µL and 1000 µL,
   further comprising a detachable second plate comprising a pneumatic manifold and pneumatic fittings, and a barrier membrane positioned between the first plate and the second plate.

2. The fluidic device of claim 1, wherein the detachable second plate comprising a pneumatic manifold and pneumatic fittings, and the barrier membrane positioned between the first plate and the second plate are bonded to the first plate.

3. The fluidic device of claim 1 comprising at least one, at least two, or at least three pumps per lane.

4. The fluidic device of claim 1, wherein the three-dimensional geometry of the at least one oxygenator is selected from the group consisting of a plane, a pyramid, a cone, a cylinder, a cube, a sphere, a rectangle, an oblong, a filament, a spiral, and an ovoid.

5. The fluidic device of claim 1, wherein the body of the least one oxygenator further includes features providing surface geometry to the at least one oxygenator.

6. The fluidic device of claim 5, wherein the features are selected from the group consisting of interior corner, exterior corner, groove, channel, filament, gaps, surface modifications, surface roughness variations, and successive barriers, wherein these alter surface tension.

7. The fluidic device of claim 1, wherein the at least one oxygenator has an overall height between about 1 mm and 20 mm, an overall length or exterior diameter between about 2 mm and 100 mm, and provides a fluid path length between about 50 mm and 500 mm.

8. The fluidic device of claim 1, wherein the oxygenator body has a geometry of a spiral having between one and 12 steps along the height of the at least one oxygenator.

9. The fluidic device of claim 1, wherein a fluid in the at least one oxygenator has a fluid profile with a width (w) between about 0.5 mm and 1.5 mm and a height (h) between about 0.2 mm and 1 mm.

10. The fluidic device of claim 1, wherein the at least one oxygenator provides fluid oxygen concentration between about 65 µM and about 400 µM.

11. The fluidic device of claim 1, wherein the at least one well for cell or tissue culture and the at least one oxygenator are coupled through a fluidic path having at least one pump.

12. The fluidic device of claim 1, wherein the inlet and the outlet of the at least one well for cell or tissue culture are connected by a fluidic path having at least one pump.

13. The fluidic device of claim 1, further comprising a media reservoir comprising a media inlet coupled to the at least one oxygenator and/or well for cell or tissue culture by a fluidic path.

14. The fluidic device of claim 13, wherein the fluidic path coupling the media inlet to the at least one oxygenator comprises at least one pump.

15. The fluidic device of claim 1 providing fluid flow according to a configuration selected from the group consisting of in-line circulation, co-flow circulation, counter-flow circulation, laminar Figure-8 circulation, and selective sourcing.

16. The fluidic device of claim 1, wherein the at least one well for cell or tissue culture and/or the at least one oxygenator includes an oxygen probe for sensing fluid oxygen levels.

17. A system comprising multiple fluidic devices of claim 1.

18. The system of claim 17 further comprising organ or tissue specific cells in a fluidic multi-well device for cell or tissue culture.

19. The system of claim 18, comprising multiple fluidic multi-well for cell or tissue culture devices comprising organ or tissue specific cells, wherein the organ or tissue specific cells are of a different origin in each of the multi-well devices.

20. The system of claim 19 comprising multiple wells for cell or tissue culture, wherein the multiple wells contain cells, wherein the cells are of different origin in at least two wells.

21. The system of claim 20, wherein the cells in the multiple wells are selected from the group consisting of liver cells, intestinal cells, pancreatic cells, muscle cells, bladder cells, kidney cells, pluripotent cells, and hematopoietic cells.

22. A method of culturing cells comprising seeding the fluidic device of claim 1 with cells.

23. The method of claim 22 further comprising exposing the cells to an agent to determine its effect on the cells.

24. The method of claim 23 further comprising administering the agent in different dosages, in a different dosing regimen, or in combination with one or more other agents and determining its effect on the cells.

25. The method of claim 22, wherein the agent is administered to different cell types or cell types associated with one or more diseases or disorders.

* * * * *